US006329379B1

(12) United States Patent
Llinas-Brunet et al.

(10) Patent No.: US 6,329,379 B1
(45) Date of Patent: Dec. 11, 2001

(54) HEPATITIS C INHIBITOR TRI-PEPTIDES

(75) Inventors: Montse Llinas-Brunet, D.D.O.; Murray D. Bailey, Pierrefonds; Dale R. Cameron, Rosemere; Elise Ghiro, Laval; Nathalie Goudreau, Mont-Royal; Marc-Andre Poupart, Vimont; Jean Rancourt, Laval; Youla S. Tsantrizos, Saint-Laurent; Anne-Marie Faucher, Oka; Teddy Halmos; Dominik M. Wernic, both of Laval, all of (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 0 days.

(21) Appl. No.: 09/675,398

(22) Filed: Sep. 29, 2000

Related U.S. Application Data

(62) Division of application No. 09/368,866, filed on Aug. 5, 1999
(60) Provisional application No. 60/095,931, filed on Aug. 10, 1998, and provisional application No. 60/132,386, filed on May 4, 1999.

(51) Int. Cl.[7] .................. A61K 31/505; A61K 31/52; C07D 239/00; C07D 239/72; C07D 239/02
(52) U.S. Cl. .................. 514/256; 514/259; 514/260; 514/266; 514/269; 514/273; 544/242; 544/298; 544/304; 544/283; 544/287
(58) Field of Search .................. 514/256, 259, 514/260, 266, 269, 273; 544/242, 298, 304, 283, 287

(56) References Cited

FOREIGN PATENT DOCUMENTS

| 196 00 034 A1 | 7/1997 | (DE). |
| WO 98 17679 A | 4/1998 | (WO). |
| WO99 07733 A | 2/1999 | (WO). |

OTHER PUBLICATIONS

Gaucher, et al: "Palladium (0) Catalyzed Tandem Alkylation and SN' Cyclization of 1,4–Dichlorobut–2–ene by the N–(Diphenylmethylene) acetonitrile. A Stereoselective Synthesis of 1–Aminocyclo–propanecarboxylic Acids"; Tetrahedron Letters, vol. 36, No. 17, p. 2979–2982; 1995.

Fliche, et al; "Enantioselective synthesis of (1R, 2S) and (1S, 2S) dehydrocoronamic acids", Synthetic Communications; vol. 24, No. 20, 1994, p. 2873–2876.

Chen, et al; "Chirally selective hydrolysis of D, L amino acid esters by alkaline protease"; J. Chem, Soc. Chem. Commun., vol. 20, 1986, p. 1514–1516.

Chen, et al., "Kinetic resolution of esters of amino acids in t–butanol containing 5% water catalyzed by a stable industrial alkaline protease"; Chirality, vol. 6, 1994, p. 572–576.

(List continued on next page.)

*Primary Examiner*—Deborah C. Lambkin
(74) *Attorney, Agent, or Firm*—Robert P. Raymond; Alan R. Stempel; Mary-Ellen M. Devlin

(57) ABSTRACT

Racemates, diastereoisomers and optical isomers of a compound of formula (I):

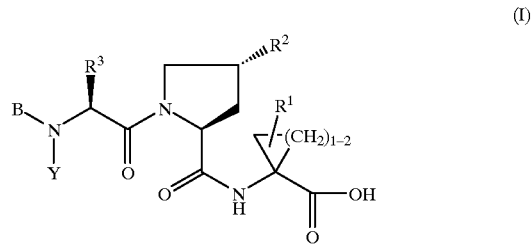

wherein

B is H, a $C_6$ or $C_{10}$ aryl, $C_{7-16}$ aralkyl; Het or (lower alkyl)-Het, all of which optionally substituted with $C_{1-6}$ alkyl; $C_{1-6}$ alkoxy; $C_{1-6}$ alkanoyl; hydroxy; hydroxyalkyl; halo; haloalkyl; nitro; cyano; cyanoalkyl; amino optionally substituted with $C_{1-6}$ alkyl; amido; or (lower alkyl)amide; or B is an acyl derivative of formula $R_4$—C(O)—; a carboxyl of formula $R_4$—O—C(O)—; an amide of formula $R_4$—N($R_5$)—C(O)—; a thioamide of formula $R_4$—N($R_5$)—C(S)—; or a sulfonyl of formula $R_4$—$SO_2$; $R_5$ is H or $C_{1-6}$ alkyl; and Y is H or $C_{1-6}$ alkyl;

$R^3$ is $C_{1-8}$ alkyl, $C_{3-7}$ cycloalkyl, or $C_{4-10}$ alkylcycloalkyl, all optionally substituted with hydroxy, $C_{1-6}$ alkoxy, $C_{1-6}$ thioalkyl, amido, (lower alkyl)amido, $C_6$ or $C_{10}$ aryl, or $C_{7-16}$ aralkyl;

$R_2$ is $CH_2$—$R_{20}$, NH—$R_{20}$, O—$R_{20}$ or S—$R_{20}$, wherein $R_{20}$ is a saturated or unsaturated $C_{3-7}$ cycloalkyl or $C_{4-10}$ (alkylcycloalkyl), all of which being optionally mono-, di- or tri-substituted with $R_{21}$, or $R_{20}$ is a $C_6$ or $C_{10}$ aryl or $C_{7-14}$ aralkyl optionally substituted, or $R_{20}$ is Het or (lower alkyl)-Het, both optionally substituted, Het or (lower alkyl)-Het; carboxyl; carboxy(lower alkyl); $C_6$ or $C_{10}$ aryl, $C_{7-14}$ aralkyl or Het, said aryl, aralkyl or Het being optionally substituted; and $R^1$ is H; $C_{1-6}$ alkyl, $C_{3-7}$ cycloalkyl, $C_{2-6}$ alkenyl, or $C_{2-6}$ alkynyl, all optionally substituted with halogen; or a pharmaceutically acceptable salt or ester thereof.

52 Claims, No Drawings

OTHER PUBLICATIONS

Llinas–Brunet, M., et al; "Peptide–based inhibitors of the hepatitis C virus serine protease", Bioorganic & Medicinal Chemistry Letters, vol. 8, No. 13, p. 1713–1718; 1998.

Gershonov et al; "1–Aminocyclobutanecarboxylic acid derivatives as novel structural elements in bioactive peptides: application to tufsin analogs"; Journal of Medicinal Chemistry, vol. 39, No. 24, 1996, p. 4833–4843.

Ogawa, Tomohisa et al: "2,3–Methanophenylalanine and.Alpha., .Beta.–Dehydrophenylalanine Derivatives as Chymotrypsin Inhibitor"; Pept. Chem. (1990), vol.27: p. 379–382.

HEPATITIS C INHIBITOR TRI-PEPTIDES

This application is a divisional of U.S. application Ser. No. 09/368,866, filed on Aug. 5, 1999, which claims the benefit of U.S. Provisional Application No. 60/095,031, filed Aug. 10, 1998, and U.S. Provisional Application No. 60/132,386, filed May. 4, 1999.

FIELD OF THE INVENTION

The present invention relates to compounds, process for their synthesis, compositions and methods for the treatment of hepatitis C virus (HCV) infection. In particular, the present invention provides novel peptide analogs, pharmaceutical compositions containing such analogs and methods for using these analogs in the treatment of HCV infection. The present invention also provides processes and intermediates for the synthesis of these peptide analogs.

BACKGROUND OF THE INVENTION

Hepatitis C virus (HCV) is the major etiological agent of post-transfusion and community-acquired non-A non-B hepatitis worldwide. It is estimated that over 150 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulins treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy.

Therefore, a need exists for the development of effective antiviral agents for treatment of HCV infection that overcomes the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2-NS3 junction; the second one is a serine protease contained within the N-terminal region of NS3 (henceforth referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV. A general strategy for the development of antiviral agents is to inactivate virally encoded enzymes that are essential for the replication of the virus. In this vein, patent application WO 97/06804 describes the (−) enantiomer of the nucleoside analogue cytosine-1,3-oxathiolane (also known as 3TC) as active against HCV. This compound, although reported as safe in previous clinical trials against HIV and HBV, has yet to be clinically proven active against HCV and its mechanism of action against the virus has yet to be reported.

Intense efforts to discover compounds which inhibit the NS3 protease or RNA helicase of HCV have led to the following disclosures:

U.S. Pat. No. 5,633,388 describes heterocyclic-substituted carboxamides and analogues as being active against HCV. These compounds are directed against the helicase activity of the NS3 protein of the virus but clinical tests have not yet been reported.

A phenanthrenequinone has been reported by Chu et al., (Tet. Lett., (1996), 7229–7232) to have activity against the HCV NS3 protease in vitro. No further development on this compound has been reported.

A paper presented at the Ninth International Conference on Antiviral Research, Urabandai, Fukyshima, Japan (1996) (Antiviral Research, (1996), 30, 1, A23 (abstract 19)) reports thiazolidine derivatives to be inhibitory to the HCV protease.

Several studies have reported compounds inhibitory to other serine proteases, such as human leukocyte elastase. One family of these compounds is reported in WO 95/33764 (Hoechst Marion Roussel, 1995). The peptides disclosed in this application are morpholinylcarbonyl-benzoyl-peptide analogues that are structurally different from the peptides of the present invention.

WO 98/17679 from Vertex Pharmaceuticals Inc. discloses inhibitors of serine protease, particularly, Hepatitis C virus NS3 protease. These inhibitors are peptide analogues based on the NS5A/5B natural substrate. Although several tripeptides are disclosed, all of these peptide analogues contain C-terminal activated carbonyl function as an essential feature. These analogues were also reported to be active against other serine protease and are therefore not specific for HCV NS3 protease.

Hoffman LaRoche has also reported hexapeptides that are proteinase inhibitors useful as antiviral agents for the treatment of HCV infection. These peptides contain an aldehyde or a boronic acid at the C-terminus.

Steinkühler et al. and Ingallinella et al. have published on NS4A-4B product inhibition (Biochemistry (1998), 37, 8899–8905 and 8906–8914). However, the peptides and peptide analogues presented do not include nor do they lead to the design of the peptides of the present invention.

One advantage of the present invention is that it provides tripeptides that are inhibitory to the NS3 protease of the hepatitis C virus.

A further advantage of one aspect of the present invention resides in the fact that these peptides specifically inhibit the NS3 protease and do not show significant inhibitory activity at concentrations up to 300 $\mu$M against other serine proteases such as human leukocyte elastase (HLE), porcine pancreatic elastase (PPE), or bovine pancreatic chymotypsin, or cysteine proteases such as human liver cathepsin B (Cat B).

A further advantage of the present invention is that it provides small peptides of low molecular weight that may be capable of penetrating cell membranes and may be active in cell culture and in vivo with good pharmacokinetic profile.

SUMMARY OF THE INVENTION

Included in the scope of the invention are racemates, diastereoisomers and optical isomers of a compound of formula (I):

wherein
- B is H, a $C_6$ or $C_{10}$ aryl, $C_{7-16}$ aralkyl; Het or (lower alkyl)-Het, all of which optionally substituted with $C_{1-6}$ alkyl; $C_{1-6}$ alkoxy; $C_{1-6}$ alkanoyl; hydroxy; hydroxyalkyl; halo; haloalkyl; nitro; cyano; cyanoalkyl; amino optionally substituted with $C_{1-6}$ alkyl; amido; or (lower alkyl)amide;
- or B is an acyl derivative of formula $R_4$—C(O)—; a carboxyl derivative of formula $R_4$—O—C(O)—; an amide derivative of formula $R_4$—N($R_5$)—C(O)—; a thioamide derivative of formula $R_4$—N($R_5$)—C(S)—; or a sulfonyl derivative of formula $R_4$—$SO_2$ wherein $R_4$ is
  - (i) $C_{1-10}$ alkyl optionally substituted with carboxyl, $C_{1-6}$ alkanoyl, hydroxy, $C_{1-6}$ alkoxy, amino optionally mono- or di-substituted with $C_{1-6}$ alkyl, amido, or (lower alkyl) amide;
  - (ii) $C_{3-7}$ cycloalkyl, $C_{3-7}$ cycloalkoxy, or $C_{4-10}$ alkylcycloalkyl, all optionally substituted with hydroxy, carboxyl, ($C_{1-6}$ alkoxy)carbonyl, amino optionally mono- or di-substituted with $C_{1-6}$ alkyl, amido, or (lower alkyl) amide;
  - (iii) amino optionally mono- or di-substituted with $C_{1-6}$ alkyl; amido; or (lower alkyl)amide;
  - (iv) $C_6$ or $C_{10}$ aryl or $C_{7-6}$ aralkyl, all optionally substituted with $C_{1-6}$ alkyl, hydroxy, amido, (lower alkyl)amide, or amino optionally mono- or di-substituted with $C_{1-6}$ alkyl; or
  - (v) Het or (lower alkyl)-Het, both optionally substituted with $C_{1-6}$ alkyl, hydroxy, amido, (lower alkyl) amide, or amino optionally mono- or di-substituted with $C_{1-6}$ alkyl;
- $R_5$ is H or $C_{1-6}$ alkyl;
- with the proviso that when B is a carboxyl derivative, an amide derivative or a thioamide derivative, $R_4$ is not a cycloalkoxy; and
- Y is H or $C_{1-6}$ alkyl;
- $R^3$ is $C_{1-8}$ alkyl, $C_{3-7}$ cycloalkyl, or $C_{4-10}$ alkylcycloalkyl, all optionally substituted with hydroxy, $C_{1-6}$ alkoxy, $C_{1-6}$ thioalkyl, amido, (lower alkyl)amido, $C_6$ or $C_{10}$ aryl, or $C_{7-16}$ aralkyl;
- $R_2$ is $CH_2$-$R_{20}$, NH-$R_{20}$, O-$R_{20}$ or S-$R_{20}$, wherein $R_{20}$ is a saturated or unsaturated $C_{3-7}$ cycloalkyl or $C_{4-10}$ (alkylcycloalkyl), all of which being optionally mono-, di- or tri-substituted with $R_{21}$, or $R_{20}$ is a $C_6$ or $C_{10}$ aryl or $C_{7-14}$ aralkyl, all optionally mono-, di- or tri-substituted with $R_{21}$, or $R_{20}$ is Het or (lower alkyl)-Het, both optionally mono-, di- or tri-substituted with $R_{21}$, wherein each $R_{21}$ is independently $C_{1-6}$ alkyl; $C_{1-6}$ alkoxy; lower thioalkyl;
  - sulfonyl; $NO_2$; OH; SH; halo; haloalkyl; amino optionally mono- or di-substituted with $C_{1-6}$ alkyl, $C_6$ or $C_{10}$ aryl, $C_{7-14}$ aralkyl, Het or (lower alkyl)-Het;
  - amido optionally mono-substituted with $C_{1-6}$ alkyl, $C_6$ or $C_{10}$ aryl, $C_{7-14}$ aralkyl, Het or (lower alkyl)-Het;
  - carboxyl; carboxy(lower alkyl); $C_6$ or $C_{10}$ aryl, $C_{7-14}$ aralkyl or Het, said aryl, aralkyl or Het being optionally substituted with $R_{22}$;
  - wherein $R_{22}$ is $C_{1-6}$ alkyl; $C_{3-7}$ cycloalkyl; $C_{1-6}$ alkoxy; amino optionally mono- or di-substituted with $C_{1-6}$ alkyl; sulfonyl; (lower alkyl)sulfonyl; $NO_2$; OH; SH; halo; haloalkyl; carboxyl; amide; (lower alkyl)amide; or Het optionally substituted with $C_{1-6}$ alkyl
- $R^1$ is H, $C_{1-6}$ alkyl, $C_{3-7}$ cycloalkyl, $C_{2-6}$ alkenyl, or $C_{2-6}$ alkynyl, all optionally substituted with halogen;

or a pharmaceutically acceptable salt or ester thereof.

Included within the scope of this invention is a pharmaceutical composition comprising an anti-hepatitis C virally effective amount of a compound of formula I, or a therapeutically acceptable salt or ester thereof, in admixture with a pharmaceutically acceptable carrier medium or auxiliary agent.

An important aspect of the invention involves a method of treating a hepatitis C viral infection in a mammal by administering to the mammal an anti-hepatitis C virally effective amount of the compound of formula I, or a therapeutically acceptable salt or ester thereof or a composition as described above.

Another important aspect involves a method of inhibiting the replication of hepatitis C virus by exposing the virus to a hepatitis C viral NS3 protease inhibiting amount of the compound of formula I, or a therapeutically acceptable salt or ester thereof or a composition as described above.

Still another aspect involves a method of treating a hepatitis C viral infection in a mammal by administering thereto an anti-hepatitis C virally effective amount of a combination of the compound of formula I, or a therapeutically acceptable salt or ester thereof. According to one embodiment, the pharmaceutical compositions of this invention comprise an additional immunomodulatory agent.

Examples of additional immunomodulatory agents include but are not limited to, α-, β-, and δ-interferons.

DETAILED DESCRIPTION OF PREFERRED EMBODIMENTS

Definitions

As used herein, the following definitions apply unless otherwise noted: With reference to the instances where (R) or (S) is used to designate the configuration of a substituent, e.g. $R^1$ of the compound of formula I, the designation is done in the context of the compound and not in the context of the substituent alone.

The natural amino acids, with exception of glycine, contain a chiral carbon atom. Unless otherwise specifically indicated, the compounds containing natural amino acids with the L-configuration are preferred. However, applicants contemplate that when specified, some amino acids of the formula I can be of either D- or L-configuration or can be mixtures of D- and L-isomers, including racemic mixtures.

The designation "P1, P2 and P3" as used herein refer to the position of the amino acid residues starting from the C-terminus end of the peptide analogues and extending towards the N-terminus [i.e. P1 refers to position 1 from the C-terminus, P2: second position from the C-terminus, etc.) (see Berger A. & Schechter I., Transactions of the Royal Society London series (1970), B257, 249–264].

The abbreviations for the α-amino acids used in this application are set forth in Table A.

TABLE A

| Amino Acid | Symbol |
| --- | --- |
| 1-aminocyclopropyl-carboxylic acid | Acca |
| Alanine | Ala |
| Aspartic acid | Asp |
| Cysteine | Cys |
| Cyclohexylglycine (also named: 2-amino-2-cyclohexylacetic acid) | Chg |
| Glutamic acid | Glu |
| Isoleucine | Ile |
| Leucine | Leu |
| Phenylalanine | Phe |
| Proline | Pro |
| Valine | Val |
| tert-Butylglycine | Tbg |

As used herein the term "1-aminocyclopropyl-carboxylic acid" (Acca) refers to a compound of formula:

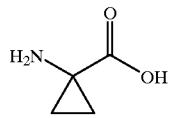

As used herein the term "tert-butylglycine" refers to a compound of formula:

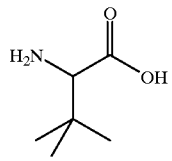

The term "residue" with reference to an amino acid or amino acid derivative means a radical derived from the corresponding α-amino acid by eliminating the hydroxyl of the carboxy group and one hydrogen of the α-amino group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

The term "halo" as used herein means a halogen substituent selected from bromo, chloro, fluoro or iodo.

The term "$C_{1-6}$ alky" or "(lower)alky" as used herein, either alone or in combination with another substituent, means acyclic, straight or branched chain alkyl substituents containing from 1 to six carbon atoms and includes, for example, methyl, ethyl, propyl, butyl, tert-butyl, hexyl, 1-methylethyl, 1-methylpropyl, 2-methylpropyl, 1,1-dimethylethyl.

The term "$C_{3-7}$ cycloalkyl" as used herein, either alone or in combination with another substituent, means a cycloalkyl substituent containing from three to seven carbon atoms and includes cyclopropyl, cyclobutyl, cyclopentyl, cyclohexyl and cycloheptyl. This term also includes "spiro"-cyclic group such as spiro-cyclopropyl or spiro-cyclobutyl:

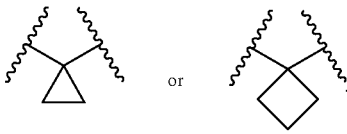

The term "unsaturated cycloalkyl" includes, for example, cyclohexenyl:

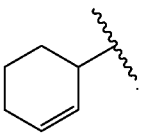

The term "$C_{4-10}$ (alkylcycloalkyl) as used herein means a cycloalkyl radical containing from three to seven carbon atoms linked to an alkyl radical, the linked radicals containing up to ten carbon atoms; for example, cyclopropylmethyl, cyclopentylethyl, cyclohexylmethyl, cyclohexylethyl or cycloheptylethyl.

The term "$C_{2-10}$ alkenyl" as used herein, either alone or in combination with another radical, means an alkyl radical as defined above containing from 2 to 10 carbon atoms, and further containing at least one double bond. For example alkenyl includes allyl and vinyl.

The term "$C_{1-6}$ alkanoyl" as used herein, either alone or in combination with another radical, means straight or branched 1-oxoalkyl radicals containing one to six carbon atoms and includes formyl, acetyl, 1-oxopropyl (propionyl), 2-methyl-1-oxopropyl, 1-oxohexyl and the like.

The term "$C_{1-6}$ alkoxy" as used herein, either alone or in combination with another radical, means the radical —O($C_{1-6}$ alkyl) wherein alkyl is as defined above containing up to six carbon atoms. Alkoxy includes methoxy, ethoxy, propoxy, 1-methylethoxy, butoxy and 1,1-dimethylethoxy. The latter radical is known commonly as tert-butoxy.

The term "C$_{3-7}$ cycloalkoxy" as used herein, either alone or in combination with another radical, means a C$_{3-7}$ cycloalkyl group linked to an oxygen atom, such as, for example:

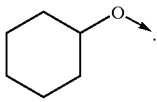

The term "C$_6$ or C$_{10}$ aryl" as used herein, either alone or in combination with another radical, means either an aromatic monocyclic group containing 6 carbon atoms or an aromatic bicyclic group containing 10 carbon atoms. For example, aryl includes phenyl, 1-naphthyl or 2-naphthyl.

The term "C$_{7-16}$ aralkyl" as used herein, either alone or in combination with another radical, means a C$_6$ or C$_{10}$ aryl as defined above linked to an alkyl group, wherein alkyl is as defined above containing from 1 to 6 carbon atoms. C$_{7-16}$ aralkyl includes for example benzyl, butylphenyl, and 1-naphthylmethyl.

The term "amino aralkyl" as used herein, either alone or in combination with another radical, means an amino group substituted with a C$_{7-16}$ aralkyl group, such as, for example, the amino aralkyl:

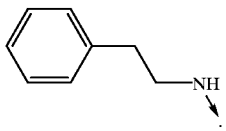

The term "(lower alkyl)amide" as used herein, either alone or in combination with another radical, means an amide mono-substituted with a C$_{1-6}$ alkyl, such as:

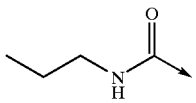

The term "carboxy(lower)alky" as used herein, either alone or in combination with another radical, means a carboxyl group (COOH) linked through a (lower)alkyl group as defined above and includes for example butyric acid.

The term "heterocycle" or "Het" as used herein, either alone or in combination with another radical, means a monovalent radical derived by removal of a hydrogen from a five-, six-, or seven-membered saturated or unsaturated (including aromatic) heterocycle containing from one to four heteroatoms selected from nitrogen, oxygen and sulfur. Furthermore, "Het" as used herein, means a heterocycle as defined above fused to one or more other cycle, be it a heterocycle or any other cycle. Examples of suitable heterocycles include: pyrrolidine, tetrahydrofuran, thiazolidine, pyrrole, thiophene, diazepine, 1H-imidazole, isoxazole, thiazole, tetrazole, piperidine, 1,4dioxane, 4-morpholine, pyridine, pyrimidine, thiazolo[4,5-b]-pyridine, quinoline, or indole, or the following heterocycles:

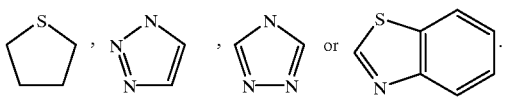

The term "(lower alkyl)-Het" as used herein, means a heterocyclic radical as defined above linked through a chain or branched alkyl group, wherein alkyl is as defined above containing from 1 to 6 carbon atoms. Examples of (lower alkyl)-Het include:

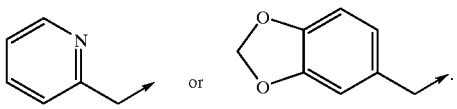

The term "pharmaceutically acceptable ester" as used herein, either alone or in combination with another substituent, means esters of the compound of formula I in which any of the carboxyl functions of the molecule, but preferably the carboxy terminus, is replaced by an alkoxycarbonyl function:

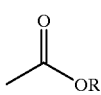

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, C$_{1-4}$ alkyl or C$_{1-4}$ alkoxy. Other suitable prodrug esters can be found in Design of prodrugs, Bundgaard, H. Ed. Elsevier (1985) incorporated herewith by reference. Such pharrhaceutically acceptable esters are usually hydrolyzed in vivo when injected in a mammal and transformed into the acid form of the compound of formula I.

With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group.

In particular the esters may be a C$_{1-6}$ alkyl ester, an unsubstituted benzyl ester or a benzyl ester substituted with at least one halogen, C$_{1-6}$ alkyl, C$_{1-6}$ alkoxy, nitro or trifluoromethyl.

The term "pharmaceutically acceptable salt" as used herein includes those derived from pharmaceutically acceptable bases. Examples of suitable bases include choline, ethanolamine and ethylenediamine. Na$^+$, K$^+$, and Ca$^{++}$ salts are also contemplated to be within the scope of the invention (also see Pharmaceutical salts, Birge, S. M. et al., J. Pharm. Sci., (1977), 66, 1–19, incorporated herein by reference).

Preferred Embodiments

Included within the scope of this invention are compounds of formula I wherein

Preferably, B is a C$_6$ or C$_{10}$ aryl or C$_{7-16}$ aralkyl, all optionally substituted with C$_{1-6}$ alkyl, C$_{1-6}$ alkoxy, C$_{1-6}$ alkanoyl, hydroxy, hydroxyalkyl, halo, haloalkyl, nitro, cyano, cyanoalkyl, amido, (lower alkyl)amido, or amino optionally substituted with C$_{1-6}$ alkyl; or B is preferably Het or (lower alkyl)-Het, all optionally substituted with C$_{1-6}$ alkyl, C$_{1-6}$ alkoxy, C$_{1-6}$ alkanoyl, hydroxy, hydroxyalkyl, halo, haloalkyl, nitro, cyano, cyanoalkyl, amido, (lower alkyl)amido, or amino optionally substituted with $C_{1-6}$ alkyl.

Alternatively, B is preferably $R_4$—$SO_2$ wherein $R_4$ is preferably $C_{1-6}$ alkyl; amido; (lower alkyl)amide; $C_6$ or $C_{10}$ aryl, $C_{7-14}$ aralkyl or Het, all optionally substituted with $C_{1-6}$ alkyl.

Alternatively, B is preferably an acyl derivative of formula $R_4$—C(O)— wherein $R_4$ is preferably (i) $C_{1-10}$ alkyl optionally substituted with carboxyl, hydroxy or $C_{1-6}$ alkoxy, amido, (lower alkyl)amide, or amino optionally mono- or di-substituted with $C_{1-6}$ alkyl;

(ii) $C_{3-7}$ cycloalkyl or $C_{4-10}$ alkylcycloalkyl, both optionally substituted with hydroxy, carboxyl, ($C_{1-6}$ alkoxy)carbonyl, amido, (lower alkyl)amide, or amino optionally mono- or di-substituted with $C_{1-6}$ alkyl;

(iv) $C_6$ or $C_{10}$ aryl or $C_{7-16}$ aralkyl, all optionally substituted with $C_{1-6}$ alkyl, hydroxy, amido, (lower alkyl)amide, or amino optionally substituted with $C_{1-6}$ alkyl;

(v) Het or (lower alkyl)-Het, both optionally substituted with $C_{1-6}$ alkyl, hydroxy, amino optionally substituted with $C_{1-6}$ alkyl, amido, (lower alkyl)amide, or amino optionally substituted with $C_{1-6}$ alkyl.

Alternatively, B is preferably a carboxyl of formula $R_4$—O—C(O)—, wherein $R_4$ is preferably (i) $C_{1-10}$ alkyl optionally substituted with carboxyl, $C_{1-6}$ alkanoyl, hydroxy, $C_{1-6}$ alkoxy, amino optionally mono- or di-substituted with $C_{1-6}$ alkyl, amido or (lower alkyl)amide;

(ii) $C_{3-7}$ cycloalkyl, $C_{4-10}$ alkylcycloalkyl, all optionally substituted with carboxyl, ($C_{1-6}$ alkoxy)carbonyl, amino optionally mono- or di-substituted with $C_{1-6}$ alkyl, amido or (lower alkyl)amide;

(iv) $C_6$ or $C_{10}$ aryl or $C_{7-16}$ aralkyl optionally substituted with $C_{1-6}$ alkyl, hydroxy, amido, (lower alkyl)amido, or amino optionally mono- or di-substituted with $C_{1-6}$ alkyl; or (v) Het or (lower alkyl)-Het, both optionally substituted with $C_{1-6}$ alkyl, hydroxy, amino optionally mono- or di-substituted with $C_{1-6}$ alkyl, amido or (lower alkyl)amido.

Alternatively, B is preferably an amide of formula $R_4$—N($R_5$)—C(O)— wherein $R_4$ is preferably (i) $C_{1-10}$ alkyl optionally substituted with carboxyl, $C_{1-6}$ alkanoyl, hydroxy, $C_{1-6}$ alkoxy, amido, (lower alkyl)amido, or amino optionally mono- or di-substituted with $C_{1-6}$ alkyl;

(ii) $C_{3-7}$ cycloalkyl or $C_{4-10}$ alkylcycloalkyl, all optionally substituted with carboxyl, ($C_{1-6}$ alkoxy)carbonyl, amido, (lower alkyl)amido, or amino optionally mono- or di-substituted with $C_{1-6}$ alkyl;

(iii) amino optionally mono- or di-substituted with $C_{1-3}$ alkyl;

(iv) $C_6$ or $C_{10}$ aryl or $C_{7-16}$ aralkyl, all optionally substituted with $C_{1-6}$ alkyl, hydroxy, amido, (lower alkyl)amide, or amino optionally substituted with $C_{1-6}$ alkyl; or (v) Het or (lower alkyl)-Het, both optionally substituted with $C_{1-6}$ alkyl, hydroxy, amino optionally substituted with $C_{1-6}$ alkyl, amido or (lower alkyl)amide; and $R_5$ is preferably H or methyl.

Alternatively, B is a preferably thioamide of formula $R_4$—NH—C(S)—; wherein $R_4$ is preferably (i) $C_{1-10}$ alkyl optionally substituted with carboxyl, $C_{1-6}$ alkanoyl or $C_{1-6}$ alkoxy;

(ii) $C_{3-7}$ cycloalkyl or $C_{4-10}$ alkylcycloalkyl, all optionally substituted with carboxyl, ($C_{1-6}$ alkoxy)carbonyl, amino or amido.

More preferably, B is a $C_6$ or $C_{10}$ aryl optionally substituted with $C_{1-6}$ alkyl, $C_{1-6}$ alkoxy, $C_{1-6}$ alkanoyl, hydroxy, hydroxyalkyl, halo, haloalkyl, nitro, cyano, cyanoalkyl, amido, (lower alkyl)amide, or amino optionally mono- or di-substituted with $C_{1-6}$ alkyl, such that B is for example:

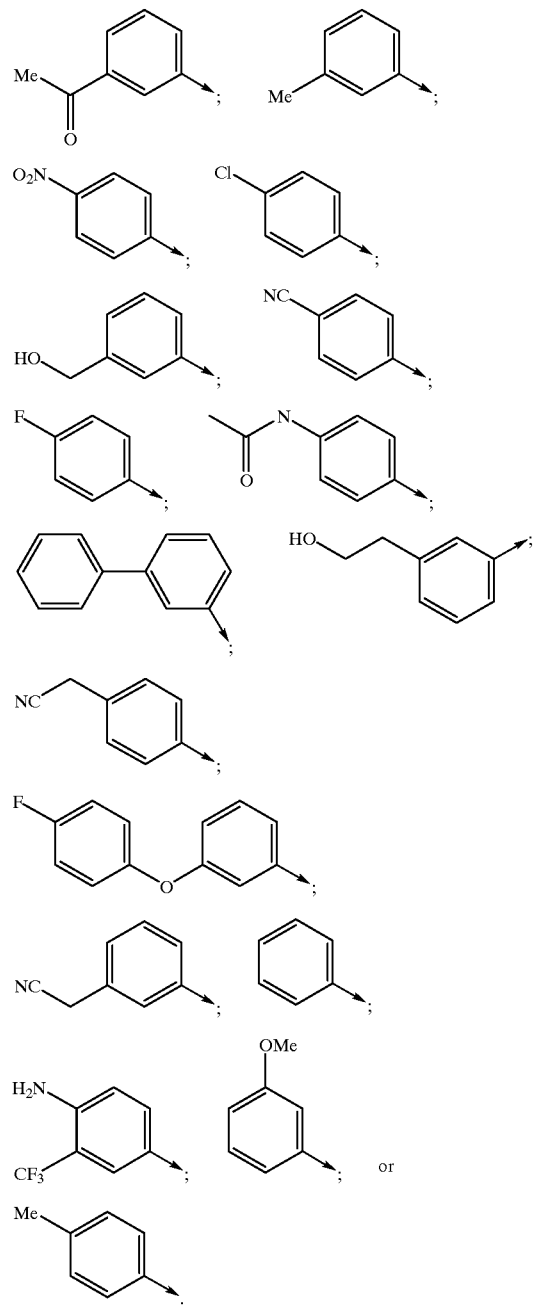

or B is more preferably Het optionally substituted with $C_{1-6}$ alkyl, $C_{1-6}$ alkoxy, $C_{1-6}$ alkanoyl, hydroxy, halo, amido, (lower alkyl)amide, or amino optionally mono- or di-substituted with $C_{1-6}$ alkyl, such that B is for example:

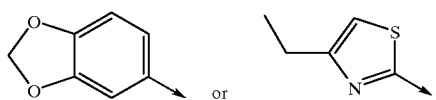 or

Alternatively, B is more preferably $R_4$—$SO_2$ wherein $R_4$ is preferably $C_6$ or $C_{10}$ aryl, a $C_{7-14}$ aralkyl or Het all optionally substituted with $C_{1-6}$ alkyl; amido, (lower alkyl) amide, such that B is, for example:

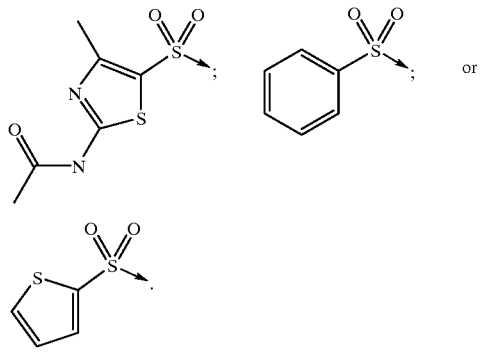 or

Alternatively, B is more preferably an acyl derivative of formula $R_4$—C(O)— wherein $R_4$ is preferably (i) $C_{1-10}$ alkyl optionally substituted with carboxyl, hydroxy or $C_{1-6}$ alkoxy; or (ii) $C_{3-7}$ cycloalkyl or $C_{4-10}$ alkylcycloalkyl, both optionally substituted with hydroxy, carboxyl, ($C_{1-6}$ alkoxy) carbonyl, such that B is, for example:

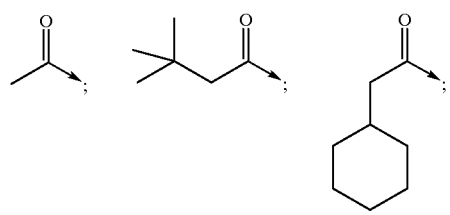

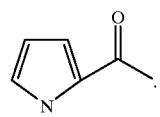

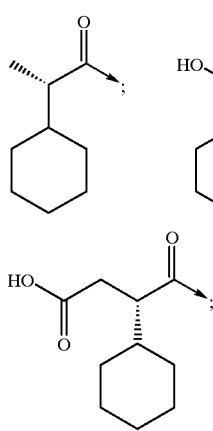 or

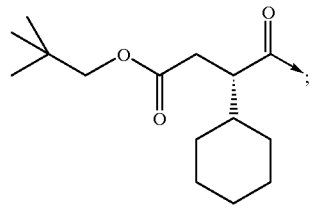

or $R_4$ is preferably (iv) $C_6$ or $C_{10}$ aryl or $C_{7-16}$ aralkyl, all optionally substituted with $C_{1-6}$ alkyl, hydroxy, such that B is for example:

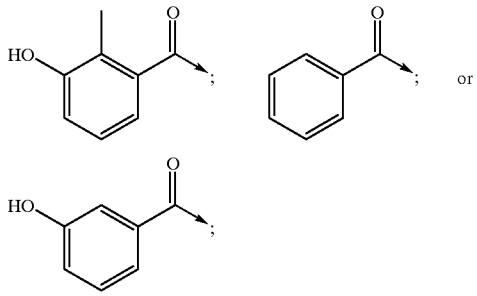

or $R_4$ is preferably (v) Het optionally substituted with $C_{1-6}$ alkyl, hydroxy, amido or amino, such that B is for example:

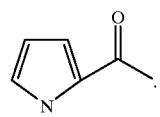

Alternatively, B is more preferably a carboxyl of formula $R_4$—O—C(O)—, wherein $R_4$ is preferably (i) $C_{1-10}$ alkyl optionally substituted with carboxyl, $C_{1-6}$ alkanoyl, hydroxy, $C_{1-6}$ alkoxy or amido, (lower alkyl) amide, amino optionally mono- or di-substituted with $C_{1-6}$ alkyl;

(ii) $C_{3-7}$ cycloalkyl, $C_{4-10}$ alkylcycloalkyl, all optionally substituted with carboxyl, ($C_{1-6}$ alkoxy)carbonyl, amido, (lower alkyl)amide, amino optionally mono- or di-substituted with $C_{1-6}$ alkyl, such that B is for example:

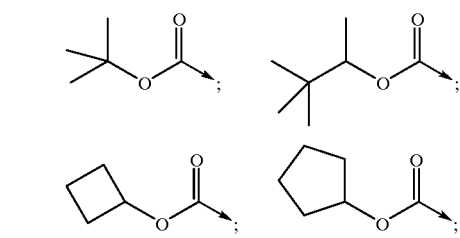

-continued

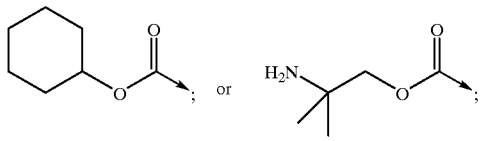

(iv) $C_6$ or $C_{10}$ aryl or $C_{7-16}$ aralkyl, all optionally substituted with $C_{1-6}$ alkyl, hydroxy, amino optionally substituted with $C_{1-6}$ alkyl; or (v) Het or (lower alkyl)-Het, both optionally substituted with $C_{1-6}$ alkyl, hydroxy, amido, or amino optionally mono-substituted with $C_{1-6}$ alkyl, such that B is for example:

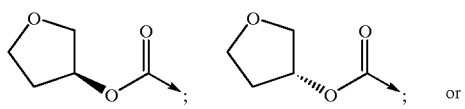

Alternatively, B is more preferably an amide of formula $R_4$—N($R_5$)—C(O)— wherein $R_4$ is preferably (i) $C_{1-10}$ alkyl optionally substituted with carboxyl, $C_{1-6}$ alkanoyl, hydroxy, $C_{1-6}$ alkoxy, amido, (lower alkyl) amide, amino optionally mono- or di-substituted with $C_{1-6}$ alkyl;

(ii) $C_{3-7}$ cycloalkyl or $C_{4-10}$ alkylcycloalkyl, all optionally substituted with carboxyl, ($C_{1-6}$ alkoxy)carbonyl, amido, (lower alkyl)amide, amino optionally mono- or di-substituted with $C_{1-6}$ alkyl; and $R_5$ is H or methyl, such that B is for example:

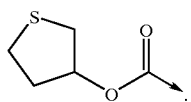

or $R_4$ is preferably (iii) amino optionally mono- or di-substituted with $C_{1-3}$ alkyl, such that B is for example:

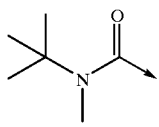

or $R_4$ is preferably (iv) $C_6$ or $C_{10}$ aryl or $C_{7-16}$ aralkyl, all optionally substituted with $C_{1-6}$ alkyl, hydroxy, amino or amido optionally substituted with $C_{1-6}$ alkyl; or (v) Het optionally substituted with $C_{1-6}$ alkyl, hydroxy, amino or amido, such that B is for example:

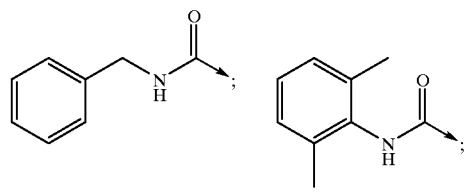

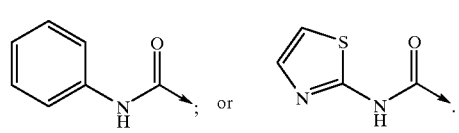

Alternatively, B is more preferably a thioamide of formula $R_4$—NH—C(S)—; wherein $R_4$ is preferably $R_4$ is (i) $C_{1-10}$ alkyl; or (ii) $C_{3-7}$ cycloalkyl, such that B is for example:

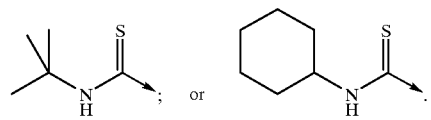

Most preferably, B is an amide of formula $R_4$—NH—C(O)— wherein $R_4$ is preferably (i) $C_{1-10}$ alkyl optionally substituted with carboxyl, $C_{1-6}$ alkanoyl, hydroxy, $C_{1-6}$ alkoxy amido, (lower alkyl) amide, amino optionally mono- or di-substituted with $C_{1-6}$ alkyl;

(ii) $C_{3-7}$ cycloalkyl or $C_{4-10}$ alkylcycloalkyl, all optionally substituted with carboxyl, ($C_{1-6}$ alkoxy)carbonyl, amido, (lower alkyl)amide, amino optionally mono- or di-substituted with $C_{1-6}$ alkyl;

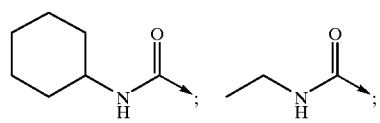

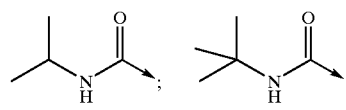

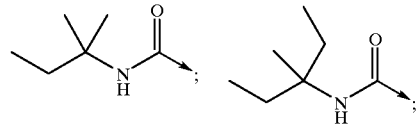

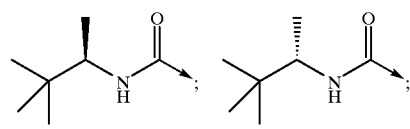

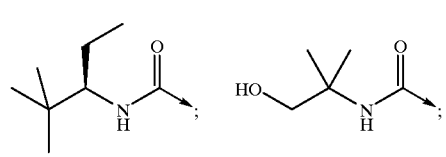

-continued

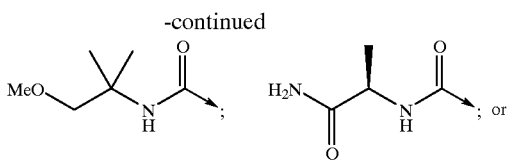
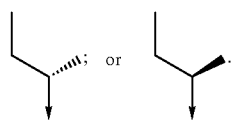

or $R_4$ is preferably (iv) $C_6$ or $C_{10}$ aryl or $C_{7-16}$ aralkyl optionally substituted with $C_{1-6}$ alkyl, hydroxy, amino or amido, such that B is for example:

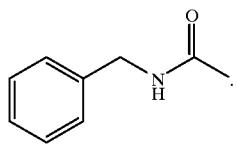

Even most preferably, B is tert-butoxycarbonyl (Boc) or

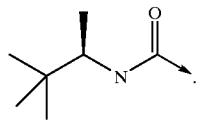

Preferably, Y is H or methyl. More preferably, Y is H.

Preferably, $R^3$ is $C_{1-8}$ alkyl, $C_{3-7}$ cycloalkyl, or $C_{4-10}$ alkylcycloalkyl, all optionally substituted with hydroxy, $C_{1-6}$ alkoxy, $C_{1-6}$ thioalkyl, acetamido, $C_6$ or $C_{10}$ aryl, or $C_{7-16}$ aralkyl, such that B is for example:

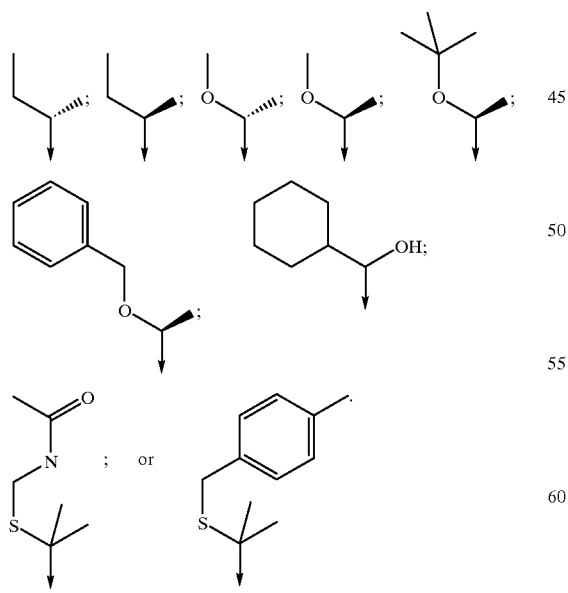

More preferably, $R^3$ is the side chain of tert-butylglycine (Tbg), Ile, Val, Chg or Most preferably, $R^3$ is the side chain of Tbg, Chg or Val.

Included within the scope of the invention are compounds of formula I wherein, preferably, $R^2$ is S—$R_{20}$ or O—$R_{20}$ wherein $R_{20}$ is preferably a $C_6$ or $C_{10}$ aryl, $C_{7-16}$ aralkyl, Het or —$CH_2$—Het, all optionally mono-, di- or tri-substituted with $R_{21}$.

Preferably, $R_{21}$ is $C_{1-6}$ alkyl; $C_{1-6}$ alkoxy; lower thioalkyl; amino or amido optionally mono-or di-substituted with $C_{1-6}$ alkyl, $C_6$ or $C_{10}$ aryl, $C_{7-16}$ aralkyl, Het or (lower alkyl)-Het; $NO_2$; OH; halo; trifluoromethyl; catboxyl; $C_6$ or $C_{10}$ aryl, $C_{7-16}$ aralkyl, or Het, said aryl, aralkyl or Het being optionally substituted with $R_{22}$. More preferably, $R_{21}$ is $C_{1-6}$ alkyl; $C_{1-6}$alkoxy; amino; di(lower alkyl)amino; (lower alkyl)amide; $C_6$ or $C_{10}$ aryl, or Het, said aryl or Het being optionally substituted with $R_{22}$.

Preferably, $R_{22}$ is $C_{1-6}$ alkyl; $C_{3-7}$ cycloalkyl; $C_{1-6}$ alkoxy; amino; mono- or di-(lower alkyl)amino; (lower alkyl)amide; sulfonylalkyl; $NO_2$; OH; halo; trifluoromethyl; carboxyl or Het. More preferably, $R_{22}$ is $C_{1-6}$ alkyl; $C_{3-7}$ cycloalkyl; $C_{1-6}$ alkoxy; amino; mono- or di(lower alkyl)amino; amido; (lower alkyl)amide; halo; trifluoromethyl or Het. Most preferably, $R_{22}$ is $C_{1-6}$ alkyl; $C_{1-6}$ alkoxy; halo; amino optionally mono- or di-substituted with lower alkyl; amido; (lower alkyl)amide; or Het. Even most preferably, $R_{22}$ is methyl; ethyl; isopropyl; tert-butyl; methoxy; chloro; amino optionally mono- or di-substituted with lower alkyl; amido, (lower alkyl) amide; or (lower alkyl) 2-thiazole.

Alternatively, $R^2$ is preferably selected from the group consisting of:

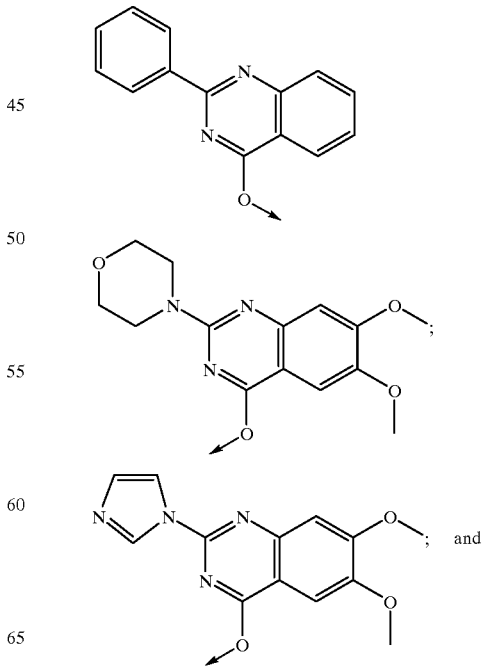

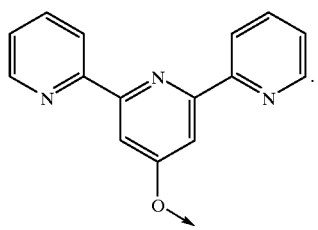

More preferably, $R^2$ is 1-naphthylmethoxy; 2-naphthylmethoxy; benzyloxy, 1-naphthyloxy; 2-naphthyloxy; or quinolinoxy unsubstituted, mono- or di-substituted with $R_{21}$ as defined above. Most preferably, $R^2$ is 1-naphtylmethoxy, or quinolinoxy unsubstituted, mono- or di-substituted with $R_{21}$ as defined above, such that $R^2$ is for example:

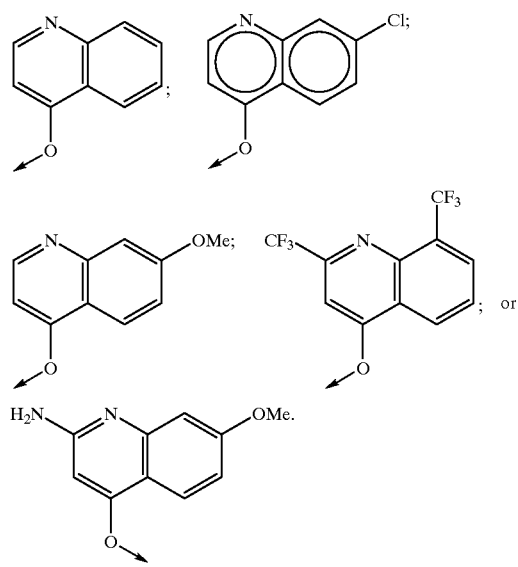

Still, more preferably, $R^2$ is:

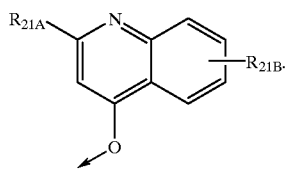

More preferably, $R_{21A}$ is $C_{1-6}$ alkyl such as isopropyl, tert-butyl or cyclohexyl; $C_{1-6}$ alkoxy such as methoxy,

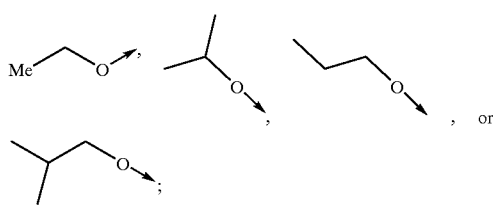

lower thioalkyl such as

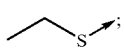

halo such as chloro;

amino optionally mono-substituted with $C_{1-6}$ alkyl; or $C_6$ or $C_{10}$ aryl, such that $R_{21A}$ is for example: dimethylamino, Ph—N(Me)—;

unsubstituted $C_6$ or $C_{10}$ aryl, $C_{7-16}$ aralkyl, such as for example phenyl or

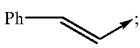

or $R_{21A}$ is more preferably Het optionally substituted with $R_{22}$ wherein $R_{22}$ is $C_{1-6}$ alkyl, $C_{1-6}$ alkoxy, amido, (lower alkyl)amide, amino optionally mono- or di-substituted with $C_{1-6}$ alkyl, or Het, such that $R_{21A}$ is for example:

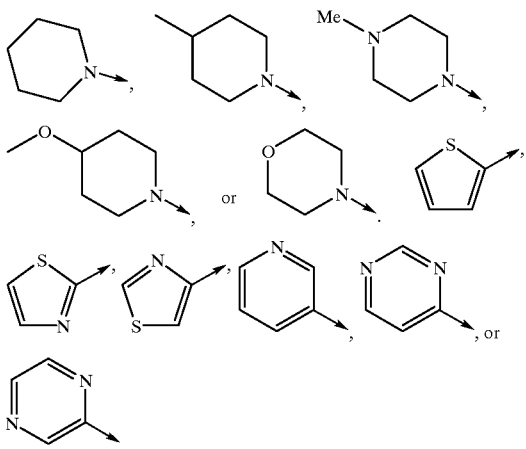

Most preferably, $R_{21A}$ is $C_6$, $C_{10}$ aryl or Het, all optionally substituted with $R_{22}$ as defined above, such that $R_{21A}$ is for example:

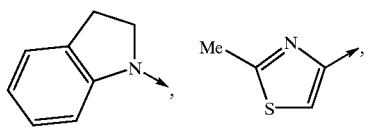

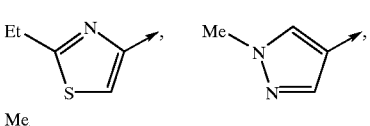

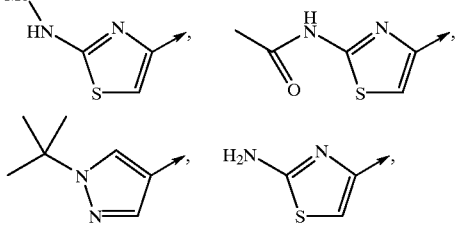

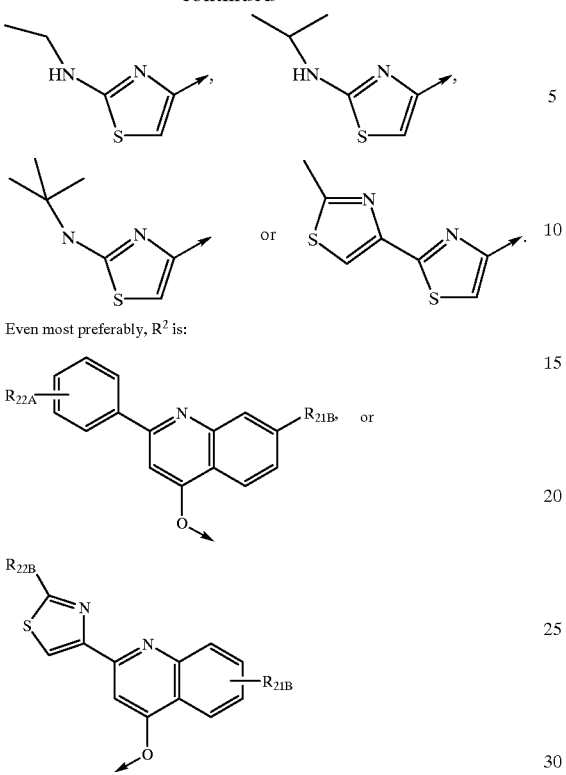

Even most preferably, R² is:

wherein R$_{22A}$ is preferably C$_{1-6}$ alkyl (such as methyl); C$_{1-6}$ alkoxy (such as methoxy); or halo (such as chloro); R$_{22B}$ is preferably C$_{1-6}$ alkyl, amino optionally mono-substituted with C$_{1-6}$ alkyl, amido; or (lower alkyl)amide; and R$_{21B}$ is preferably C$_{1-6}$ alkyl, C$_{1-6}$ alkoxy, amino, di(lower alkyl)amino, (lower alkyl)amide, NO$_2$, OH, halo, trifluoromethyl, or carboxyl. More preferably, R$_{21B}$ is C$_{1-6}$ alkoxy, or di(lower alkyl)amino. Most preferably, R$_{21B}$ is methoxy.

As described hereinabove the P1 segment of the compounds of formula I is a cyclobutyl or cyclopropyl ring, both optionally substituted with R$^1$.

Preferably, R$^1$ is H, C$_{1-3}$ alkyl, C$_{3-5}$ cycloalkyl, or C$_{2-4}$ alkenyl optionally substituted with halo. More preferably R$^1$ is ethyl, vinyl, cyclopropyl, 1 or 2-bromoethyl or 1 or 2-bromovinyl. Most preferably, R$^1$ is vinyl.

When R$^1$ is not H, then P1 is preferably a cyclopropyl system of formula:

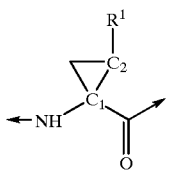

wherein C$_1$ and C$_2$ each represent an asymmetric carbon atom at positions 1 and 2 of the cyclopropyl ring. Not withstanding other possible asymmetric centers at other segments of the compounds of formula I, the presence of these two asymmetric centers means that the compounds of formula I can exist as racemic mixtures of diastereoisomers. As illustrated in the examples hereinafter, the racemic mixtures can be prepared and thereafter separated into individual optical isomers, or these optical isomers can be prepared by chiral synthesis.

Hence, the compound of formula I can exist as a racemic mixture of diastereoisomers at carbon 1 but wherein R$^1$ at carbon 2 is orientated syn to the carbonyl at position 1, represented by the radical:

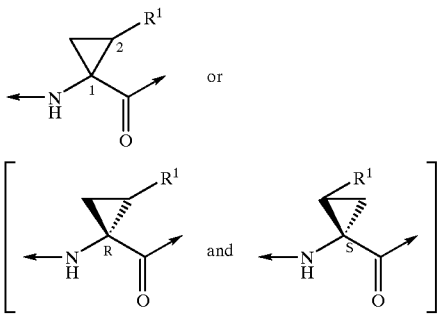

or the compound of formula I can exist as a racemic mixture of diastereoisomers wherein R$^1$ at position 2 is orientated anti to the carbonyl at position 1, represented by the radical:

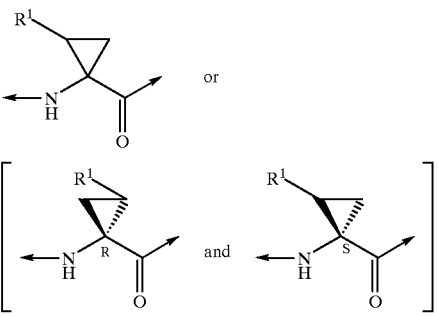

In turn, the racemic mixtures can be separated into individual optical isomers. A most interesting finding of this invention pertains to the addition of a R$^1$ substituent on the carbon 2 as well as the spatial orientation of the P1 segment. The finding concerns the configuration of the asymmetric carbon 1. A preferred embodiment is one wherein R$^1$ is not H and carbon 1 has the R configuration.

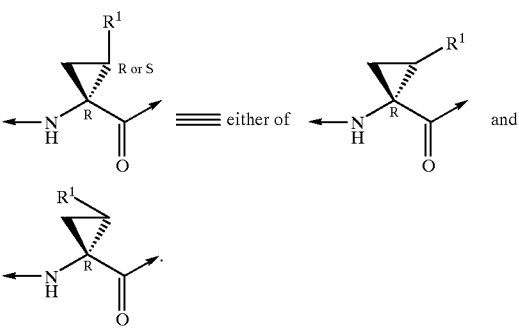

More explicitly, the introduction of a substituent (R$^1$) at C2 has an impact on the potency when R$^1$ is introduced in a way that C1 has the R configuration. For example compounds 901 (1R,2S) and 203 (1R,2R) have activities of 25 and 82 nM respectively. When compared to the unsubstituted cyclopropyl compound 111 (475 nM), a substantial increase in potency is observed. Moreover, as shown for compounds 901 and 203, when carbon 1 has the R configuration, HCV NS3 protease inhibition is further enhanced by the configuration of the substituent $R^1$ (e.g. alkyl or alkylene) at carbon 2 of the cyclopropyl ring, e.g. the compound that possesses $R^1$ "syn" to the carboxyl has greater potency (25 nM) than the "anti" enantiomer (82 nM). We can see the effect of the R vs. S configuration at the C1 by comparing compounds 801 (1R,2S) and its corresponding (1S,2S) isomer which have potencies of 6 nM and >10 $\mu$M respectively, a difference of over 1500 fold!! Therefore a most preferred compound is an optical isomer having the $R^1$ substituent and the carbonyl in a syn orientation in the following absolute configuration:

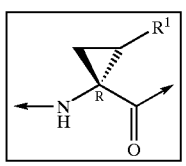

In the case where $R^1$ is ethyl, for example, the asymmetric carbon atoms at positions 1 and 2 have the R,R configuration.

Included within the scope of this invention are compounds of formula I wherein

B is a $C_6$ or $C_{10}$ aryl or $C_{7-16}$ aralkyl, all optionally substituted with $C_{1-6}$ alkyl, $C_{1-6}$ alkoxy, $C_{1-6}$ alkanoyl, hydroxy, hydroxyalkyl, halo, haloalkyl, nitro, cyano, cyanoalkyl, amido, (lower alkyl)amido, or amino optionally substituted with $C_{1-6}$ alkyl; or Het or (lower alkyl)-Het, all optionally substituted with $C_{1-6}$ alkyl, $C_{1-6}$ alkoxy, $C_{1-6}$ alkanoyl, hydroxy, hydroxyalkyl, halo, haloalkyl, nitro, cyano, cyanoalkyl, amido, (lower alkyl)amido, or amino optionally substituted with $C_{1-6}$ alkyl, or B is $R_4$—$SO_2$ wherein $R_4$ is preferably amido; (lower alkyl)amide; $C_6$ or $C_{10}$ aryl, $C_{7-14}$ aralkyl or Het, all optionally substituted with $C_{1-6}$ alkyl, or B is an acyl derivative of formula $R_4$—C(O)— wherein $R_4$ is
(i) $C_{1-10}$ alkyl optionally substituted with carboxyl, hydroxy or $C_{1-6}$ alkoxy, amido, (lower alkyl)amide, or amino optionally mono- or di-substituted with $C_{1-6}$ alkyl;
(ii) $C_{3-7}$ cycloalkyl or $C_{4-10}$ alkylcycloalkyl, both optionally substituted with hydroxy, carboxyl, ($C_{1-6}$ alkoxy)carbonyl, amido, (lower alkyl)amide, or amino optionally mono- or di-substituted with $C_{1-6}$ alkyl;
(iv) $C_6$ or $C_{10}$ aryl or $C_{7-16}$ aralkyl, all optionally substituted with $C_{1-6}$ alkyl, hydroxy, amido, (lower alkyl)amide, or amino optionally substituted with $C_{1-6}$ alkyl;
(v) Het or (lower alkyl)-Het, both optionally substituted with $C_{1-6}$ alkyl, hydroxy, amino optionally substituted with $C_{1-6}$ alkyl, or B is an carboxyl of formula $R_4$—O—C(O)—, wherein $R_4$ is
(i) $C_{1-10}$ alkyl optionally substituted with carboxyl, $C_{1-6}$ alkanoyl, hydroxy, $C_{1-6}$ alkoxy, amino, optionally mono- or di-substituted with $C_{1-6}$ alkyl, amido or (lower alkyl)amide;
(ii) $C_{3-7}$ cycloalkyl, $C_{4-10}$ alkylcycloalkyl, all optionally substituted with carboxyl, ($C_{1-6}$ alkoxy) carbonyl, amino optionally mono- or di-substituted with $C_{1-6}$ alkyl, amido or (lower alkyl)amide;
(iv) $C_6$ or $C_{10}$ aryl or $C_{7-16}$ aralkyl optionally substituted with $C_{1-6}$ alkyl, hydroxy, amido, (lower alkyl) amide, or amino optionally mono- or di-substituted with $C_{1-6}$ alkyl; or
(v) Het or (lower alkyl)-Het, both optionally substituted with $C_{1-6}$ alkyl, hydroxy, amino optionally mono- or di-substituted with $C_{1-6}$ alkyl, amido or (lower alkyl) amido, or B is an amide of formula $R_4$—N($R_5$)—C(O)— wherein $R_4$ is
(i) $C_{1-10}$ alkyl optionally substituted with carboxyl, $C_{1-6}$ alkanoyl, hydroxy, $C_{1-6}$ alkoxy, amido, (lower alkyl)amido, or amino optionally mono- or di-substituted with $C_{1-6}$ alkyl;
(ii) $C_{3-7}$ cycloalkyl or $C_{4-10}$ alkylcycloalkyl, all optionally substituted with carboxyl, ($C_{1-6}$ alkoxy) carbonyl, amido, (lower alkyl)amido, or amino optionally mono- or di-substituted with $C_{1-6}$ alkyl;
(iii) amino optionally mono- or di-substituted with $C_{1-3}$ alkyl;
(iv) $C_6$ or $C_{10}$ aryl or $C_{7-16}$ aralkyl, all optionally substituted with $C_{1-6}$ alkyl, hydroxy, amido, (lower alkyl)amide, or amino optionally substituted with $C_{1-6}$ alkyl; or
(v) Het or (lower alkyl)-Het, both optionally substituted with $C_{1-6}$ alkyl, hydroxy, amino optionally substituted with $C_{1-6}$ alkyl, amido or (lower alkyl)amide; and $R_5$ is preferably H or methyl, or B is thioamide of formula $R_4$—NH—C(S)—; wherein $R_4$ is
(i) $C_{1-10}$ alkyl optionally substituted with carboxyl, $C_{1-6}$ alkanoyl or $C_{1-6}$ alkoxy;
(ii) $C_{3-7}$ cycloalkyl or $C_{4-10}$ alkylcycloalkyl, all optionally substituted with carboxyl, ($C_{1-6}$ alkoxy) carbonyl, amino or amido;

Y is H or methyl;

$R^3$ is $C_{1-8}$ alkyl, $C_{3-7}$ cycloalkyl, or $C_{4-10}$ alkylcycloalkyl, all optionally substituted with hydroxy, $C_{1-6}$ alkoxy, $C_{1-6}$ thioalkyl, acetamido, $C_6$ or $C_{10}$ aryl, or $C_{7-16}$ aralkyl;

$R^2$ is S—$R_{20}$ or O—$R_{20}$ wherein $R_{20}$ is preferably a $C_6$ or $C_{10}$ aryl, $C_{7-16}$ aralkyl, Het or —$CH_2$-Het, all optionally mono-, di- or tri-substituted with $R_{21}$, wherein $R_{21}$ is $C_{1-6}$ alkyl; $C_{1-6}$ alkoxy; lower thioalkyl; amino or amido optionally mono- or di-substituted with $C_{1-6}$ alkyl, $C_6$ or $C_{10}$ aryl, $C_{7-16}$ aralkyl, Het or (lower alkyl)-Het; $NO_2$; OH; halo; trifluoromethyl; carboxyl; $C_6$ or $C_{10}$ aryl, $C_{7-16}$ aralkyl, or Het, said aryl, aralkyl or Het being optionally substituted with $R_{22}$, wherein $R_{22}$ is $C_{1-6}$ alkyl; $C_{3-7}$ cycloalkyl; $C_{1-6}$ alkoxy; amino; mono- or di-(lower alkyl)amino; (lower alkyl)amide; sulfonylalkyl; $NO_2$; OH; halo; trifluoromethyl; carboxyl or Het; or $R_2$ is selected from the group consisting of:

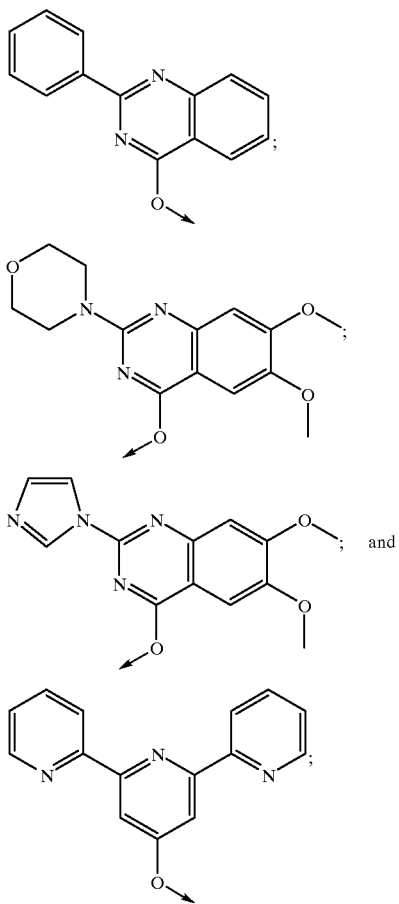

or $R_2$ is 1-naphthylmethoxy; 2-naphthylmethoxy; benzyloxy, 1-naphthyloxy; 2-naphthyloxy; or quinolinoxy unsubstituted, mono- or di-substituted with $R_{21}$ as defined above;

the P1 segment is a cyclobutyl or cyclopropyl ring, both optionally substituted with $R^1$, wherein $R^1$ is H, $C_{1-3}$ alkyl, $C_{3-5}$ cycloalkyl, or $C_{2-4}$ alkenyl optionally substituted with halo, and said $R^1$ at carbon 2 is orientated syn to the carbonyl at position 1, represented by the radical:

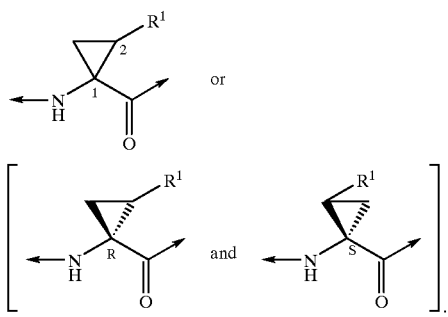

Included within the scope of this invention are compounds of formula I wherein

B is a $C_6$ or $C_{10}$ aryl optionally substituted with $C_{1-6}$ alkyl, $C_{1-6}$ alkoxy, $C_{1-6}$ alkanoyl, hydroxy, hydroxyalkyl, halo, haloalkyl, nitro, cyano, cyanoalkyl, amido, (lower alkyl)amide, or amino optionally mono- or di-substituted with $C_{1-6}$ alkyl; or B is Het optionally substituted with $C_{1-6}$ alkyl, $C_{1-6}$ alkoxy, $C_{1-6}$ alkanoyl, hydroxy, halo, amido, (lower alkyl)amide, or amino optionally mono- or di-substituted with $C_{1-6}$ alkyl; or B is $R_4$—$SO_2$ wherein $R_4$ is $C_6$ or $C_{10}$ aryl, a $C_{7-14}$ aralkyl or Het all optionally substituted with $C_{1-6}$ alkyl; amido, (lower alkyl)amide; or B is an acyl derivative of formula $R_4$—C(O)— wherein $R_4$ is (i) $C_{1-10}$ alkyl optionally substituted with carboxyl, hydroxy or $C_{1-6}$ alkoxy; or (ii) $C_{3-7}$ cycloalkyl or $C_{4-10}$ alkylcycloalkyl, both optionally substituted with hydroxy, carboxyl, ($C_{1-6}$ alkoxy)carbonyl; or (iv) $C_6$ or $C_{10}$ aryl or $C_{7-16}$ aralkyl, all optionally substituted with $C_{1-6}$ alkyl, hydroxy; or (v) Het optionally substituted with $C_{1-6}$ alkyl, hydroxy, amido or amino;

or B is a carboxyl of formula $R_4$—O—C(O)—, wherein $R_4$ is (i) $C_{1-10}$ alkyl optionally substituted with carboxyl, $C_{1-6}$ alkanoyl, hydroxy, $C_{1-6}$ alkoxy or amido, (lower alkyl)amide, amino optionally mono- or di-substituted with $C_{1-6}$ alkyl;

(ii) $C_{3-7}$ cycloalkyl, $C_{4-10}$ alkylcycloalkyl, all optionally substituted with carboxyl, ($C_{1-6}$ alkoxy) carbonyl, amido, (lower alkyl)amide, amino optionally mono- or di-substituted with $C_{1-6}$ alkyl; or (iv) $C_6$ or $C_{10}$ aryl or $C_{7-16}$ aralkyl, all optionally substituted with $C_{1-6}$ alkyl, hydroxy, amino optionally substituted with $C_{1-6}$ alkyl; or (v) Het or (lower alkyl)-Het, both optionally substituted with $C_{1-6}$ alkyl, hydroxy, amido, or amino optionally mono-substituted with $C_{1-6}$ alkyl;

or B is an amide of formula $R_4$—N($R_5$)—C(O)— wherein $R_4$ is (i) $C_{1-10}$ alkyl optionally substituted with carboxyl, $C_{1-6}$ alkanoyl, hydroxy, $C_{1-6}$ alkoxy, amido, (lower alkyl)amide, amino optionally mono- or di-substituted with $C_{1-6}$ alkyl;

(ii) $C_{3-7}$ cycloalkyl or $C_{4-10}$ alkylcycloalkyl, all optionally substituted with carboxyl, ($C_{1-6}$ alkoxy) carbonyl, amido, (lower alkyl)amide, amino optionally mono- or di-substituted with $C_{1-6}$ alkyl; and $R_5$ is H or methyl; or $R_4$ is (iii) amino optionally mono- or di-substituted with $C_{1-3}$ alkyl; or (iv) $C_6$ or $C_{10}$ aryl or $C_{7-16}$ aralkyl, all optionally substituted with $C_{1-6}$ alkyl, hydroxy, amino or amido optionally substituted with $C_{1-6}$ alkyl; or (v) Het optionally substituted with $C_{1-6}$ alkyl, hydroxy, amino or amido; or B is a thioamide of formula $R_4$—NH—C(S)—; wherein $R_4$ is:

(i) $C_{1-10}$ alkyl; or (ii) $C_{3-7}$ cycloalkyl; or

B is an amide of formula $R_4$—NH—C(O)— wherein $R_4$ is i) $C_{1-10}$ alkyl optionally substituted with carboxyl, $C_{1-6}$ alkanoyl, hydroxy, $C_{1-6}$ alkoxy amido, (lower alkyl) amide, amino optionally mono- or di-substituted with $C_{1-6}$ alkyl;

(ii) $C_{3-7}$ cycloalkyl or $C_{4-10}$ alkylcycloalkyl, all optionally substituted with carboxyl, ($C_{1-6}$ alkoxy) carbonyl, amido, (lower alkyl)amide, amino optionally mono- or di-substituted with $C_{1-6}$ alkyl;

(iv) $C_6$ or $C_{10}$ aryl or $C_{7-16}$ aralkyl optionally substituted with $C_{1-6}$ alkyl, hydroxy, amino or amido;

Y is H;

R³ is the side chain of tert-butylglycine (Tbg), Ile, Val, Chg or;

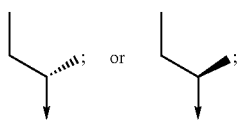

R² is 1-naphtylmethoxy; or quinolinoxy unsubstituted, mono- or di-substituted with R$_{21}$ as defined above, or R² is:

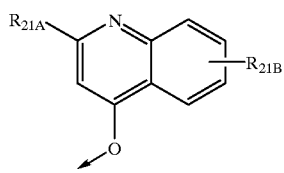

wherein R$_{21A}$ is C$_{1-6}$ alkyl; C$_{1-6}$ alkoxy; C$_6$, C$_{10}$ aryl or Het; lower thioalkyl; halo; amino optionally mono-substituted with C$_{1-6}$ alkyl; or C$_6$, C$_{10}$ aryl, C$_{7-16}$ aralkyl or Het, optionally substituted with R$_{22}$ wherein R$_{22}$ is C$_{1-6}$ alkyl, C$_{1-6}$ alkoxy, amido, (lower alkyl)amide, amino optionally mono- or di-substituted with C$_{1-6}$ alkyl, or Het;

P1 is a cyclopropyl ring wherein carbon 1 has the R configuration,

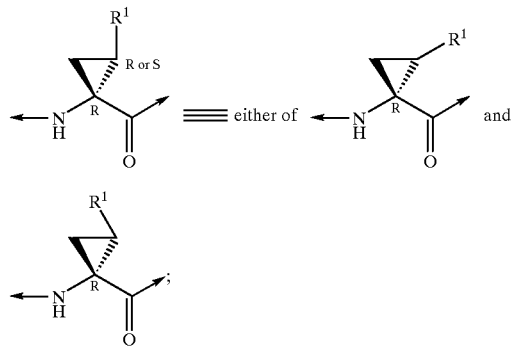

and R¹ is ethyl, vinyl, cyclopropyl, 1 or 2-bromoethyl or 1 or 2-bromovinyl.

Further included in the scope of the invention are compounds of formula I wherein:

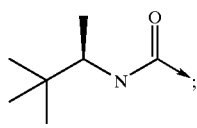

B is tert-butoxycarbonyl (Boc) or

R³ is the side chain of Tbg, Chg or Val;

R²:

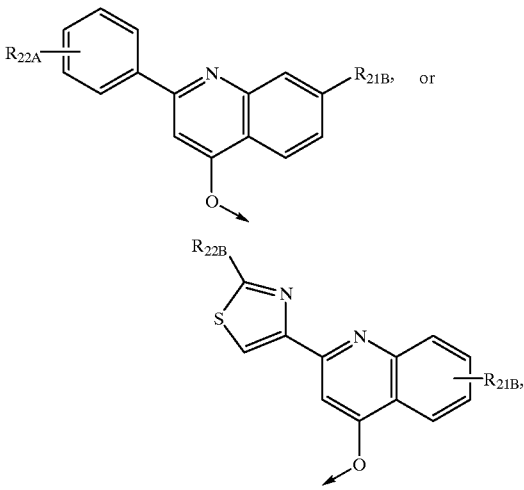

wherein R$_{22A}$ is C$_{1-6}$ alkyl (such as methyl); C$_{1-6}$ alkoxy (such as methoxy); or halo (such as chloro); R$_{22B}$ is C$_{1-6}$ alkyl, amino optionally mono-substituted with C$_{1-6}$ alkyl, amido, or (lower alkyl) amide; and R$_{21B}$ is C$_{1-6}$ alkyl, C$_{1-6}$ alkoxy, amino, di(lower alkyl)amino, (lower alkyl)amide, NO$_2$, OH, halo, trifluoromethyl, or carboxyl;

and P1 is:

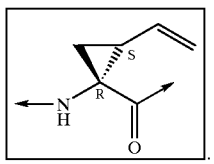

Finally, included within the scope of this invention is each compound of formula I as presented in Tables 1 to 10.

According to an alternate embodiment, the pharmaceutical compositions of this invention may additionally comprise another anti-HCV agent. Examples of anti-HCV agents include, α- or β-interferon, ribavirin and amantadine.

According to another alternate embodiment, the pharmaceutical compositions of this invention may additionally comprise other inhibitors of HCV protease.

According to yet another alternate embodiment, the pharmaceutical compositions of this invention may additionally comprise an inhibitor of other targets in the HCV life cycle, including but not limited to, helicase, polymerase, metalloprotease or internal ribosome entry site (IRES).

The pharmaceutical compositions of this invention may be administered orally, parenterally or via an implanted reservoir. Oral administration or administration by injection is preferred. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of formula I and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV NS3 protease or to treat or prevent HCV virus infection. Such treatment may also be achieved using the compounds of this invention in combination with agents which include, but are not limited to: immunomodulatory agents, such as α-, β-, or γ-interferons; other antiviral agents such as ribavirin, amantadine; other inhibitors of HCV NS3 protease; inhibitors of other targets in the HCV life cycle, which include but not limited to, helicase, polymerase, metalloprotease, or internal ribosome entry site (IRES); or combinations thereof. The additional agents may be combined with the compounds of this invention to create a single dosage form. Alternatively these additional agents may be separately administered to a mammal as part of a multiple dosage form.

Accordingly, another embodiment of this invention provides methods of inhibiting HCV NS3 protease activity in mammals by administering a compound of the formula I, wherein the substituents are as defined above.

In a preferred embodiment, these methods are useful in decreasing HCV NS3 protease activity in a mammal. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle such as helicase, polymerase, or metallo protease or IRES. Such additional agent may be administered to the mammal prior to, concurrently with, or following the administration of the compositions of this invention.

In an alternate preferred embodiment, these methods are useful for inhibiting viral replication in a mammal. Such methods are useful in treating or preventing HCV disease. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle. Such additional agent may be administered to the mammal prior to, concurrently with, or following the administration of the composition according to this invention.

The compounds set forth herein may also be used as laboratory reagents. The compounds of this invention may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

The compounds set forth herein may also be used as research reagents. The compounds of this invention may also be used as positive control to validate surrogate cell-based assays or in vitro or in vivo viral replication assays.

Process

The compounds of the present invention were synthesized according to a general process as illustrated in scheme I (wherein CPG is a carboxyl protecting group and APG is an amino pretecting group):

SCHEME I

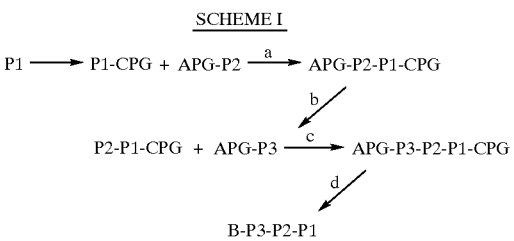

Briefly, the P1, P2, and P3 can be linked by well known peptide coupling techniques. The P1, P2, and P3 groups may be linked together in any order as long as the final compound corresponds to peptides of Formula I. For example, P3 can be linked to P2-P1; or P1 linked to P3-P2.

Generally, peptides are elongated by deprotecting the α-amino group of the N-terminal residue and coupling the unprotected carboxyl group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme I, or by solid phase peptide synthesis according to the method originally described in Merrifield, J. Am. Chem. Soc., (1963), 85, 2149–2154, the disclosure of which is hereby incorporated by reference. Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyidiimidazole method, phosphorus reagents or oxidation-reduction methods. Some of these methods (especially the carbodiimide method) can be enhanced by adding 1-hydroxybenzotriazole. These coupling reactions can be performed in either solution (liquid phase) or solid phase.

More explicitly, the coupling step involves the dehydrative coupling of a free carboxyl of one reactant with the free amino group of the other reactant in the presence of a coupling agent to form a linking amide bond. Descriptions of such coupling agents are found in general textbooks on peptide chemistry, for example, M. Bodanszky, "Peptide Chemistry", $2^{nd}$ rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)phosphonium hexafluorophosphate, either by itself or in the presence of 1-hydroxybenzotriazole. Another practical and useful coupling agent is commercially available 2-(1H-benzotriazol-1-yl)-N,N,N',N'-tetramethyluronium tetrafluoroborate. Still another practical and useful coupling agent is commercially available O-(7-azabenzotriazol-1-yl)-N,N,N',N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine or N-methylpyrrolidine, is added to maintain the reaction mixture at a pH of about 8. The reaction temperature usually ranges between 0° C. and 50° C. and the reaction time usually ranges between 15 min and 24 h.

When a solid phase synthetic approach is employed, the C-terminal carboxylic acid is attached to an insoluble carrier (usually polystyrene). These insoluble carriers contain a group that will react with the carboxylic group to form a bond that is stable to the elongation conditions but readily cleaved later. Examples of which are: chloro- or bromomethyl resin, hydroxymethyl resin, trytil resin and 2-methoxy-4-alkoxy-benzylaloconol resin.

Many of these resins are commercially available with the desired C-terminal amino acid already incorporated. Alternatively, the amino acid can be incorporated on the solid support by known methods (Wang, S.-S., J. Am. Chem. Soc., (1973), 95, 1328; Atherton, E.; Shepard, R. C. "Solid-phase peptide synthesis; a practical approach" IRL Press: Oxford, (1989); 131–148). In addition to the foregoing, other methods of peptide synthesis are described in Stewart and Young, "Solid Phase Peptide Synthesis", $2^{nd}$ ed., Pierce Chemical Co., Rockford, Ill. (1984); Gross, Meienhofer, Udenfriend, Eds., "The Peptides: Analysis, Synthesis, Biology", Vol. 1, 2, 3, 5, and 9, Academic Press, New-York, (1980–1987); Bodansky et al., "The Practice of Peptide Synthesis" Springer-Verlag, New-York (1984), the disclosures of which are hereby incorporated by reference.

The functional groups of the constituent amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

The α-carboxyl group of the C-terminal residue is usually protected as an ester (CPG) that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

The α-amino group of each amino acid to be coupled to the growing peptide chain must be protected (APG). Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl. The preferred α-amino protecting group is either Boc or Fmoc. Many amino acid derivatives suitably protected for peptide synthesis are commercially available.

The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (RT) usually 20–22° C.

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the α-amino protecting group, the following side chain protecting group are suitable: p-toluenesulfonyl (tosyl) moieties can be used to protect the amino side chain of amino acids such as Lys and Arg; acetamidomethyl, benzyl (Bn), or t-butylsulfonyl moieties can be used to protect the sulfide containing side chain of cysteine; benzyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenylmethyl (Trityl) moiety can be used to protect the sulfide containing side chain of cysteine.

Once the elongation of the peptide is completed all of the protecting groups are removed. When a liquid phase synthesis is used, the protecting groups are removed in whatever manner is dictated by the choice of protecting groups. These procedures are well known to those skilled in the art.

When a solid phase synthesis is used, the peptide is cleaved from the resin simultaneously with the removal of the protecting groups. When the Boc protection method is used in the synthesis, treatment with anhydrous HF containing additives such as dimethyl sulfide, anisole, thioanisole, or p-cresol at 0° C. is the preferred method for cleaving the peptide from the resin. The cleavage of the peptide can also be accomplished by other acid reagents such as trifluoromethanesulfonic acid/trifluoroacetic acid mixtures. If the Fmoc protection method is used, the N-terminal Fmoc group is cleaved with reagents described earlier. The other protecting groups and the peptide are cleaved from the resin using solution of trifluoroacetic acid and various additives such as anisole, etc.

1. Synthesis of Capping Group B

Different capping groups B are introduced in the following manner 1.1) When B is an aryl, aralkyl: the arylated amino acids were prepared by one of the three methods below:

a) Direct nucleophilic displacement on a fluoro-nitro aryl moiety:

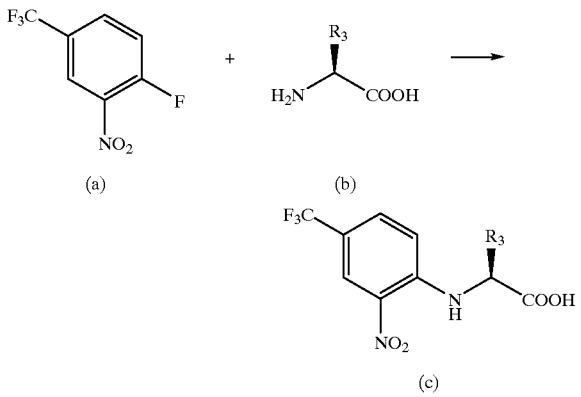

Briefly, 4-fluoro-3-nitrobenzotrifluoride (a) was reacted with L-amino acid (b) in the presence of a base such as potassium carbonate at 80° C. to yield the desired N-aryl amino acid (c);

b) Copper catalyzed couplings according to Ma et al. (*J. Am. Chem. Soc.* 1998, 120, 12459–12467):

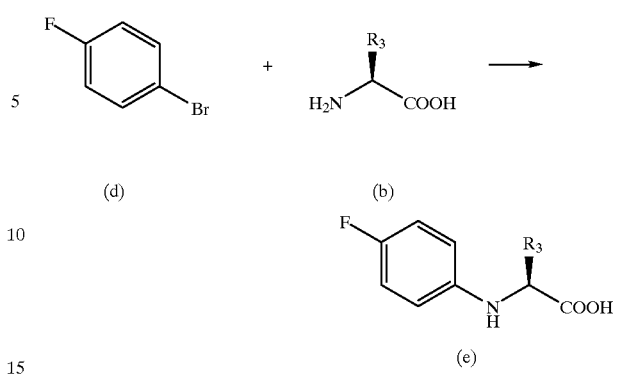

Briefly, bromo-4-fluorobenzene (d) was reacted with L-amino acid (b) in the presence of a base such as potassium carbonate and a catalytic amount of copper iodide at 90° C. to yield the desired N-aryl amino acid (e); or c) Nucleophilic displacement of a triflate by an aniline:

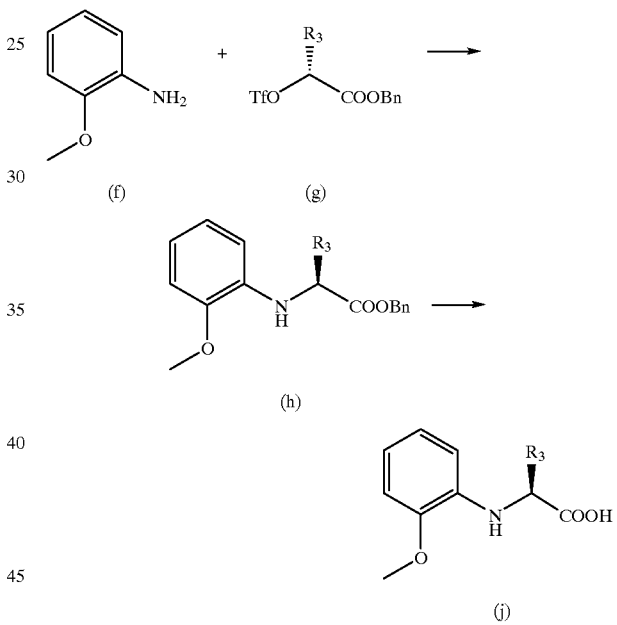

Briefly, o-anisidine (f) was reacted with triflate (g) in the presence of a base such as 2,6-lutidine at 90° C. to give benzyl ester (h). Hydrogenation with 10% Pd/C yielded the desired N-aryl amino acid (i).

1.2) When B is an aminothiazole derivative:

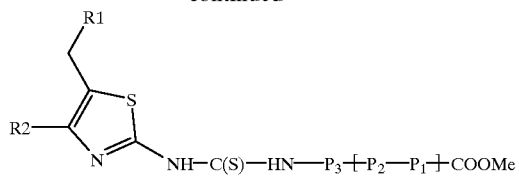

a) The Fmoc-thiocyanate prepared according to Kearney et al., 1998, J. Org. Chem, 63, 196, was reacted with a protected P3 residue or the whole peptide or a peptide segment to provide the thiourea.

b) The thiourea derivative is reacted with an appropriate bromoketone to provide the corresponding thiazole derivative.

1.3) When B is $R_4$—C(O)—, $R_4$—S(O)$_2$:

Protected P3 or the whole peptide or a peptide segment is coupled to an appropriate acyl chloride or sulfonyl chloride respectively, that is either commercially available or for which the synthesis is well known in the art.

1.4) When B is $R_4O$—C(O)—:

Protected P3 or the whole peptide or a peptide segment is coupled to an appropriate chloroformate that is either commercially available or for which the synthesis is well known in the art. For Boc-derivatives (Boc)$_2$O is used.

For example:

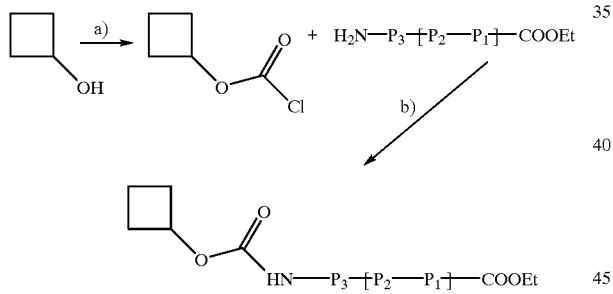

a) Cyclobutanol is treated with phosgene to furnish the corresponding chloroformate.

b) The chloroformate is treated with the desired NH$_2$-tripeptide in the presence of a base such as triethylamine to afford the cyclobutylcarbamate.

1.5) When B is $R_4$—N($R_5$)—C(O)—, or $R_4$—NH—C(S)—, protected P3 or the whole peptide or a peptide segment is treated with phosgene followed by amine as described in SynLett. Feb. 1995; (2); 142–144

2. Synthesis of P2 Moieties 2.1 Synthesis of Precursors

A) Synthesis of Haloarylmethane Derivatives

The preparation of halomethyl-8-quinoline IId was done according to the procedure of K. N. Campbell et al., J. Amer. Chem. Soc., (1946), 68, 1844.

SCHEME II

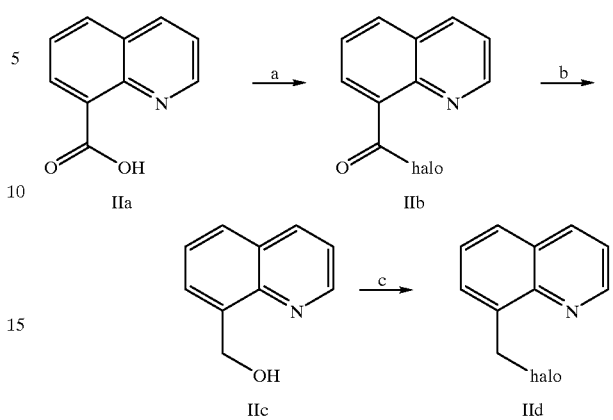

Briefly, 8-quinoline carboxylic acid IIa was converted to the corresponding alcohol IIc by reduction of the corresponding acyl halide IIb with a reducing agent such as lithium aluminium hydride. Treatment of alcohol IIb with the appropriate hydrohaloacid gives the desired halo derivative IId. A specific embodiments of this process is presented in Example 1.

B) Synthesis of Aryl Alcohol Derivatives 2-phenyl-4-hydroxyquinoline derivatives IIIc were prepared according to Giardina et al. (J. Med. Chem., (1997), 40, 1794–1807).

SCHEME III

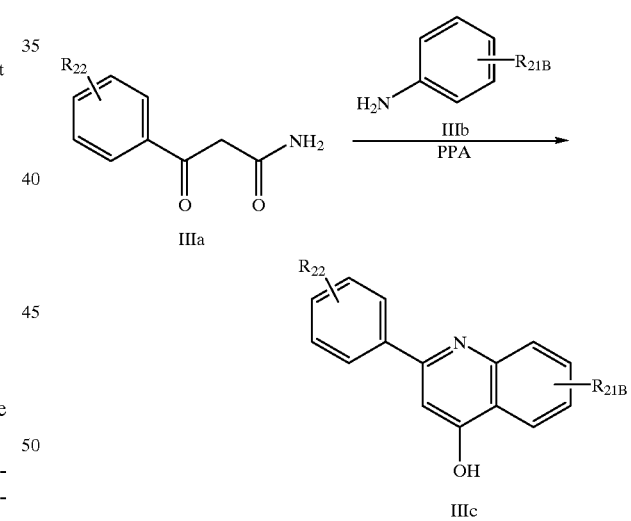

$R_{22}$ & $R_{21B}$=alkyl, OH, SH, halo, NH$_2$, NO$_2$.

Briefly, benzoylacetamide (IIIa) was condensed with the appropriate aniline (IIIb) and the imine obtained was cyclized with polyphosphoric acid to give the corresponding 2-phenyl-4-hydroxyquinoline (IIIc). A specific embodiment of this process presented in Example 2.

Or alternatively, the process can be carried out in a different manner: Benzoylethyl ester (IIIa) was condensed with the appropriate aniline (IIIb) in the presence of acid and the imine obtained was cyclized by heating at 260–280° C. to give the corresponding 2-phenyl-4-hydroxyquinoline (IIIc). A specific embodiments of this process is presented in Example 3 (compound 3e).

2.2. Synthesis of P2
A) The Synthesis of 4-substituted Proline
   (wherein $R^2$ is attached to the ring via a carbon atom) (with the stereochemistry as shown):

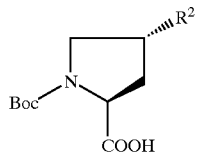

is done as shown in Scheme IV according to the procedures described by J. Ezquerra et al. (Tetrahedron, (1993), 38, 8665–8678) and C. Pedregal et al. (Tetrahedron Lett., (1994), 35, 2053–2056).

SCHEME IV

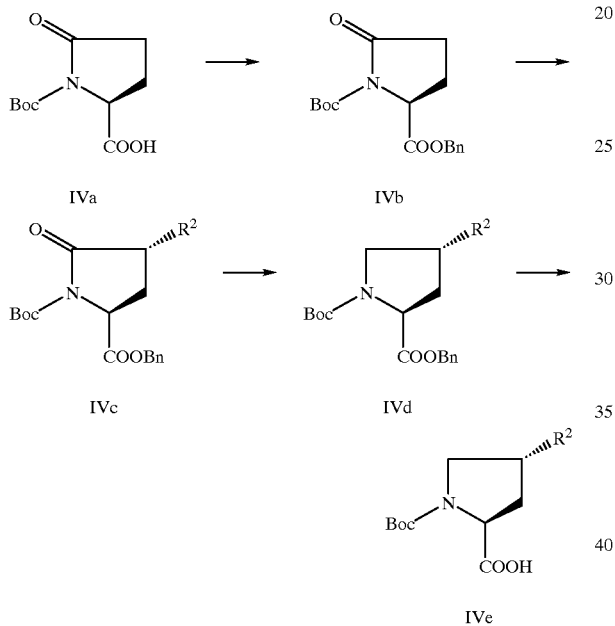

Briefly, Boc-pyroglutamic acid is protected as a benzyl ester. Treatment with a strong base such as lithium diisopropylamide followed by addition of an alkylating agent (Br—$R^{20}$ or I—$R^{20}$) gives the desired compounds IVe after reduction of the amide and deprotection of the ester.

B) The Synthesis of O-substituted-4-(R)-hydroxyproline:

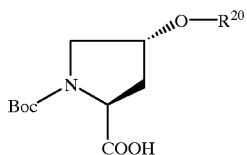

may be carried out using the different processes described below.

1) When $R^{20}$ is aryl, aralkyl, Het or (lower alkyl)-Het, the process can be carried out according to the procedure described by E. M. Smith et al. (J. Med. Chem. (1988), 31, 875–885). Briefly, commercially available Boc-4 (R)-hydroxyproline is treated with a base such as sodium hydride or potassium tert-butoxide and the resulting alkoxide reacted with halo-$R^{20}$ (Br—$R^{20}$, I—$R^{20}$, etc.) to give the desired compounds. Specific embodiments of this process are presented in Examples 4, 5 and 7.

2) Alternatively, when $R^{20}$ is aryl or Het, the compounds can also be prepared via a Mitsunobu reaction (Mitsunobu (1981), Synthesis, January, 1–28; Rano et al., (1995), Tet. Lett. 36(22), 3779–3792; Krchnak et al., (1995), Tet. Lett. 36(5), 62193–6196; Richter et al., (1994), Tet. Lett. 35(27), 4705–4706). Briefly, commercially available Boc-4(S)-hydroxyproline methyl ester is treated with the appropriate aryl alcohol or thiol in the presence of triphenylphosphine and diethylazodicarboxylate (DEAD) and the resulting ester is hydrolyzed to the acid. Specific embodiments of this process are presented in Examples 6 and 8.

SCHEME V

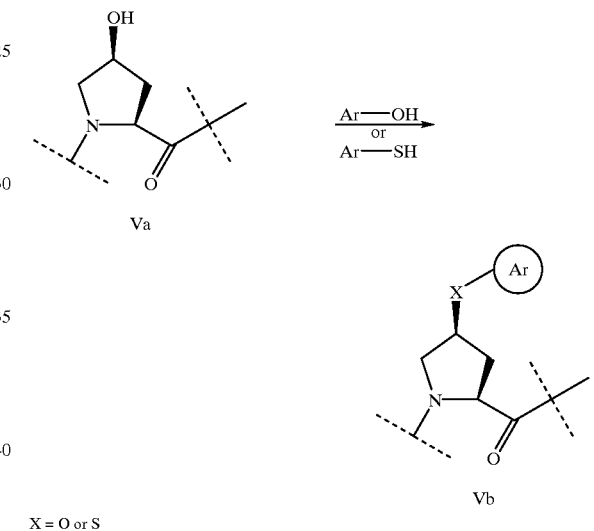

X = O or S

Alternatively, the Mitsunobu reaction can be carried out in solid phase (Scheme V). The 96-well block of the Model 396 synthesizer (advanced ChemTech) is provided with aliquots of resin-bound compound (Va) and a variety of aryl alcohols or thiols and appropriate reagents are added. After incubation, each resin-bound product (Vb) is washed, dried, and cleaved from the resin.

A Suzuki reaction (Miyaura et al., (1981), Synth. Comm. 11, 513; Sato et al., (1989), Chem. Lett., 1405; Watanabe et al., (1992), Synlett., 207; Takayuki et al., (1993), J. Org. Chem. 58, 2201; Frenette et al., (1994), Tet. Lett. 35(49), 9177–9180; Guiles et al., (1996), J. Org. Chem. 61, 5169–5171) can also be used to further functionalize the aryl substituent.

3. Synthesis of P1 Moieties 3.1 Synthesis of the 4 Possible Isomers of 2-substituted 1-aminocyclopropyl Carboxylic Acid The synthesis was done according to scheme VI.

SCHEME VI

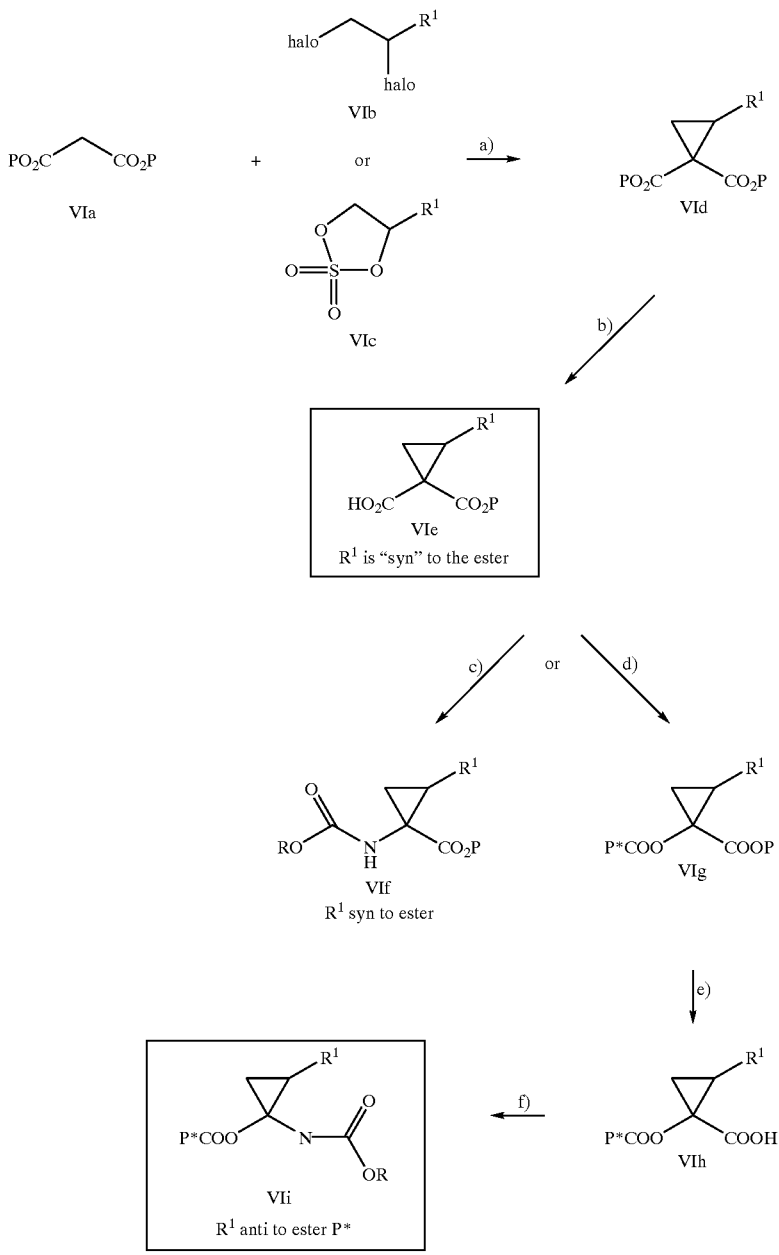

a) Briefly, di-protected malonate VIa and 1,2-dihaloalkane VIb or cyclic sulfate VIc (synthesized according to K. Burgess and Chun-Yen KE (Synthesis, (1996), 1463–1467) are reacted under basic conditions to give the diester VId.

b) A regioselective hydrolysis of the less hindered ester is performed to give the acid VIe.

c) This acid VIe is subjected to a Curtius rearrangement to give a racemic mixture of 1-aminocyclopropylcarboxylic acid derivatives VIf with $R^1$ being syn to the carboxyl group. A specific embodiment for this synthesis is presented in Example 9.

d, e) Alternatively, selective ester formation from the acid VIe with an appropriate halide (P*Cl) or alcohol (P*OH) forms diester VIg in which the P* ester is compatible with the selective hydrolysis of the P ester. Hydrolysis of P ester provides acid VIh.

f) A Curtius rearrangement on VIh gives a racemic mixture of 1-aminocyclopropylcarboxylic acid derivatives VIi with $R^1$ group being anti to the carboxyl group. A specific embodiment for this synthesis is presented in Example 14.

An alternative synthesis for the preparation of derivatives VIIf (when $R^1$ is vinyl and syn to the carboxyl group) is described below.

SCHEME VII

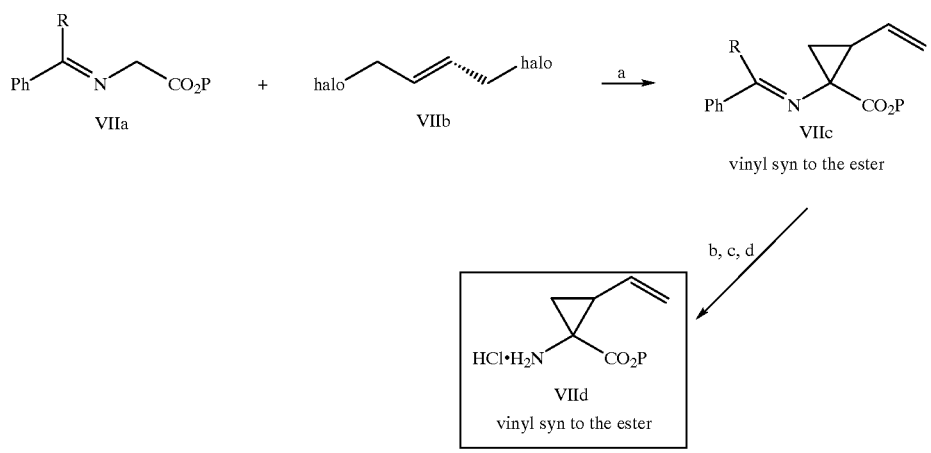

R = H, alkyl, aryl

Treatment of commercially available or easily obtainable imines VIIa with 1,4-dihalobutene VIIb in presence of a base produces, after hydrolysis of the resulting imine VIIc, VIId having the allyl substituent syn to the carboxyl group. Specific embodiments of this process are presented in Example 15 and 19.

Resolution of all of the above enantiomeric mixtures at carbon 1 (VIe and VIId) can be carried out via:
1) enzymatic separation (Examples 13, 17 and 20);
2) crystallization with a chiral acid (Example 18); or
3) chemical derivatization (Example 10).

Following resolution, determination of the absolute stereochemistry can be carried out as presented in Example 11.

Enantiomeric resolution and stereochemistry determination can be carried out in the same manner for the enantiomeric mixtures at carbon 1 wherein the substituent at C2 is anti to the carboxyl group (VIi).

3.2 Synthesis of 1-aminocyclobutyl Carboxylic Acid

The synthesis of 1,1-aminocyclobutanecarboxylic acid is carried out according to "Kavin Douglas; Ramaligam Kondareddiar; Woodard Ronald, Synth. Commun. (1985), 15 (4), 267–72.

SCHEME VIII

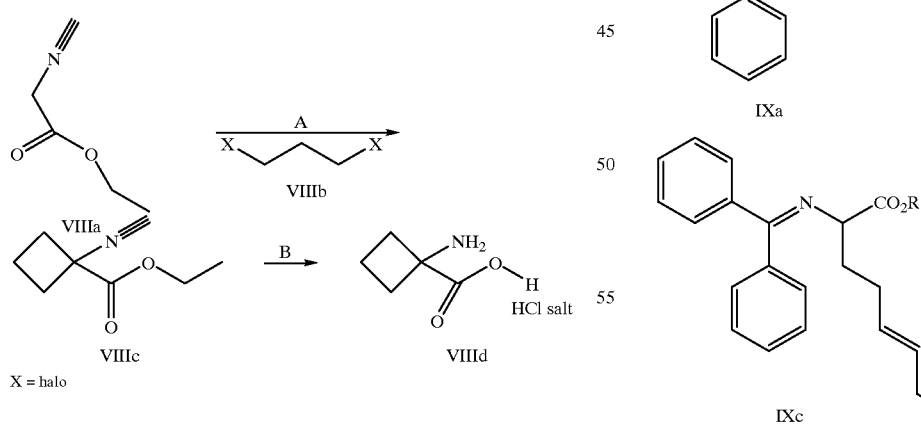

X = halo

Briefly, treatment of compound VIIIa with a base in the presence of VIIIb gives the corresponding cyclobutyl derivative VIIIc. Hydrolysis of the isocyanate and ester groups of VIIIc under acidic conditions (HCl) yields the hydrochloride salt of the 1-amino-cyclobutylcarboxylic acid VIIId. The carboxylic acid is later esterified under methanol in HCl. A specific embodiment of this esterification is described in Example 21.

3.3 Synthesis of 2-substituted 1-aminocyclobutyl Carboxylic Acid

SCHEME IX

-continued

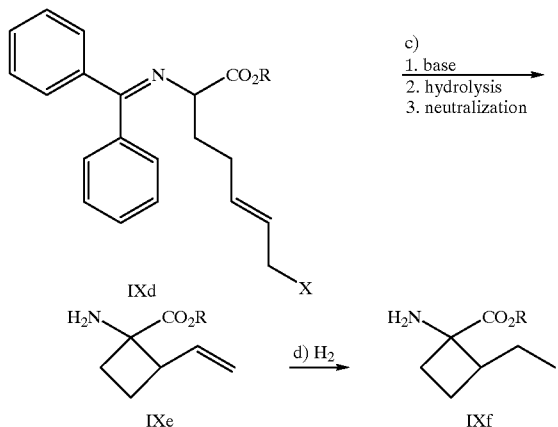

a) A protected glycine ester derivative such as imine IXa is alkylated with an homoallylic electrophile IXb using an appropriate base such as a metal hydride, hydroxide or alkoxide. Useful leaving groups in IXb include halogens (X=Cl, Br, I) or sulfonate esters (mesylate, tosylate or triflate). The allylic alcohol functionality in IXb is protected with hydroxyl protecting groups well known in the art (e.g. acetate, silyl, acetals).

b) In a second step, the hydroxyl function of monoalkylated derivative IXc is de-protected and converted to a suitable electrophilic function X such as described above for compound IXb.

c) Cyclization of IXd to cyclobutane derivative IXe is carried out by treatment with a base (metal hydrides, alkoxides), followed by hydrolysis using aqueous mineral acids and neutralization with a mild base. At this stage, syn and anti-isomers of IXe can be separated by flash chromatography.

d) Optionally, the double bond in IXe can also be hydrogenated under standard conditions to yield the corresponding saturated derivative IXf.

The invention further comprises a process for the preparation of a peptide analog of formula (I) wherein P1 is a substituted aminocyclopropyl carboxylic acid residue, comprising the step of:
coupling a peptide selected from the group consisting of: APG-P3-P2; or APG-P2;
with a P1 intermediate of formula:

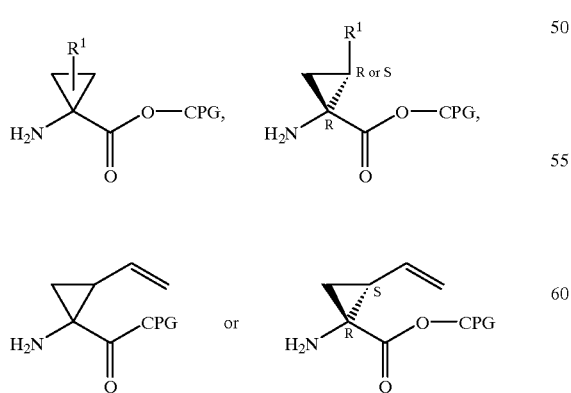

wherein $R_1$ is $C_{1-6}$ alkyl, cycloalkyl or $C_{2-6}$ alkenyl, all optionally substituted with halogen, CPG is a carboxyl protecting group and APG is an amino protecting group and P3 and P2 are as defined above.

The invention further comprises a process for the preparation of: 1) a serine protease inhibitor peptide analog, or 2) a HCV NS3 protease inhibitor peptide analog, this process comprising the step of:
coupling a (suitably protected) amino acid, peptide or peptide fragment with a P1 intermediate of formula:

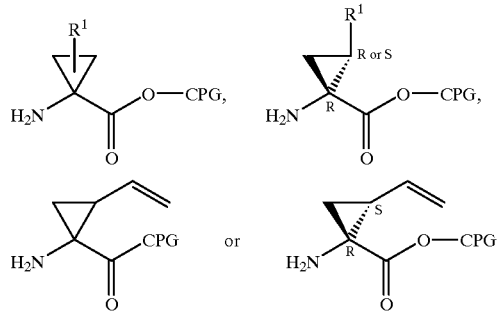

wherein $R^1$ is $C_{1-6}$ alkyl, $C_{3-7}$ cycloalkyl or $C_{2-6}$ alkenyl, all optionally substituted with halogen, and CPG is a carboxyl protecting group.

The invention therefore comprises a process for the preparation of: 1) a protease inhibitor peptide analog, or 2) a serine protease inhibitor peptide analog, this process comprising the step of:
coupling a (suitably protected) amino acid, peptide or peptide fragment with an intermediate of formula:

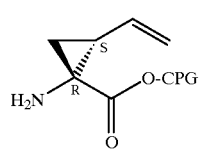

wherein CPG is a carboxyl protecting group.

The invention also comprises the use of a P1 intermediate of formula:

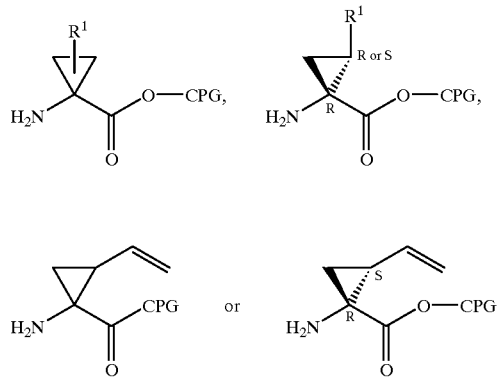

wherein $R^1$ is $C_{1-6}$ alkyl, cycloalkyl or $C_{2-6}$ alkenyl, all optionally substituted with halogen, for the preparation of: 1) a serine protease inhibitor peptide analog, or 2) a HCV NS3 protease inhibitor peptide analog.

The invention also comprises the use of an intermediate of formula:

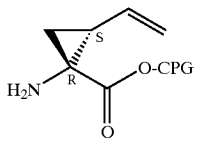

wherein CPG is a carboxyl protecting group, for the preparation of: 1) a protease inhibitor peptide analog, or 2) a serine protease inhibitor peptide analog.

The invention also comprises the use of a P1 intermediate of formula:

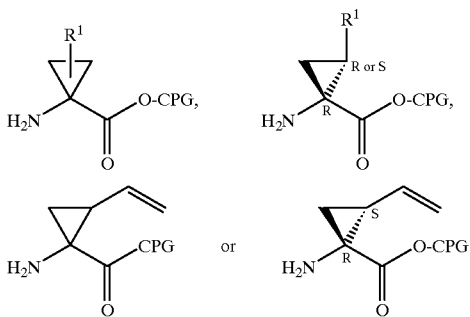

wherein $R^1$ is $C_{1-6}$ alkyl, cycloalkyl or $C_{2-6}$ alkenyl, all optionally substituted with halogen, for the preparation of a compound of formula I as defined above.

Finally, the invention also comprises the use of a proline analog of formula:

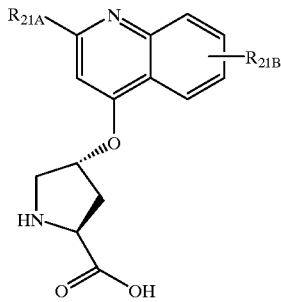

wherein $R_{21A}$ is $C_{1-6}$ alkyl; $C_{1-6}$ alkoxy; lower thioalkyl; halo; amino optionally mono-substituted with $C_{1-6}$ alkyl; $C_6$, $C_{10}$ aryl, $C_{7-16}$ aralkyl or Het, said aryl, aralkyl or Het optionally substituted with $R_{22}$ wherein $R_{22}$ is $C_{1-6}$ alkyl, $C_{1-6}$ alkoxy, amido, (lower alkyl) amide, amino optionally mono- or di-substituted with $C_{1-6}$ alkyl, or Het, and $R_{21B}$ is $C_{1-6}$ alkyl, $C_{1-6}$ alkoxy, amino, di(lower alkyl)amino, (lower alkyl)amide, $NO_2$, OH, halo, trifluoromethyl, or carboxyl;

for the synthesis of 1) a serine protease inhibitor peptide analog, 2) a HCV NS3 protease inhibitor peptide analog, or 3) a peptide analog of formula I as defined above.

EXAMPLES

The present invention is illustrated in further detail by the following non-limiting examples.

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million. Flash chromatography was carried out on silica gel ($SiO_2$) according to Still's flash chromatography technique (W. C. Still et al., J. Org. Chem., (1978), 43, 2923).

Abbreviations used in the examples include Bn: benzyl; Boc: tert-butyloxycarbonyl {$Me_3COC(O)$}; BSA: bovine serum albumin; CHAPS: 3-[(3-cholamidopropyl)-dimethylammonio]-1-propanesulfonate; DBU: 1,8-diazabicyclo[5.4.0]undec-7-ene; $CH_2Cl_2$=DCM: methylene chloride; DEAD: diethylazodicarboxylate; DIAD: diisopropylazodicarboxylate; DIEA: diisopropylethylamine; DIPEA: diisopropylethylamine; DMAP: dimethylaminopyridine; DCC: 1,3-dicyclohexylcarbodiimide; DME: 1,2-dimethyoxyethane; DMF: dimethylformamide; DMSO: dimethylsulfoxide; DTT: dithiothreitol or threo-1,4-dimercapto-2,3-butanediol; DPPA: diphenylphosphoryl azide; EDTA: ethylenediaminetetraacetic acid; Et: ethyl; EtOH: ethanol; EtOAc: ethyl acetate; $Et_2O$: diethyl ether; HATU: [O-7-azabenzotriazol-1-yl)-1,1,3,3-tetramethyluronium hexafluorophosphate]; HPLC: high performance liquid chromatography; MS: mass spectrometry (MALDI-TOF: Matrix Assisted Laser Disorption Ionizaton-Time of Flight, FAB: Fast Atom Bombardment); LAH: lithium aluminum hydride; Me: methyl; MeOH: methanol; MES: (2-{N-morpholino}ethane-sulfonic acid); NaHMDS: sodium bis(trimethylsilyl)amide; NMM: N-methylmorpholine; NMP: N-methylpyrrolidine; Pr: propyl; Succ: 3-carboxypropanoyl; PNA: 4-nitrophenylamino or p-nitroanilide; TBAF: tetra-n-butylammonium fluoride; TBTU: 2-(1H-benzotriazole-1-yl)-1,1,3,3-tetramethyluronium tetrafluoroborate; TCEP: tris(2-carboxyethyl)phosphine hydrochloride; TFA: trifluoroacetic acid; THF: tetrahydrofuran; TIS: triisopropylsilane; TLC: thin layer chromatography; TMSE: trimethylsilylethyl; Tris/HCl: tris(hydroxymethyl)aminomethane hydrochloride.

P2 Building Blocks

Example 1

Synthesis of bromomethyl-8-quinoline (1)

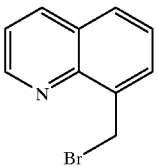

To commercially available 8-quinoline carboxylic acid (2.5 g, 14.4 mmol) was added neat thionyl chloride (10 ml, 144 mmol). This mixture was heated at 80° C. for 1 h before the excess thionyl chloride was distilled off under reduced pressure. To the resulting brownish solid was added absolute EtOH (15 mL) which was heated at 80° C. for 1 h before being concentrated in vacuo. The residue was partitioned between EtOAc and saturated aqueous $NaHCO_3$, and the organic phase dried ($MgSO_4$), filtered and concentrated to give a brownish oil (2.8 g). This material (ca. 14.4 mmol) was added dropwise over 35 min to a LAH (0.76 g, 20.2 mmol)/$Et_2O$ suspension which was cooled to −60° C. The reaction mixture was slowly warmed to −35° C. over 1.5 h before the reaction was complete. The reaction was quenched with MgSO$_4$·10H$_2$O slowly over 30 min and then wet THF. The mixture was partitioned between Et$_2$O and 10% aqueous NaHCO$_3$. The organic phase was dried (MgSO$_4$), filtered and concentrated to give a yellowish solid (2.31 g, 80% over 2 steps) corresponding to the alcohol. The alcohol (2.3 g, 11.44 mmol) was dissolved in AcOH/HBr (20 mL, 30% solution from Aldrich) and heated at 70° C. for 2.5 h. The mixture was concentrated in vacuo to dryness, partitioned between EtOAc (100 mL) and saturated aqueous NaHCO$_3$ before being dried (MgSO$_4$), filtered and concentrated to give the desired compound (1) as a brownish solid (2.54 g, 100%).

Example 2

Synthesis of 2-phenyl-4-hydroxyquinoline (2)

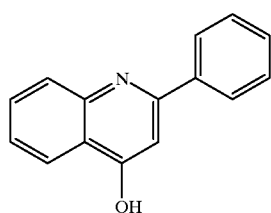
(2)

Commercially available ethyl benzoylacetate (6.00 g, 31.2 mmol) was heated at 85° C. (sealed tube) in 75 mL of 30% NH$_4$OH for 2 hours. The solid formed upon cooling was filtered and refluxed in water for 2 hours. The solution was extracted three times with CH$_2$Cl$_2$. The organic layers were combined, dried over MgSO$_4$, filtered and concentrated. The yellow residue was flash chromatographed on silica gel, eluting with EtOAc:hexane (3:7), to give the corresponding amide as a white solid, 1.60 g, 31% yield.

This amide (250 mg, 1.53 mmol) was refluxed using a Dean-Stark apparatus with aniline (143 mg, 1.53 mmol) and aniline.HCl (10 mg, 0.08 mmol) in toluene (10 mL) for 16 h. The solution was concentrated to afford a brown oil that was mixed with polyphosphoric acid (2 g) and heated at 135° C. for 20 min. The reaction mixture was poured into water and adjusted to pH 8 with 5 M NaOH. The aqueous suspension was extracted twice with ethyl acetate. The organic layers were combined, washed with brine, dried over MgSO$_4$, filtered and concentrated. The residue was flash chromatographed on silica gel, eluting with 3% MeOH in ethyl acetate, to give 2-phenyl-4-hydroxyquinoline (2), 67 mg, 20% yield.

$^1$H NMR (DMSO-d$_6$) δ8.11 (d, J=7 Hz, 1 H), 7.86–7.83 (m, 2 H), 7.77 (d, J=8 Hz, 1 H), 7.68 (dd, J=8, 7 Hz, 1 H), 7.61–7.58 (m, 3 H), 7.35 (dd, J=8, 7 Hz, 1 H), 6.34 (s, 1 H).

Example 3

Synthesis of 4-hydroxy-2-phenyl-7-methoxyquinoline (3)

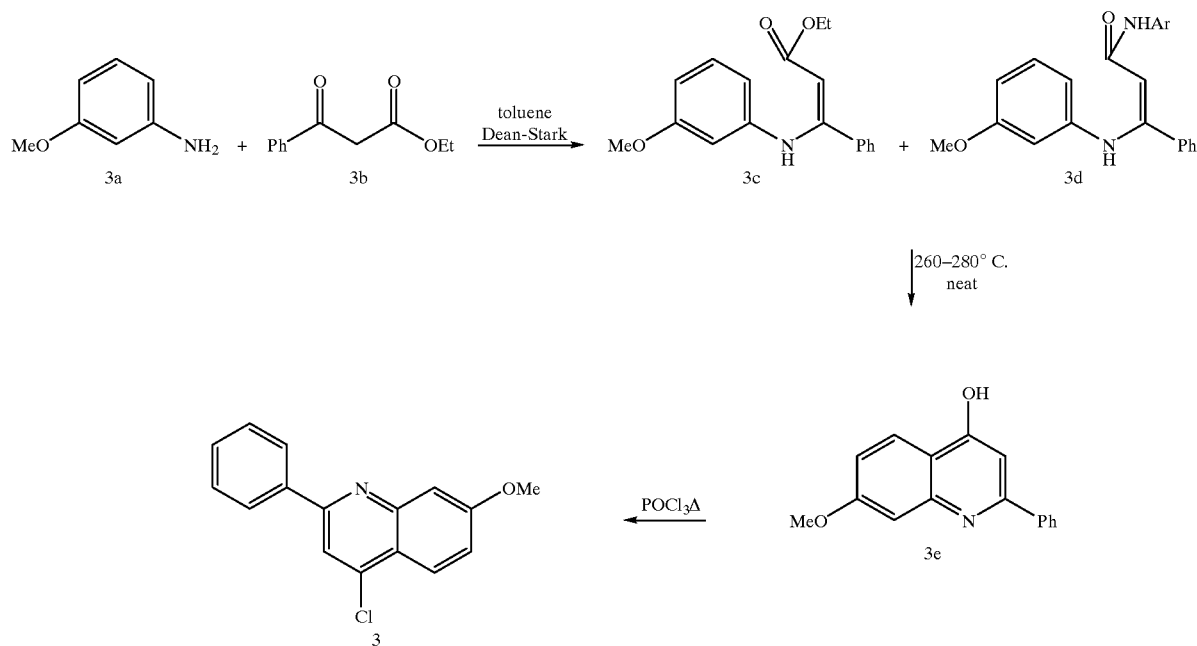

4-hydroxy-2-phenyl-7-methoxyquinoline (e)

A solution of ethyl benzoylacetate (b) (100.0 g, 0.52 mol), m-anisidine (a) (128.1 g, 1.04 mol) and 4 N HCl/dioxane (5.2 mL) in toluene (1.0 L) was refluxed for 6.25 h in a Dean-Stark apparatus. The cooled toluene solution was successively washed with aqueous 10% HCl (2×300 mL), 1 N NaOH (2×300 mL), H$_2$O (300 mL) and brine (150 mL). The toluene phase was dried (MgSO$_4$), filtered and concen trated under reduced pressure to give a 1.2:1.0 mixture of ester c and amide d (144.6 g, 45%/38% crude yield) as a dark brown oil. The crude oil was heated to 280° C. for 80 min while distilling generated EtOH. The cooled dark solid obtained was triturated with CH$_2$Cl$_2$ (200 mL). The suspension was filtered and the resulting solid washed with CH$_2$Cl$_2$ to give e (22.6 g, 17% from a) as a beige solid: $^1$H NMR (DMSO-d$_6$) δ8.00 (d, J=9.0 Hz, 1H), 7.81–7.82 (m, 2H), 7.57–7.59 (m, 3H), 7.20 (d, J=2.2 Hz, 1H), 6.94 (dd, J=9.0, 2.2 Hz, 1H), 6.26 (s, 1H), 3.87 (s, 3H).

4-Chloro-2-phenyl-7-methoxyquinoline (3)

A suspension of e (8.31 g, 33.1 mmol) in POCl$_3$ (90 mL) was heated to reflux for 2 h (clear solution obtained upon heating). The reaction mixture was concentrated under reduced pressure. The residue was partitioned between 1 N NaOH (exothermic, 10 N NaOH added to maintain high pH) and EtOAc (500 mL). The organic layer was washed with H$_2$O (100 mL) then brine (100 mL) was dried (MgSO$_4$), filtered and concentrated under reduced pressure to give 3 (8.60 g, 96%) as a pale yellow solid: $^1$H NMR (DMSO-d$_6$) δ8.28–8.30 (m, 2H), 8.20 (s, 1H), 8.10 (d, J=9.1 Hz, 1H), 7.54–7.58 (m, 3H), 7.52 (d, J=2.5 Hz, 1H), 7.38 (dd, J=9.1, 2.5 Hz, 1H), 3.98 (s, 3H). This reaction was repeated three times and gave always 96–98% yield which is significantly higher that the 68% yield reported in J. Med. Chem. 1997, 40, 1794.

Example 4

Synthesis of Boc-4(R)-(naphthalen-1-ylmethoxy) proline (4)

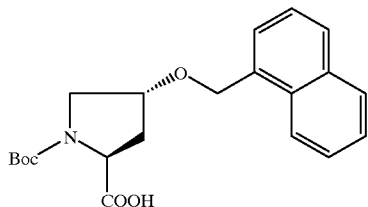

(4)

Commercially available Boc-4(R)-hydroxyproline (5.00 g, 21.6 mmol) was dissolved in THF (100 mL) and cooled to 0° C. Sodium hydride (60% dispersion in oil, 1.85 g, 45.4 mmol) was added portionwise over 10 minutes and the suspension was stirred at RT for 1 h. Then, 1-(bromomethyl) naphthalene (8.00 g, 36.2 mmol) (prepared as described in E. A. Dixon et al. Can. J. Chem., (1981), 59, 2629–2641) was added and the mixture was heated at reflux for 18 h. The mixture was poured into water (300 mL) and washed with hexane. The aqueous layer was acidified with 10% aqueous HCl and extracted twice with ethyl acetate. The organic layers were combined and washed with brine, dried (MgSO$_4$), filtered and concentrated. The residue was purified by flash chromatography (49:49:2 hexane:ethyl acetate:acetic acid) to give the title compound as a colorless oil (4.51 g, 56% yield). $^1$H NMR (DMSO-d$_6$) indicated the presence of two rotamers: δ8.05 (m, 1H), 7.94 (m, 1H), 7.29 (d, J=14 Hz, 1H), 7.55–7.45 (m, 4H), 4.96 (m, 2H), 4.26 (br. s, 1H), 4.12 (dd, J=J=8 Hz, 1H), 3.54–3.42 (m, 2H), 2.45–2.34 (m, 1H), 2.07–1.98 (m, 1H) 1.36 (s, (3/9) 9H), 1.34 (s, (6/9) 9H).

Example 5

Synthesis of Boc-4(R)-(8-quinoline-methoxy) proline (5)

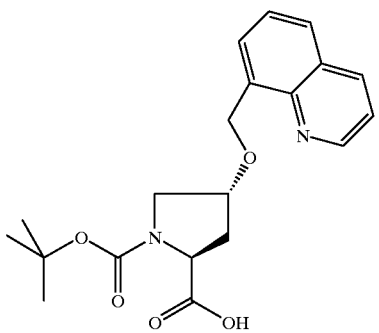

(5)

Boc-4(R)-hydroxyproline (1.96 g, 8.5 mmol) in anhydrous THF (20 mL) was added to a suspension of NaH (1.4 g, 60% in oil, 34 mmol) in THF (100 mL). This mixture was stirred 30 min before bromomethyl-8-quinoline from Example 1 (2.54 g, 11.44 mmol) was added in THF (30 mL). The reaction mixture was heated at 70° C. (5 h) before the excess NaH was destroyed carefully with wet THF. The reaction was concentrated in vacuo and the resulting material was dissolved in EtOAc and H$_2$O. The basic aqueous phase was separated and acidified with 10% aqueous HCl to pH ~5 before being extracted with EtOAc (150 mL). The organic phase was dried (MgSO$_4$), filtered and concentrated to give a brown oil. Purification by flash chromatography (eluent 10% MeOH/CHCl$_3$) gave the desired compound (5) as a pale yellow solid (2.73 g, 86%). HPLC (97.5%); $^1$H-NMR (DMSO-d$_6$) shows rotamer populations in a 6:4 ratio, δ12–11.4 (bs, 1H), 8.92 (2×d, J=4.14 and 4.14 Hz, 1H), 8.38 (2×d, J=8.27 and 8.27 Hz, 1H), 7.91 (d, J=7.94 Hz, 1H), 7.77 (d, J=7.0 Hz, 1H), 7.63–7.54 (m, 2H), 5.14 (2×s, 2H), 4.32–4.29 (m, 1H), 4.14–4.07 (m, 1H), 3.52–3.44 (m, 2H), 2.43–2.27 (m, 1H), 2.13–2.04 (m, 1H), 1.36 and 1.34 (2×s, 9H).

Example 6

Preparation of Boc-4(R)-(7-chloroquinoline-4-oxo) proline (6)

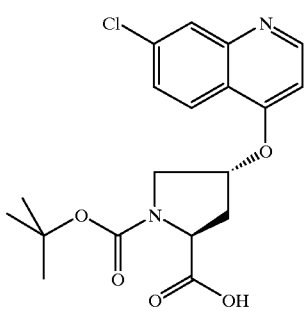

(6)

Commercially available Boc-4(S)-hydroxyproline methyl ester (500 mg, 2.04 mmol) and 7-chloro-4-hydroxyquinoline (440 mg, 2.45 mmol) were placed in dry THF (10 mL) at 0° C. Triphenylphosphine (641 mg, 2.95 mmol) was added, followed by slow addition of DIAD (426 mg, 2.45 mmol). The mixture was stirred at RT for 20 h. The reaction mixture was then concentrated, taken up in ethyl acetate and extracted three times with HCl 1N. The aqueous phase was basified with Na$_2$CO$_3$ and extracted twice with ethyl acetate. The organic layers were combined, dried over MgSO$_4$, filtered and concentrated to give a yellow oil. The oil was purified by flash chromatography to give the methyl ester as a white solid, 498 mg, 58% yield. This methyl ester (400 mg, 0.986 mmol) was hydrolyzed with 1M aqueous sodium hydroxide (1.7 mL, 1.7 mmol) in methanol (4 mL), at 0° C., for 3 h. The solution was concentrated to remove the methanol and neutralized with 1M aqueous HCl. The suspension was concentrated to dryness and taken up in methanol (20 mL), the salts were filtered off and the filtrate concentrated to give the desired compound (6) as a white solid, 387 mg, quant. yield.

$^1$H NMR (DMSO-d$_6$) (ca. 1:1 mixture of rotamers) δ8.74 (d, J=5 Hz, 1 H), 8.13–8.09 (m, 1 H), 7.99 and 7.98 (s, 1 H), 7.58 (d, J=9 Hz, 1 H), 7.02 (d, J=5 Hz, 1 H), 5.26–5.20 (m, 1 H), 4.10–4.01 (m, 1 H), 3.81–3.72 (m, 1 H), 3.59 (dd, J=12, 10 Hz, 1 H), 2.41–2.31 (m, 2 H), 1.34 and 1.31 (s, 9H).

Example 7

Synthesis of Boc-4(R)-(2-phenyl-7-methoxyquinoline-4-oxo)proline (7)

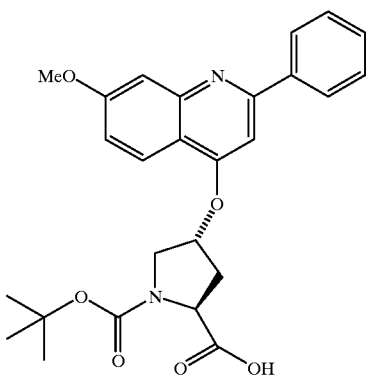

Boc-4(R)-(2-phenyl-7-methoxyquinoline-4-oxo) proline (7)

Potassium tert-butoxide (8.16 g, 72.7 mmol) was added in small portions, over 15 min, to a solution of Boc-4(R)-hydroxy proline (6.73 g, 29.1 mmol) in DMSO (83 mL) maintained at 25° C. The mixture was stirred at 25° C. for 1.5 h. Chloro-2-phenyl-7-methoxyquinoline 3 (8.61 g, 32.0 mmol) was added in 4 portions over 15 min to the reaction mixture. The reaction mixture was stirred at 25° C. for 19 h. The resulting suspension was poured in H$_2$O (650 mL) and the mixture was washed with Et$_2$O (3×150 mL) to remove excess chloroquinoline (EtOAc was later found to be more efficient). The aqueous layer was acidified with aqueous 1 N HCl (38 mL of calculated 1.5 equiv. required, 43.6 mL) to pH 4–5. The white solid that precipitated was recovered by filtration. The moist solid was dried under reduced pressure over P$_2$O$_5$ to give the proline derivative 7 (12.6 g, 91%, contains 2.3% w/w of DMSO) as a beige solid:

$^1$H NMR (DMSO-d$_6$) δ(2:1 mixture of rotamers) 8.27 (d, J=7.0 Hz, 2H), 8.00, 7.98 (2d, J=9.2, ~9.2 Hz, 1H), 7.48–7.56 (m, 3H), 7.45, 7.43 (2s, 1H), 7.39 (d, J=2.5 Hz, 1H), 7.17 (dd, J=9.2, 2.5 Hz, 1H), 5.53–5.59 (m, 1H), 4.34–4.41 (m, 1H), 3.93 (s, 3H), 3.76 (broad s, 2H), 2.63–2.73 (m, 1H), 2.32–2.43 (m, 1H), 1.36, 1.33 (2s, 9H).

Example 8

Synthesis of Boc-4(R)-(2-phenyl-6-nitroquinoline-4-oxo)proline (8)

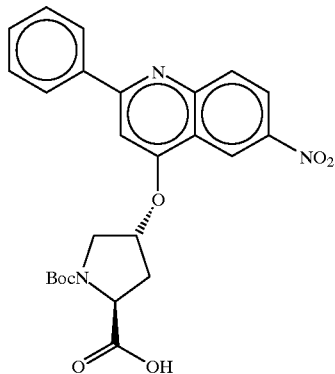

Diethyl azodicarboxylate (0.77 mL, 4.89 mmol) was added dropwise to a stirred solution of triphenylphosphine (1.28 g, 4.88 mmol) in 15 mL of tetrahydrofuran at 0° C. After 30 min. of stirring under nitrogen a solution of Boc-4(S)-hydroxyproline methyl ester (1.00 g, 4.08 mmol) was added in 5 mL of tetrahydrofuran followed by a suspension of commercially available 6-nitro-2-phenyl-4-quinolinol (1.30 g, 4.88 mmol) in 10 mL of the same solvent. The red mixture was stirred for 15 min. at 0° C. and at RT overnight. The solvent was evaporated in vacuo. The remaining oil was diluted in ethyl acetate and washed twice with sodium bicarbonate, once with water and once with brine. The organic layer was dried (MgSO$_4$), filtered and evaporated in vacuo. The residue was chromatographed over silica gel (70:30 v/v, hexanes-ethyl acetate) affording the desired methyl ester as a light yellow solid (1.70 g, 85%).

$^1$H NMR(CDCl$_3$) rotamers=3:7δ9.03 (d, J=2.5 Hz, 1H), 8.46 (dd, J=9, 2.5 Hz, 1H), 8.18 (d, J=9 Hz, 1H), 8.14–8.07 (m, 2H), 7.59–7.50 (m, 3H), 7.19 (s, 1H), 5.39–5.30 (m, 1H), 4.67 (t, J=8 Hz, 0.3H), 4.61 (t, J=8 Hz, 0.7H), 4.07–4.01 (m, 2H), 3.81 (s, 3H), 2.89–2.73 (m, 1H), 2.55–2.47 (m, 1H), 1.49 (s, 2.7H), 1.45 (s, 6.3H).

To a solution of the methyl ester (503 mg, 1.02 mmol) in a mixture of THF: H$_2$O (10:4 mL) was added lithium hydroxide monohydrate (85 mg, 2.05 mmol). 2 mL of MeOH was added in order to get an homogeneous solution. A white precipitate resulted within 30 min. The resulting suspension was stirred at RT for an additional 6 h. The reaction mixture was diluted with an aqueous solution of citric acid 10% and extracted with ethyl acetate. The organic layer was dried (MgSO$_4$), filtered and evaporated in vacuo to afford 416 mg (85%) of the desired acid (8).

$^1$H NMR (DMSO-$_6$): δ8.92–8.87 (m, 1H), 8.47 (dd, J=9, 3 Hz, 1H), 8.38–8.32 (m, 2H), 8.19 (d, J=9 Hz, 1H), 7.77 (s, 1H), 7.62–7.55 (m, 3H), 5.73–5.66 (m, 1H), 4.41 (t, J=8 Hz, 1H), 3.89–3.76 (m, 2H), 2.83–2.72 (m, 1H), 2.47–2.35 (m, 1H), 1.38 (s, 9H).

P1 Building Blocks

Example 9

A) Synthesis of mixture of (1R,2R)/(1S,2R) 1-amino-2-ethylcyclopropyl carboxylic acid

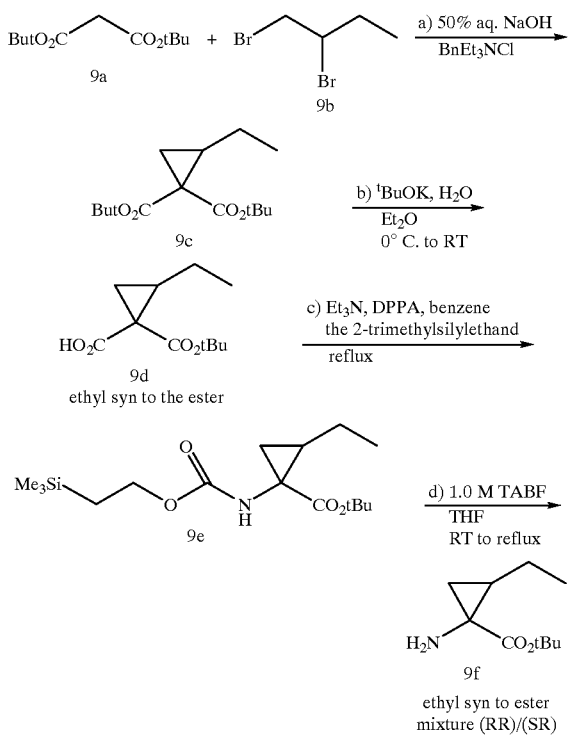

a) To a suspension of benzyltriethylammonium chloride (21.0 g, 92.19 mmol) in a 50% aqueous NaOH solution (92.4 g in 185 mL H$_2$O) were successively added di-tert-butylmalonate (20.0 g, 92.47 mmol) and 1,2-dibromobutane (30.0 g, 138.93 mmol). The reaction mixture was vigorously stirred overnight at RT, a mixture of ice and water was then added. The crude product was extracted with CH$_2$Cl$_2$ (3×) and sequentially washed with water (3×) and brine. The organic layer was dried (MgSO$_4$), filtered and concentrated. The residue was flash chromatographed (7 cm, 2 to 4% Et$_2$O in hexane) to afford the desired cyclopropane derivative 9c (19.1 g, 70.7 mmol, 76% yield). $^1$H NMR (CDCl$_3$) δ1.78–1.70 (m, 1H), 1.47 (s, 9H), 1.46 (s, 9H), 1.44–1.39 (m, 1H), 1.26–1.64 (m, 3H), 1.02 (t, 3H, J=7.6 Hz).

b) To a suspension of potassium tert-butoxide (6.71 g, 59.79 mmol, 4.4 eq.) in dry ether (100 mL) at 0° C. was added H$_2$O (270 μL, 15.00 mmol, 1.1 eq.). After 5 min diester 9c (3.675 g, 13.59 mmol) in ether (10 mL) was added to the suspension. The reaction mixture was stirred overnight at RT, then poured in a mixture of ice and water and washed with ether (3×). The aqueous layer was acidified with a 10% aq. citric acid solution at 0° C. and extracted with AcOEt (3×). The combined organic layer was successively washed with water (2×) and brine. After the usual treatment (Na$_2$SO$_4$, filtration, concentration), the desired acid 9d was isolated as a pale yellow oil (1.86 g, 8.68 mmol, 64% yield). $^1$H NMR (CDCl$_3$) δ2.09–2.01 (m, 1H), 1.98 (dd, J=3.8, 9.2 Hz, 1H), 1.81–1.70 (m, 1H), 1.66 (dd, J=3.0, J=8.2 Hz, 1H), 1.63–1.56 (m, 1H), 1.51 (s, 9H), 1.0 (t, J=7.3 Hz, 3H).

c) To the acid 9d (2.017 g, 9.414 mmol) in dry benzene (32 mL) were successively added Et$_3$N (1.50 mL, 10.76 mmol, 1.14 eq.) and DPPA (2.20 mL, 10.21 mmol, 1.08 eq.). The reaction mixture was refluxed for 3.5 h then 2-trimethylsilylethanol (2.70 mL, 18.84 mmol, 2.0 eq.) was added. The reflux was maintained overnight then the reaction mixture was diluted with Et$_2$O and successively washed with a 10% aqueous citric acid solution, water, saturated aqueous NaHCO$_3$, water (2×) and brine. After the usual treatment (MgSO$_4$, filtration, concentration) the residue was purified by flash chromatography (5 cm, 10% AcOEt-hexane) to afford the desired carbamate 9e (2.60 g, 7.88 mmol, 84% yield) as a pale yellow oil. MS (FAB) 330 (MH$^+$); $^1$H NMR (CDCl$_3$) δ5.1 (bs, 1H), 4.18–4.13 (m, 2H), 1.68–1.38 (m, 4H), 1.45 (s, 9H), 1.24–1.18 (m, 1H), 1.00–0.96 (m, 5H), 0.03 (s, 9H).

d) To carbamate 9e (258 mg, 0.783 mmol) was added a 1.0 M TBAF solution in THF (940 μL, 0.94 mmol, 1.2 eq.). After 4.5 h an additional amount of 1.0 M TBAF was added (626 μL, 0.63 mmol, 0.8 eq.). The reaction mixture was stirred overnight at RT, refluxed for 30 min and then diluted with AcOEt. The solution was successively washed with water (2×) and brine. After the usual treatment (MgSO$_4$, filtration and concentration) the desired amine 9f was isolated (84 mg, 0.453 mmol, 58% yield) as a pale yellow liquid. $^1$H NMR (CDCl$_3$) δ1.96 (bs, 2H), 1.60–1.40 (m, 2H), 1.47 (s, 9H), 1.31–1.20 (m, 1H), 1.14 (dd, J=4.1, 7.3 Hz, 1H), 1.02 (dd, J=4.1, 9.2 Hz, 1H), 0.94 (t, J=7.3 Hz, 3H).

Example 10

Chemical resolution of t-butyl-(1R,2R)/(1S,2R) 1-amino-2-ethylcyclopropyl carboxylate (from Example 9)

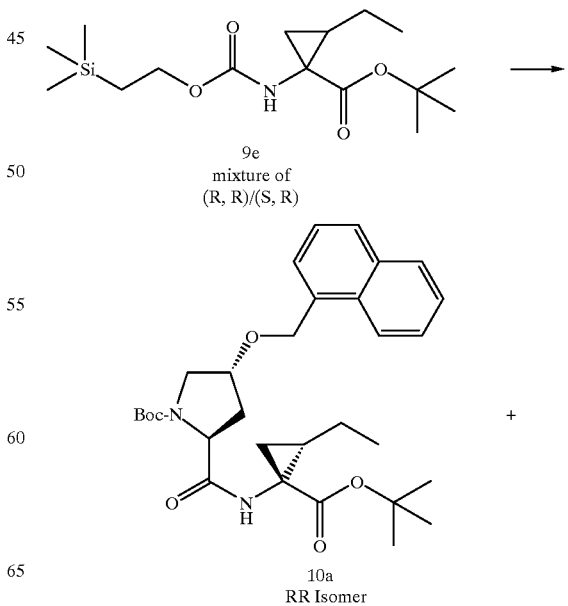

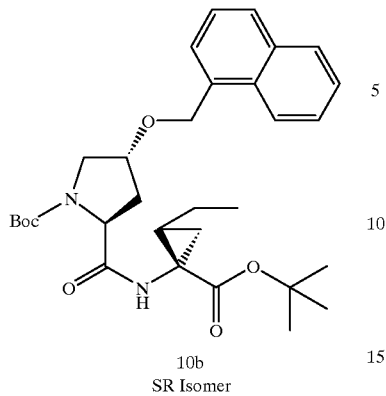

10b
SR Isomer

Isomers separated by column chromatography.

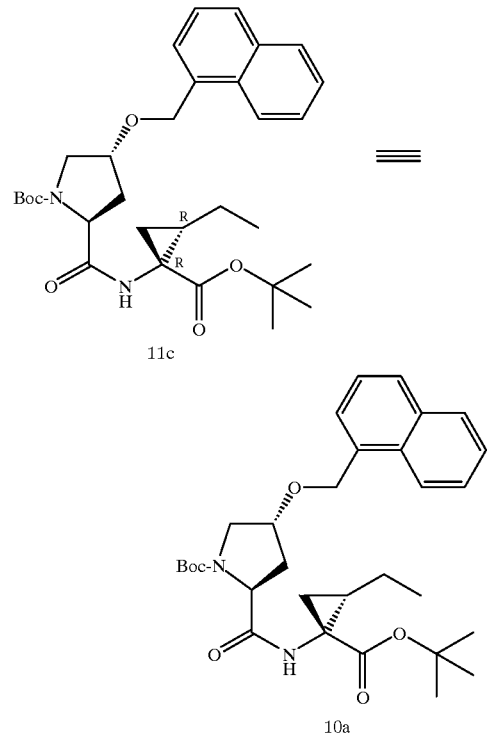

11c

10a

Direct comparison by TLC, HPLC and NMR

Compound 9e from Example 9 (8.50 g, 25.86 mmol) was treated with 1M TBAF/THF (26 mL) at reflux for 45 min. The cooled reaction mixture was diluted with EtOAc, washed with water (3×) and brine (1×), then, dried (MgSO₄), filtered and evaporated to provide the free amine as a light yellow oil. The free amine was dissolved in anhydrous CH₂Cl₂ (120 mL), NMM (8.5 mL, 77.57 mmol), compound 4 (Example 4) (10.08 g, 27.15 mmol) and HATU (11.79 g, 31.03 mmol) were added successively. The reaction mixture was stirred at RT overnight, then worked up as described previously. The crude diastereomeric mixture was separated by flash chromatography (eluent—hexane:Et₂O; 25:75) to provide the dipeptide 10a (the less polar eluting spot) as a white foam (4.42 g; 64% of the theoretical yield) and 10b (the more polar eluting spot) as an ivory foam (4 g., 57% of theoretical yield). At this time both isomers were separated but the absolute stereochemistry was still not known.

Example 11

Determination of the absolute stereochemistry of compounds 10a and 10b by correlation with known t-butyl(1R-amino-2R-ethylcyclopropyl carboxylate

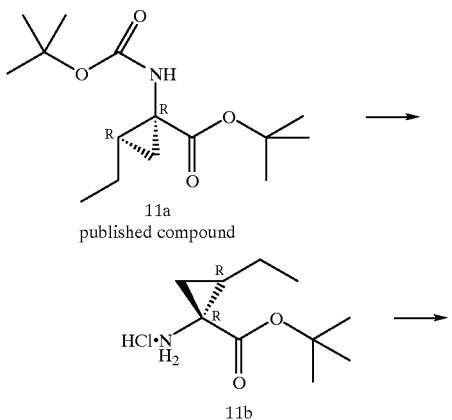

11a
published compound

11b

Prof. A. Charette, from the University of Montreal, provided compound 11a having the absolute stereochemistry as shown, which was determined by X-ray crystallography (J. Am. Chem. Soc., 1995, 117, 12721). Compound 11a (13.2 mg, 0.046 mmol) was dissolved in 1M HCl/EtOAc (240 μL) and stirred approximately 48 hours. The mixture was evaporated to dryness to provide compound 11b as a light yellow paste and was coupled to compound 4 (18 mg, 0.049 mmol) as described in Example 10, using NMM (20.3 μL, 0.185 mmol) and HATU (21.1 mg, 0.056 mmol) in CH₂Cl₂. The crude material was purified by flash chromatography (eluent—hexane:Et₂O; 50:50) to provide the dipeptide 11c as an oil (7.7 mg; 31%). By TLC, HPLC and NMR comparison, dipeptide 11c, was found to be identical to the less polar compound 10a obtained in Example 10, thus identifying the absolute stereochemistry of 10a as (1R,2R).

Example 12

Preparation of (1R,2R)/(1S,2R) 1-Boc-amino-2-ethylcyclopropylcarboxylic acid: (12a)

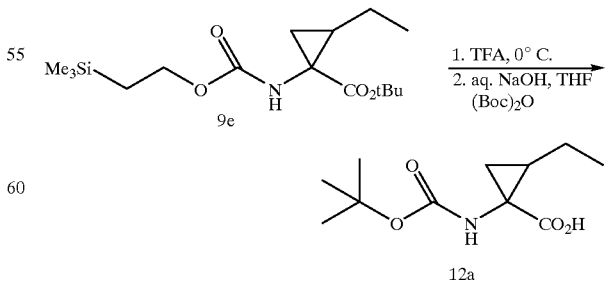

The carbamate 9e from Example 9 (2.6 g, 7.88 mmol) was stirred for 40 min in TFA at 0° C. The mixture was then concentrated and diluted with THF (10 mL). An aqueous NaOH solution (700 mg, 17.5 mmol in 8.8 mL of H2O) was added followed by a THF (13 mL) solution of (Boc)₂O (2.06 g, 9.44 mmol, 1.2 eq.). The reaction mixture was stirred overnight at RT (the pH was maintained at 8 by adding a 10% aqueous NaOH solution when needed), then diluted with H₂O, washed with Et₂O (3×) and acidified at 0° C. with a 10% aq. citric acid solution. The aqueous layer was extracted with EtOAc (3×) and successively washed with H₂O (2×) and brine. After the usual treatment (MgSO₄, filtration and concentration) the desired Boc-protected amino acid (12a) (788 mg, 3.44 mmol, 44% yield) was isolated. ¹H NMR (CDCl₃) δ5.18 (bs, 1H), 1.64–1.58 (m, 2H), 1.55–1.42 (m, 2H), 1.45 (s, 9H), 1.32–1.25 (m, 1H), 0.99 (t, 3H, J=7.3 Hz).

Preparation of (1R,2R)/(1S,2R)-1-Boc-amino-2-ethylcyclopropylcarboxylic acid methyl ester: (12b)

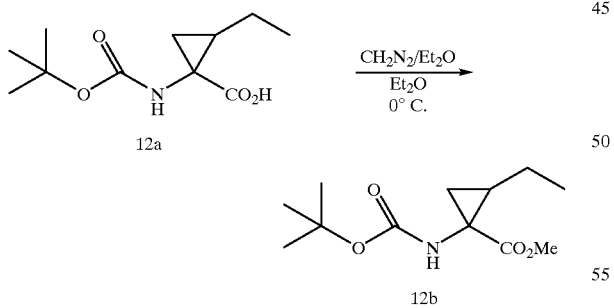

The Boc derivative 12a (0.30 g, 1.31 mmol) was dissolved in Et₂O (10 mL) and treated with freshly prepared diazomethane in Et₂O at 0° C. until the yellow color of a slight excess of diazomethane remained. After stirring for 20 min at RT the reaction mixture was concentrated to dryness to give 12b as a clear colorless oil (0.32 g, 100%). ¹H NMR (CDCl₃) δ5.1 (bs, 1H), 3.71 (s, 3H), 1.62–1.57 (m, 2H), 1.55 (s, 9H), 1.53–1.43 (m, 1H), 1.28–1.21 (m, 2H), 0.95 (t, J=7.3 Hz, 3H).

Example 13

Enzymatic resolution of methyl (1R,2R)/(1S,2R) Boc-1-amino-2-ethylcyclopropyl carboxylate

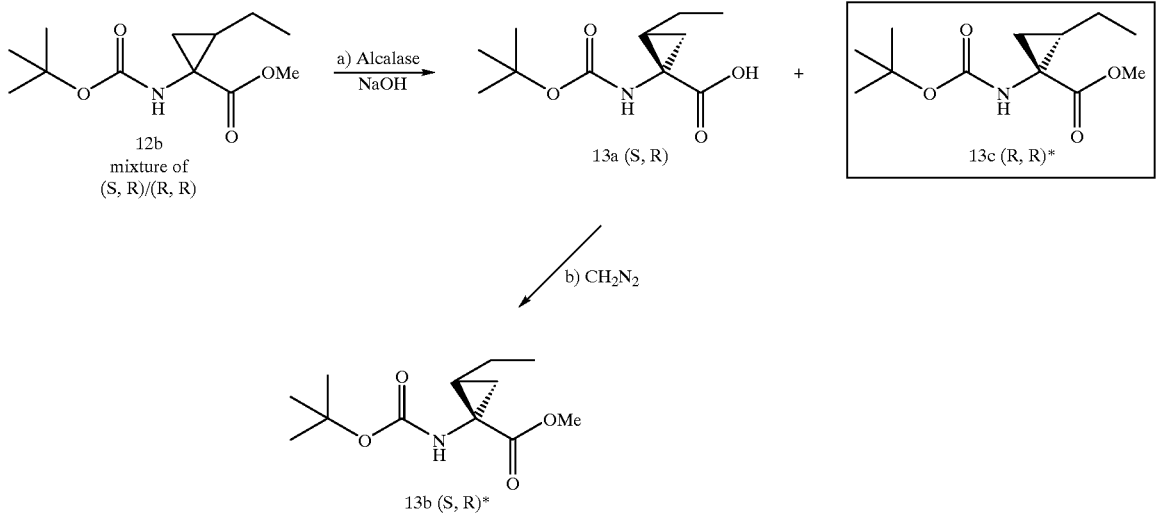

*Analysis by HPLC using Chiralcel® OD-H column
**Other esters also acceptable (eg. Et)

a) The enantiomeric mixture of (1S,2R)/(1R,2R) 1-Boc-amino-2-ethylcarboxylic acid methyl ester of Example 10 (0.31 g, 1.27 mmol) was dissolved in acetone (3 mL) and then diluted with water (7 mL) while being rapidly stirred. The pH of the solution was adjusted to 7.5 with 0.05M aqueous NaOH before Alcalase® [2.4 L extract from Novo Nordisk Industrials] (300 mg) was added. During incubation pH was stabilized with NaOH and a pH stat was set up to monitor the addition of the NaOH solution. After 40 h the mixture was diluted with EtOAc and H₂O (with 5 mL sat. NaHCO₃) and the phases separated. The aqueous phase was acidified with 10% aqueous HCl and extracted with EtOAc, dried (MgSO₄), filtered and concentrated to give acid 13a (48.5 mg). The absolute stereochemistry was determined using the correlation described in Examples 10 and 11.

b) Treatment of an aliquot of acid 13a with diazomethane in Et₂O to give the methyl ester followed by analysis by HPLC using a chiral column [Chiralcel® OD-H, 2.5% Isopropanol/hexane, isocratic] showed a 51:1 ratio of the (S,R) isomer.

Example 14

Synthesis of (1R,2S)/(1S,2S) 1-amino-2-ethylcyclopropyl carboxylic acid

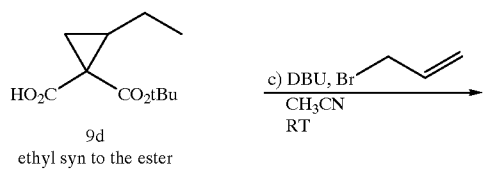

9d
ethyl syn to the ester

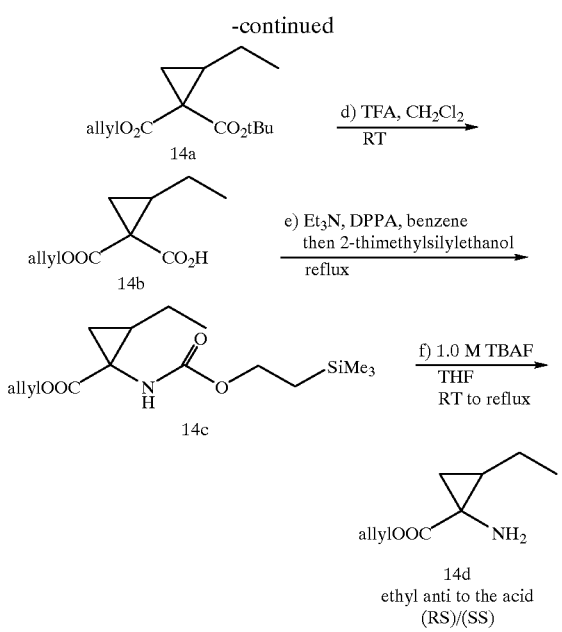

Starting from acid 9d described in Example 9:

c) To 9d (1.023 g, 4.77 mmol) in CH$_3$CN (25 mL) were successively added DBU (860 μL, 5.75 mmol, 1.2 eq.) and allyl bromide (620 μL, 7.16 mmol, 1.5 eq.). The reaction mixture was stirred for 4 h at RT and then concentrated. The residue was diluted with Et$_2$O and successively washed with a 10% aq. citric. acid solution (2×), H$_2$O, saturated aqueous NaHCO$_3$, H$_2$O (2×) and brine. After the usual treatment (MgSO$_4$, filtration and concentration) the desired ester 14a was isolated (1.106 g, 3.35 mmol, 91% yield) as a colorless oil. MS (FAB) 255 (MH$^+$); $^1$H NMR (CDCl$_3$) δ5.96–5.86 (m, 1H), 5.37–5.22 (m, 2H), 4.70–4.65 (m, 1H), 4.57–4.52 (m, 1H), 1.87–1.79 (m, 1H), 1.47 (s, 9H), 1.45–1.40 (m, 1H), 1.33–1.24 (m, 3H), 1.03 (t, J=7.3 Hz, 3H).

d) To ester 14a (1.106 g, 4.349 mmol) in dry CH$_2$Cl$_2$ (5 mL) at RT was added TFA (5 mL). The reaction mixture was stirred for 1.5 h and then concentrated to afford 14b (854 mg, 4.308 mmol, 99% yield). MS (FAB) 199 (MH$^+$); $^1$H NMR (CDCl$_3$) δ5.99–5.79 (m, 1H), 5.40–5.30 (m, 2H), 4.71–4.62 (m, 2H), 2.22–2.00 (m, 2H), 1.95–1.88 (m, 1H), 1.84–1.57 (m, 2H), 0.98 (t, J=7.3 Hz, 3H).

e) To acid 14b (853 mg, 4.30 mmol) in dry benzene (14.8 mL) were successively added Et$_3$N (684 μL, 4.91 mmol, 1.14 eq.) and DPPA (992 μL, 4.60 mmol, 1.07 eq.). The reaction mixture was refluxed for 4.5 h then 2-trimethylsilylethanol (1.23 mL, 8.58 mmol, 2.0 eq.) was added. The reflux was maintained overnight then the reaction mixture was diluted with Et$_2$O and successively washed with a 10% aqueous citric acid solution, water, saturated aq. NaHCO$_3$, water (2×) and brine. After the usual treatment (MgSO$_4$, filtration, concentration) the residue was flash chromatographed (5 cm, 10 to 15% AcOEt-hexane) to afford carbamate 14c (1.212 g, 3.866 mmol, 90% yield) as a pale yellow oil. MS (FAB) 314 (MH$^+$); $^1$H NMR (CDCl$_3$) δ5.93–5.84 (m, 1H), 5.32–5.20 (m, 2H), 5.05 (bs, 1H), 4.60–4.56 (m, 2H), 4.20–4.11 (m, 2H), 1.71–1.60 (m, 3H), 1.39–1.22 (m, 1H), 1.03 (t, J=7.6 Hz, 3H), 0.96–0.86 (m, 1H), 0.04 (s, 9H).

f) To carbamate 14c (267 mg, 0.810 mmol) was added a 1.0 M TBAF solution in THF (1.62 mL, 1.62 mmol, 2.0 eq.). The reaction mixture was stirred overnight at RT, refluxed for 30 min and then diluted with AcOEt. The solution was successively washed with water (2×) and brine. After the usual treatment (MgSO$_4$, filtration and concentration) the desired amine 14d was isolated (122 mg, 0.721 mmol, 89% yield) as a pale yellow liquid. $^1$H NMR (CDCl$_3$) δ5.94–5.86 (m,1H), 5.31–5.22 (m, 2H), 4.58 (d, J=5.7 Hz, 2H), 1.75 (bs, 2H), 1.61–1.53 (m, 2H), 1.51–1.42 (m, 2H), 1.00 (t, J=7.3 Hz, 3H), 0.70–0.62 (m, 1H).

Example 15

Synthesis of ethyl-(1R,2S)/(1S,2S)-1-amino-2-vinylcyclopropyl carboxylate

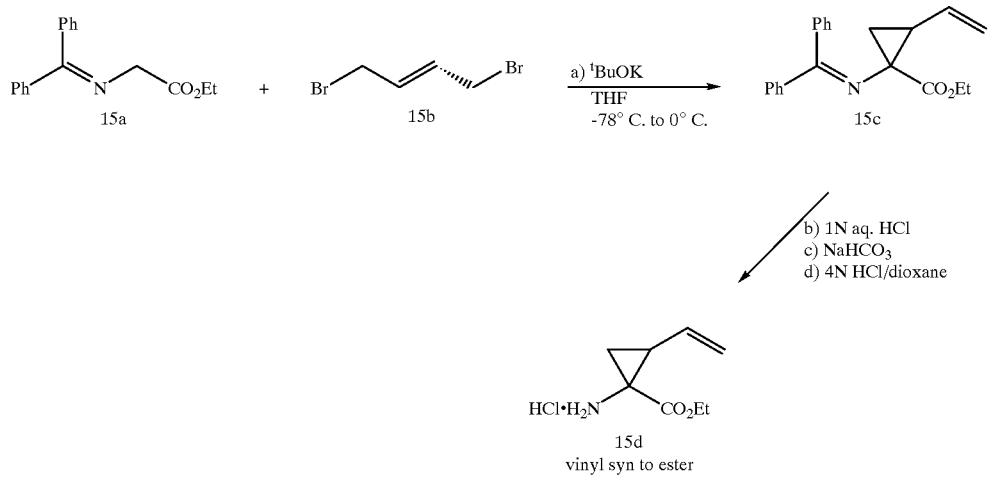

a) To a THF solution (180 mL) of potassium tert-butoxide (4.62 g, 41.17 mmol, 1.1 eq.) at −78° C. was added commercially available imine 15a (10.0 g, 37.41 mmol) in THF (45 mL). The reaction mixture was warmed to 0° C. and stirred at this temperature for 40 min. The mixture was then cooled back to −78° C. for the addition of 1,4-dibromobutene 15b (8.0 g, 37.40 mmol) and then stirred at 0° C. for 1 h and cooled back to −78° C. for the addition of potassium tert-butoxide (4.62 9, 41.17 mmol, 1.1 eq.). The reaction mixture was finally stirred one more hour at 0° C. and concentrated to yield compound 15c.

b, c, d) 15c was taken up in Et$_2$O (265 mL) and treated with a 1N aq. HCl solution (106 mL). After 3.5 h at RT, the layers were separated and the aqueous layer was washed with Et$_2$O (2×) and basified with a saturated aq. NaHCO$_3$ solution. The desired amine was extracted with Et$_2$O (3×) and the combined organic extract was washed with brine. After the usual treatment (MgSO$_4$, filtration and concentration) the residue was treated with a 4N HCl solution in dioxane (187 mL, 748 mmol). After concentration, hydrochloride salt 15d was isolated as a brown solid (2.467 g, 12.87 mmol, 34% yield). $^1$H NMR (CDCl$_3$) δ9.17 (bs, 3H), 5.75–5.66 (m, 1H), 5.39 (d, J=17.2 Hz, 1H), 5.21 (d, J=10.2 Hz, 1H), 4.35–4.21 (m, 2H), 2.77–2.70 (m, 1H), 205 (dd, J=6.4, 10.2 Hz, 1H), 1.75 (dd, J=6.4, 8.3 Hz,1H), 1.33 (t, J=7.0 Hz, 3H).

Example 16

Preparation of (1R,2S/1S,2S)-1-Boc-amino-2-vinylcyclopropyl carboxylic acid ethyl ester

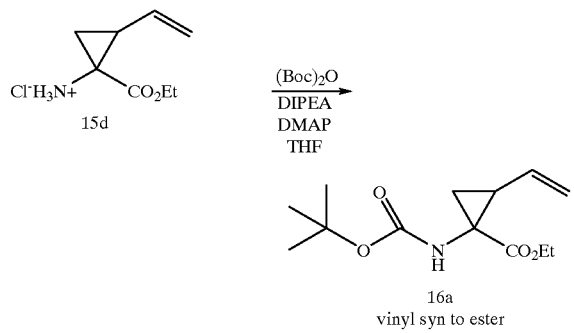

The hydrochloride salt 15d (1.0 g, 5.2 mmol) and (Boc)$_2$O (1.2 g, 5.7 mmol) were dissolved in THF (30 mL) end treated with DMAP (0.13 g, 1.04 mmol, 0.2 equiv.) and diisopropylethylamine (2.8 mL, 15.6 mmol). The reaction mixture was stirred 24 h before being diluted with EtOAc (40 mL) and washed successively with sat. NaHCO$_3$ (aq), 5% aqueous HCl, and sat. brine. The organic phase was dried (MgSO$_4$), filtered and concentrated to give after purification by flash chromatography (15% EtOAc/hexane), 16a (0.29 g, 23%). $^1$H NMR (CDCl$_3$) δ5.80–5.72 (m, 1H), 5.29–5.25 (dd, J=17.2, 17.2 Hz, 1H), 5.24–5.1 (bs, 1H), 5.10 (dd, J=9.2, 9.2 Hz, 1H), 4.22–4.13 (m, 2H), 2.15–2.04 (m, 1H), 1.85–1.73 (bs, 1H), 1.55–1.5 (m, 1H), 1.49 (s, 9H), 1.26 (t, J=7.3 Hz, 3H).

Example 17

Enzymatic resolution of ethyl (1R,2S)/(1S,2S) 1-amino-2-vinylcyclopropyl carboxylate

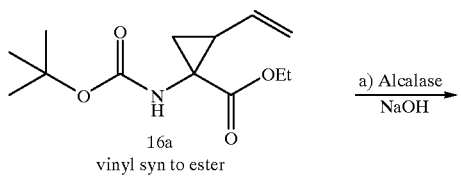

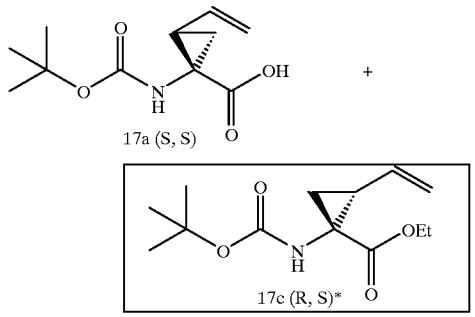

*Analysis by HPLC using Chiralcel® OD-H column a) Racemic derivative 17a (0.29 g, 1.14 mmol) was dissolved in acetone (5 mL) and diluted with H$_2$O (10 mL). The pH was adjusted with 0.2N aqueous NaOH to 7.2 before Alcalase® was added (300 mg). To keep the pH constant during incubation, a NaOH solution was added by a pH stat titrator over 9 days until the theoretical amount of base had been added. Following acid/base extraction as described in Example 13, the unhydrolyzed ester (0.15 g, 100%) and the hydrolyzed material (0.139 g, 95%) were isolated. Analysis of the unhydrolyzed ester by HPLC using a chiral column showed a ratio of 43:1 of the desired compound 17c that was assigned the (R,S) stereochemistry based on chemical correlation as described in Examples 10 and 11.

Conditions for HPLC analysis: Chiralcel® OD-H (4.6 mm×25 cm), isocratic conditions using a mobile phase of 2.5% isopropanol/hexane.

Example 18

Resolution of (1R,2S)/(1S,2S) 1-amino-2-vinylcyclopropyl carboxylate by crystallization with dibenzoyl-D-tartaric acid (18)

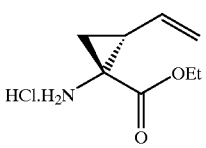

To a solution of crude racemic (1S,2S and 1R,2S) ethyl 1-amino-2-vinylcyclopropyl carboxylate [obtained from N-(diphenylmethylene)glycine ethyl ester (25.0 g, 93.5 mol) as described in Example 15] in EtOAc (800 mL) was added dibenzoyl-D-tartaric acid (33.5 g, 93.5 mol). The mixture was heated to reflux, left at RT for 15 min then cooled to 0° C. A white solid was obtained after 30 min. The solid was filtered, washed with EtOAc (100 mL) and air-dried. The solid was suspended in acetone (70 mL), sonicated and filtered (3×). The solid was next recrystallized twice in hot acetone (crop A). The mother liquors were concentrated and the residue was recrystallized three times in hot acetone (crop B). The two crops of the amorphous white solids of dibenzoyl-D-tartaric acid salt were combined (5.53 g) and suspended in a mixture of Et$_2$O (250 mL) and saturated NaHCO$_3$ solution (150 mL). The organic layer was washed with brine, dried (MgSO$_4$) and filtered. The filtrate was diluted with 1 N HCl/Et$_2$O (100 mL) and concentrated under reduced pressure. The oily residue was evaporated with CCl$_4$ to afford ethyl 1(R)-amino-2(S)-vinyl cyclopropanecarboxylate hydrochloride (940 mg, 11% yield) as a white hygroscopic solid: [α]$_D^{25}$ +39.5° C. (c 1.14 MeOH); [α]$_{365}^{25}$ +88.5° C. (c 1.14 MeOH); $^1$H NMR (DMSO-d$_6$) δ9.07 (broad s, 2H), 5.64 (ddd, J=17.2, 10.4, 8.7 Hz, 1H), 5.36 (dd, J=17.2, 1.6 Hz, 1H), 5.19 (dd, J=10.4, 1.6 Hz, 1H), 4.24–4.16 (m, 2H), 2.51–2.45 (m, peaks hindered by DMSO, 1H), 1.84 (dd, J=10.0, 6.0 Hz, 1H), 1.64 (dd, J=8.3, 6.0 Hz, 1H), 1.23 (t, J=7.1 Hz, 3H); MS (ESI) m/z 156 (MH)$^+$; the enantiomeric purity was determined to be 91% ee by HPLC analysis (CHIRALPAK AS® column, Hex:/-PROH) of the Boc derivative.

Example 19

Preparation of (1R,2S)/(1S,2S)-1-amino-2-vinylcyclopropane carboxylic acid methyl-ester hydrochloride (19f)

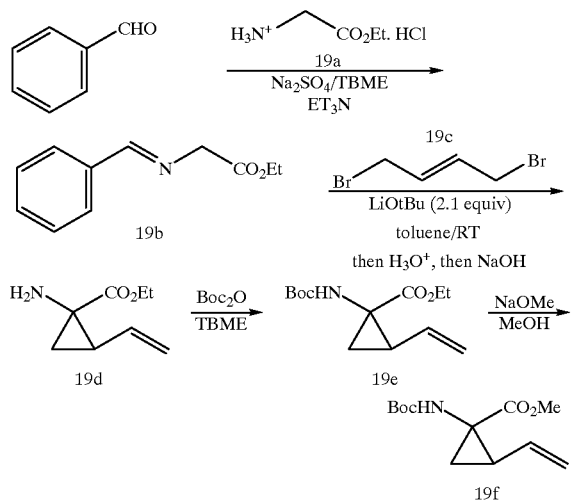

Preparation of imine 19b

Glycine ethyl ester hydrochloride 19a (1519.2 g, 10.88 mole, 1.0 equiv) was suspended in tert-butylmethyl ether (8 L). Benzaldehyde (1155 g, 10.88 mole, 1 equiv) and anhydrous sodium sulfate (773 g, 5.44 mole, 05 equiv) were added and the mixture cooled to 5° C. in an ice-water bath. Triethylamine (2275 mL, 16.32 mole, 1.5 equiv) was added dropwise over 15 min (use 0.5 L of tert-butylmethyl ether for rinses) and the mixture stirred for 40 h at room temperature. The reaction was then quenched by addition of ice-cold water (5 L) and the organic layer was separated. The aqueous phase was extracted with tert-butylmethyl ether (1 L) and the combined organic phases washed with a mixture of saturated NaHCO$_3$ (400 mL) and water (1.6 L), and then brine. The solution was dried over MgSO$_4$, concentrated under reduced pressure and the residual yellow oil dried to constant weight under vacuum. Imine 19b was obtained as a thick yellow oil that solidifies at −20° C. (2001 g, 96% yield): $^1$H NMR (CDCl$_3$, 400 MHz) δ8.30 (s, 1H), 7.79 (m, 2H), 7.48–7.39 (m, 3H), 4.40 (d, J=1.3 Hz, 2H), 4.24 (q, J=7 Hz, 2H), 1.31 (t, J=7 Hz, 3H).

Preparation of racemic N-Boc-(1R,2S)/(1S, 2S)-1-amino-2-vinylcyclopropane carboxylic acid ethyl-ester hydrochloride 19e Lithium tert-butoxide (4.203 g, 52.5 mmol, 2.1 equiv) was suspended in dry toluene (60 mL). Imine 19b (5.020 g, 26.3 mmol, 1.05 equiv) and dibromide 19c (5.348 g, 25 mmol, 1 equiv) were dissolved in dry toluene (30 mL) and this solution added dropwise over 30 min to the stirred solution of LiOtBu at room temperature. After completion, the deep red mixture was stirred for an additional 10 min and quenched by addition of water (50 mL) and tert-butylmethyl ether (TBME, 50 mL). The aqueous phase was separated and extracted a second time with TBME (50 mL). The organic phases were combined, 1 N HCl (60 mL) was added and the mixture stirred at room temperature for 2 h. The organic phase was separated and extracted with water (40 mL). The aqueous phases were then combined, saturated with salt (35 g) and TBME (50 mL) was added. The stirred mixture was then basified to pH 13–14 by careful addition of 10 N NaOH. The organic layer was separated and the aqueous phase extracted with TBME (2×50 mL). The organic extracts containing free amine 19d were combined and ditertbutyl-dicarbonate (5.46 g, 25 mmol, 1 equiv) was added. After stirring overnight at room temperature, TLC showed some unreacted free amine. Additional ditertbutyldicarbonate (1.09 g, 5 mmol, 0.2 equiv) was added and the mixture refluxed for 2 h, at which point, TLC analysis indicated complete conversion of 19d to carbamate 19e. The solution was cooled to room temperature, dried over MgSO$_4$ and concentrated under reduced pressure. The residue was purified by flash chromatography using 10% then 20% EtOAc/hexane as eluent. Purified 19e was obtained as a clear yellow oil which slowly solidifies under vacuum (4.014 g, 63% yield).

$^1$H NMR (CDCl$_3$, 400 MHz) δ5.77 (ddd, J=17, 10, 9 Hz, 1H), 5.28 (dd, J=17, 1.5 Hz, 1H), 5.18 (broad s, 1H), 5.11 (dd J=10, 1.5 Hz, 1H), 4.24–4.09 (m, 2H), 2.13 (q, J=8.5 Hz, 1H), 1.79 (broad m, 1H); 1.46 (m, 1H), 1.45 (s, 9H), 1.26 (t, J=7 Hz, 3H).

Preparation of title compound 19f via trans-esterification of 19e

Ethyl ester 19e (10.807 g, 42.35 mmol) was dissolved in dry methanol (50 mL) and a solution of sodium methoxide in MeOH (25% w/w, 9.7 mL, 42 mmol, 1 equivalent) was added. The mixture was heated at 50° C. for 2 h, at which point TLC analysis indicated complete trans-esterification (19e R$_f$ 0.38, 19f R$_f$ 0.34 in 20% EtOAc/hexane); The reaction mixture was cooled to room temperature and acidified to pH 4 using 4N HCl in dioxane. Precipitated NaCl was removed by filtration (use tert-butylmethyl ether for washings) and volatiles removed under reduced pressure. Tert-butylmethyl ether (100 mL) was added to the residue and solids removed by filtration. Evaporation of the filtrate under reduced pressure and drying under vacuum gave pure methyl ester 19f (10.11 g, 99% yield).

$^1$H NMR (CDCl$_3$, 400 MHz) δ5.75 (ddd, J=17, 10, 9 Hz, 1H), 5.28 (dd, J=17, 1 Hz, 1H), 5.18 (broad s, 1H), 5.11 (ddd, J=10, 1.5, 0.5 Hz, 1H), 3.71 (s, 3H), 2.14 (q, J=9 Hz, 1H), 1.79 (broad m, 1H), 1.50 (broad m, 1H), 1.46 (s, 9H).

Example 20

Enzymatic resolution of (1R,2S)-1-amino-2-vinylcyclopropane carboxylic acid methyl-ester hydrochloride

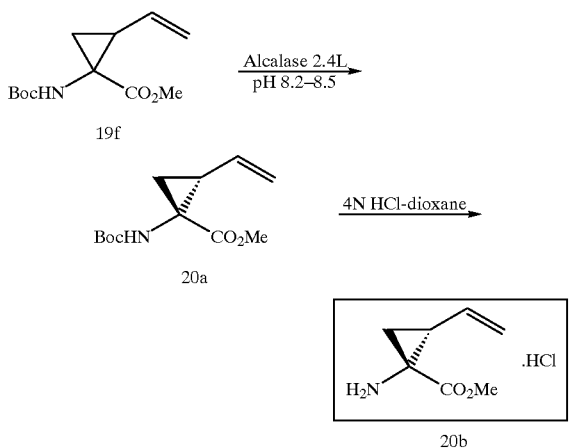

Preparation of N-Boc-(1R,2S)-1-amino-2-vinylcyclopropane carboxylic acid methyl ester 20a Racemic ester 19f (0.200 g, 0.83 mmol) was dissolved in acetone (3 mL) and water (7 mL) was added. 0.05 M NaOH (1 drop) was added to bring the pH of the solution to ~8 and then Alcalase® 2.4 L (Novo Nordisk Biochem, 0.3 g in one mL of water) was added. The mixture was stirred vigorously at room temperature, maintaining the pH of the solution at 8 using an automatic titrator. At beginning of day 4 and 5 of stirring at pH 8, additional enzyme solution was added (2×0.3 g). After a total of 5 days, a total of 8.3 mL of 0.05 M NaOH was consumed. The reaction mixture was diluted with EtOAc and water and the organic phase separated. After washing with brine, the organic extract was dried ($MgSO_4$) and concentrated under vacuum. Compound 20a (0.059 g, 30% yield) was obtained as a clear oil: $^1$H NMR identical to that of compound 19f. HPLC (Chiralcel ODH, 4.6×250 mm, isocratic 1% EtOH in hexane, 0.8 mL/min flow rate): (1R,2S)-2 $R_t$ 19.3 min (97%); (1S,2R)-2 $R_t$ 17.0 min (3%).

Preparation of (1R,2S)-1-amino-2-vinylcyclopropane carboxylic acid methyl ester hydrochloride 20b Compound 20a (39.96 g, 165.7 mmol) was dissolved in dioxane (25 mL) and the solution added dropwise with stirring to 4 N HCl in dioxane (Aldrich, 250 mL). After 45 min, TLC analysis indicated complete deprotection. Volatiles were removed under reduced pressure, and the residue co-evaporated twice with MeOH (2×100 mL). Ether (300 mL) and MeOH (10 mL) were added to the brown, oily residue and the mixture stirred overnight at room temperature resulting in the precipitation of a semi-solid. Additional MeOH (15 mL) was added and stirring continued for 6 h, at which point a yellowish solid was collected by filtration. The product was washed with 5% MeOH in ether (50 mL) and ether (2×50 mL), and dried in vacuo to give compound 20b as a yellowish solid (22.60 g, 76% yield). Filtrates (including washings) were evaporated in vacuum to give additional 20b as a brown oil (7.82 g, 26% yield). Both fractions were pure enough for use in the synthesis of HCV protease inhibitors: $[\alpha]_D^{25}$ +38.2° (c 1.0, MeOH).

$^1$H NMR (400 MHz, DMSO-$d_6$) δ9.15 (broad s, 3H), 5.65 (ddd, J=17, 10, 9 Hz, 1H), 5.36 (dd, J=17, 1.5 Hz, 1H), 5.19 (dd, J=10, 1.5 Hz, 1H), 3.74 (s, 3H), 2.50 (q, overlap with DMSO signal, J=9 Hz, 1H), 1.86 (dd, J=10, 6 Hz, 1H), 1.64 (dd, J=8, 6 Hz, 1H).

Example 21

Synthesis of 1-aminocyclobutyl carboxylic acid methyl ester

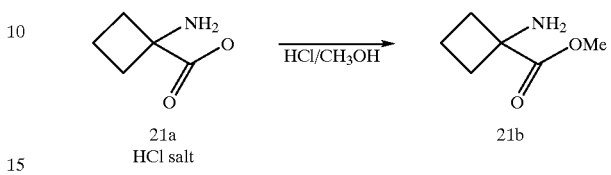

1,1-aminocyclobutanecarboxylic acid was prepared according to Kavin Douglas; Ramaligam Kondareddiar; Woodard Ronald, Synth. Commun. (1985), 15 (4), 267–72. The amino acid salt (21a) (1.00 g., 6.6 mmoles) was stirred in dry methanol (40 ml) at −20° C. and mixture saturated with dry hydrogen chloride to yield (21b). Stirring of this mixture was continued for 4 h. The hot solution was filtered and filtrate concentrated (Rotavap, 30° C.) to leave a residue which upon trituration in ethyl ether afforded a white powder (0.907 g., 83% ) after filtration and drying. $^1$H NMR (400 MHz, $D_2$) δ$CH_3O$ (3H, s, 3.97 ppm); $CH_2$ (2H, m, 2.70–2.77 ppm); $CH_2$ (2H, m, 2.45–2.53 ppm) and $CH_2$ (2H, m, 2.14–2.29 ppm).

Tripeptides

Example 22

General Procedure for Coupling Reactions Done on Solid Support

The synthesis was done on a parallel synthesizer model ACT396 from Advanced ChemTech® with the 96 well block. Typically, 24 peptides were synthesized in parallel using standard solid-phase techniques. The starting (Fmoc-amino)cyclopropane (optionally substituted) carboxylic acid-Wang resin were prepared by the DCC/DMAP coupling method (Atherton, E; Scheppard, R. C. *Solid Phase Peptide Synthesis, a Practical Approach;* IRL Press: Oxford (1989); pp 131–148).

Each well was loaded with 100 mg of the starting resin (approximately 0.05 mmol). The resins were washed successively with 1.5 mL portions of NMP (1×) and DMF (3×). The Fmoc protecting group was removed by treatment with 1.5 mL of a 25% v/v solution of piperidine in DMF for 20 minutes. The resins were washed with 1.5 mL portions of DMF (4×), MeOH (3×) and DMF (3×). The coupling was done in DMF (350 µL), using 400 µL (0.2 mmol) of a 0.5M solution of Fmoc-amino acid/HOBt hydrate in DMF, 400 µL (0.4 mmol) of a 1M solution of DIPEA in DMF and 400 µL (0.2 mmol) of a 0.5M solution of TBTU in DMF. After shaking for 1 hour, the wells were drained, the resins were washed with 1.5 mL of DMF and the coupling was repeated once more under the same conditions. The resins were then washed as described above and the cycle was repeated with the next amino acid.

The capping groups were introduced in two ways:
1. In the form of a carboxylic acid using the protocol described above (for example acetic acid) or,
2. As an acylating agent such as an anhydride or an acid chloride. The following example illustrates the capping with succinic anhydride: After the Fmoc deprotection and subsequent washing protocol, DMF was added (350 µL), followed by 400 µL each of a DMF solution of succinic anhydride (0.5 M, 0.2 mmol) and DIPEA (1.0 M, 0.4 mmol). The resins were stirred for 2 h and a recoupling step was performed. At the end of the synthesis the resin was washed with 1.5 mL portions of DCM (3×), MeOH (3×), DCM (3×), and were dried under vacuum for 2 h. The cleavage from the resin and concomitant side chain deprotection was effected by the addition of 1.5 mL of a mixture of TFA, H₂O, DTT and TIS (92.5:2.5:2.5:2.5). After shaking for 2.5 h, the resin was filtered and washed with 1.5 mL of DCM. The filtrates were combined and concentrated by vacuum centrifugation. Each compound was purified by preparative reversed phase HPLC using a C18 column (22 mm by 500 mm). The product-containing fractions were identified by MALDI-TOF mass spectrometry, combined and lyophilized.

Example 23
General Procedure for Coupling Reactions Done in Solution
{See also R. Knorr et al., Tetrahedron Letters, (1989), 30, 1927.}

The reactants, i.e. a free amine (1 eq.) (or its hydrochloride salt) and the free carboxylic acid (1 eq.) were dissolved in CH₂Cl₂, CH₃CN or DMF. Under a nitrogen atmosphere, four equivalents of N-methylmorpholine and 1.05 equivalents of the coupling agent were added to the stirred solution. After 20 min, one equivalent of the second reactant, i.e. a free carboxylic acid was added. (Practical and efficient coupling reagents for this purpose are (benzotriazol-1-yloxy)tris-(dimethylamino)phosphonium hexafluorophosphate (HOBT) or preferably 2-(1H-benzotriazol-1-yl)-N,N,N',N'-tetramethyluronium tetrafluoroborate (TBTU) or O-(7-azabenzotriazol-1-yl)-N,N,N',N'-tetramethyluronium tetrafluoroborate (HATU). The reaction was monitored by TLC. After completion of the reaction, the solvent was evaporated under reduced pressure. The residue was dissolved in EtOAc. The solution was washed successively with 10% aqueous citric acid, saturated aqueous NaHCO₃ and brine. The organic phase was dried (MgSO₄), filtered and concentrated under reduced pressure. When the residue was purified, it was done by flash chromatography as defined above.

Example 24
Synthesis of Compound 304

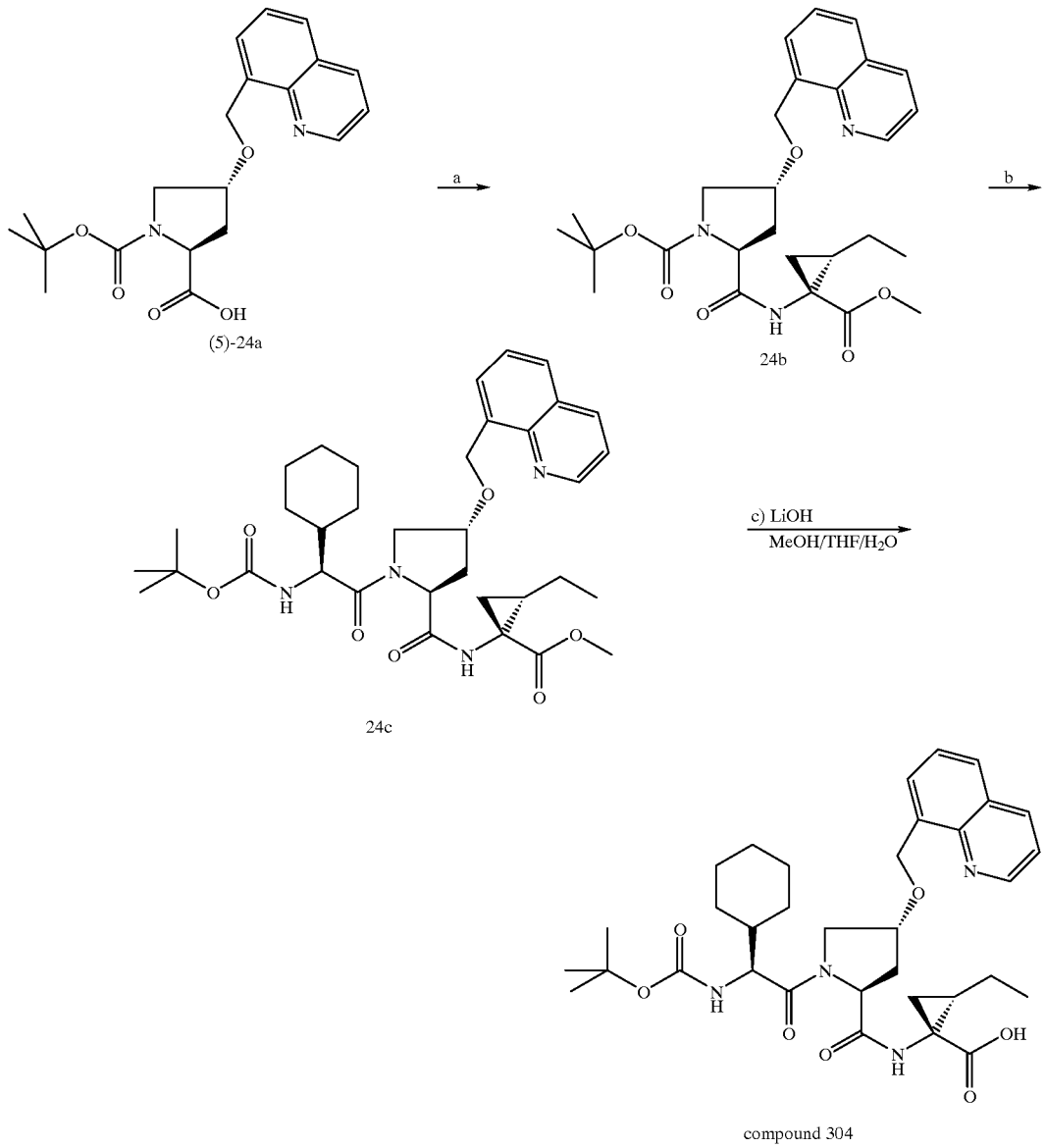

a) The (R,R) isomer of Boc-Et-Acca-OMe 13c (0.12 g, 0.49 mmol) obtained from enzymatic resolution (Example 13) was treated with 4N HCl/dioxane (45 min) before being concentrated in vacuo to give a white solid. To this HCl salt (ca. 0.49 mmol) was added TBTU (0.17 g, 0.54 mmol), the Boc-4(R)-(8-quinoline-methyloxy) proline 5 (from Example 5) (0.18 g, 0.49 mmol) and DIPEA (0.3 mL, 1.7 mmol) in MeCN (10 mL). The mixture was stirred at RT for 3.5 h before being concentrated in vacuo. The resulting material was dissolved in EtOAc and washed sequentially with saturated aqueous $NaHCO_3$ and brine. Dried ($MgSO_4$), filtered and concentrated to give 24b a white solid (0.122 g, 50%).

b) 24b (0.12 g, 0.25 mmol) was treated at RT with 4N HCl/dioxane (30 min) before being concentrated in vacuo. The resulting hydrochloride salt (ca. 0.25 mmol) was treated with Boc-Chg-OH.$H_2O$ (75 mg, 0.27 mmol), TBTU (87 mg, 0.27 mmol) in MeCN (10 mL) and finally at 0° C. with DIPEA (0.15 mL, 0.87 mmol). The residue was diluted with EtOAc, sequentially washed with saturated aqueous $NaHCO_3$, and brine, dried ($MgSO_4$), filtered and concentrated to give 24c as an off white solid (0.2 g). This material (0.14 g) was dissolved in DMSO and purified by preparative HPLC to give 24c as a white solid after lyophilization (35 mg, 33%). HPLC (98%); MS (FAB) m/z: 637.3 ($MH^+$); HRMS calcd for $C_{35}H_{48}N_4O_7$ ($MH^+$) 637.36011: found 637.36250; $^1$H-NMR (DMSO-$d_6$) shows a rotamer population, δ8.91 (2×d, J=4.1 and 4.1 Hz, 1H), 8.40–8.36 (m, 2H), 7.90 (d, J=7.6 Hz, 1H), 7.77 (d, J=7.0 Hz, 1H), 7.6–7.54 (m, 2H), 6.80 (d, J=8.6 Hz, 1H), 5.18 and 5.16 (2×s, 2H), 4.40 (bs, 1H), 4.31 (t, J=8.3 Hz, 1H), 4.12 (d, J=11.44 Hz, 1H), 4.03 (t, J=7.9 Hz, 1H), 3.78–3.72 (m, 1H), 3.56 (s, 3H), 2.35–2.27 (m, 1H), 2.06–1.97 (m, 1H), 1.71–1.55 (m, 10H), 1.53–1.38 (m, 2H), 1.26 (s, 9H), 1.18–1.06 (m, 2H), 1.02–0.93 (m, 2H), 0.89 (t, J=7.3 Hz, 3H).

compound 304:

c) To 24c (30 mg, ca. 0.047 mmol) was added MeOH (1 mL), THF (1 mL), and lithium hydroxide monohydrate (12 mg, 0.29 mmol) in $H_2O$ (1 mL). The clear solution was stirred rapidly for 48 h before being concentrated in vacuo. The crude peptide was dissolved in DMSO and purified by preparative HPLC to give compound 304 as a white solid after lyophilization (21 mg, 72%). HPLC (99%); MS (FAB) m/z: ($MH^+$) 623.3; HRMS calcd for $C_{34}H_{46}N_4O_7$ ($MH^+$) 623.34448, found: 623.34630, $^1$HNMR (DMSO-$d_6$) shows a rotamer population of 1:1, δ8.90 (2×d, J=4.1 Hz, 1H), 8.37 (d, J=8.3 Hz, 1H), 8.26 (s, 1H), 7.89 (d, J=8.3 Hz, 1H), 7.77 (d, J=6.7 Hz, 1H), 7.6–7.53 (m, 2H), 6.88 and 6.79 (2×d, J=8.6 and 7.9 Hz, 1H), 5.17 and 5.16 (2×s, 2H), 4.43–4.35 (bs, 1H), 4.29 (t, J=8.3 Hz, 1H), 3.82–3.71 (m, 1H), 2.35–2.27 (m, 1H), 2.06–1.97 (m, 1H), 1.72–1.53 (m, 10H), 1.52–1.44 (m, 2H), 1.37 and 1.29 (2×s, 9H), 1.18–1.05 (m, 3H), 1.0–0.94 (m,1H), 0.91 (t, J=7.3 Hz, 3H).

Example 25

Synthesis of compound 301

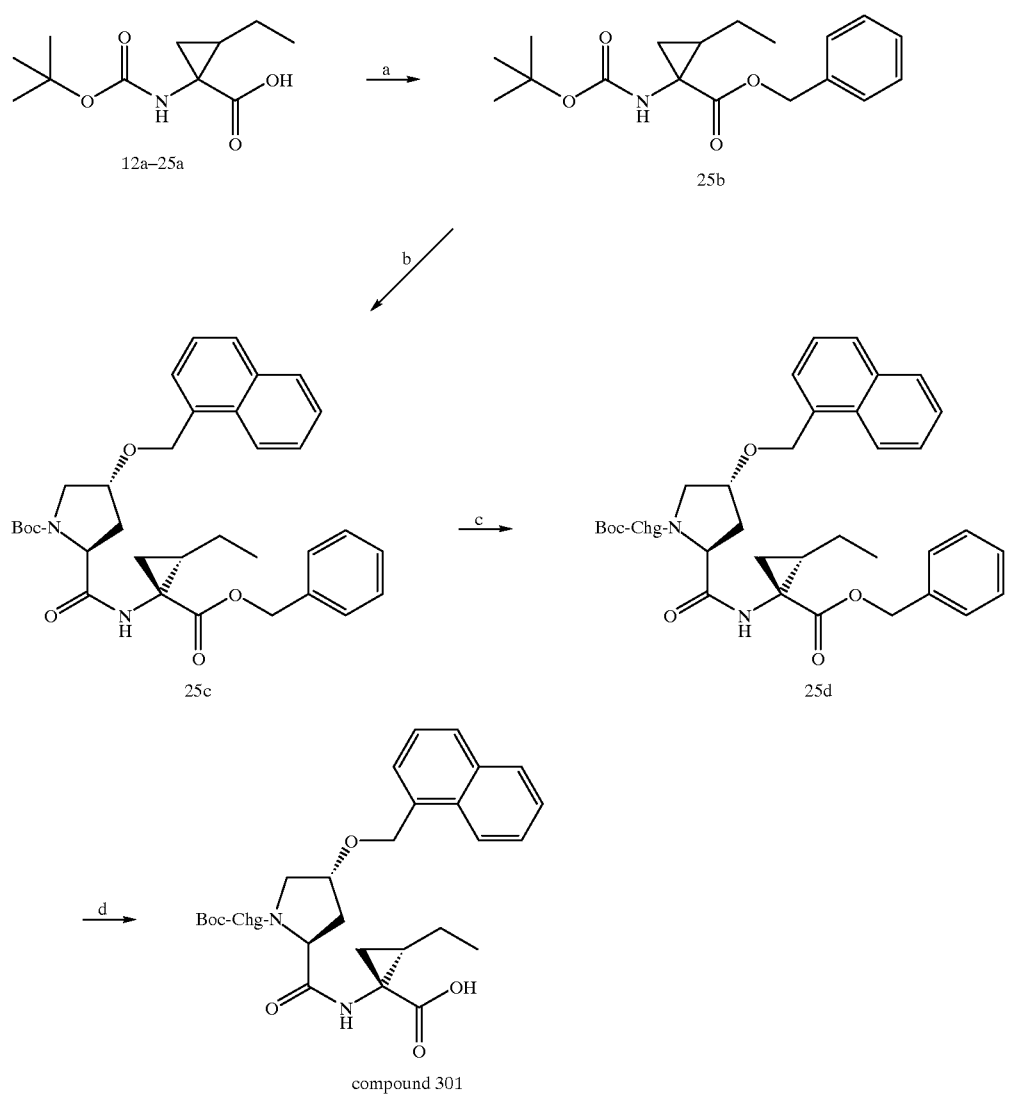

a) Compound 25a (=12a) (282 mg, 1.23 mmol) was suspended in anhydrous CH$_3$CN (6 mL). DBU (221 µL, 1.48 mmol) and benzylbromide (161 µL, 1.35 mmol) were added successively and the reaction mixture was stirred overnight at RT. The mixture was concentrated, the resulting oil was diluted with EtOAc and 10% aq. citric acid and successively washed with 10% citric acid (2x), saturated aq. NaHCO$_3$ (2x), water (2x) and brine (1x). The EtOAc layer was dried (MgSO$_4$), filtered and evaporated to dryness. The crude colorless oil was purified by flash chromatography (eluent— hexane:EtOAc; 95:5 to 90:10) to provide the benzylated product 25b as a colorless oil (368 mg ; 93%).

MS (FAB) 318.2 MH$^-$ 320.2 MH$^+$ 342.2 (M+Na)$^+$ $^1$H NMR (CDCl$_3$) δ7.37–7.28 (m, 5H), 5.22–5.10 (m, 1H), 5.19 (d, J=12 Hz, 1H), 5.16 (d, J=12 Hz, 1H, 1.60–1.40 (m, 4H), 1.39 (s, 9H), 1.31–1.22 (m, 1H), 0.91 (t, J=7.5, 14.5 Hz, 3H).

b) Compound 25b (368 mg, 1.15 mmol) was treated with 4N HCl/dioxane (6 mL) as described previously. The crude hydrochloride salt was coupled to compound 4 (from Example 4) (470.8 mg, 1.27 mmol) with NMM (507 µL, 4.61 mmol) and HATU (instead of TBTU, 525.6 mg, 1.38 mmol) in CH$_2$Cl$_2$ (6 mL) as described in Example 22 to yield the crude racemic dipeptide as an orange oil. The crude material was purified by flash chromatography (eluent— hexane:Et$_2$O; 50:50) to provide the pure dipeptide 25c (the less polar eluting spot) as a white foam (223 mg ; 68% of the theoretical yield).

MS 571.4 MH$^-$ 573.3 MH$^+$ 595.3 (M+Na)$^+$ $^1$H NMR (CDCl$_3$), ca. 1:1 mixture of rotamers, δ8.03 (b d, J=8 Hz, 1H), 7.86 (b d, J=7.5 Hz, 1H), 7.82 (b d, J=6.5 Hz, 1H), 7.61 (b s, 0.5H), 7.57–7.40(m, 4H), 7.31–7.21 (m, 5H), 6.48 (b s, 0.5H), 5.22–5.11 (m, 1H), 5.08–4.81 (m, 3H), 4.41–3.74 (m, 3H), 3.49–3.18 (m, 1H), 2.76–1.90 (m, 2H), 1.69–1.48 (m, 3H), 1.40 (s, 9H), 1.40–1.23 (m, 2H), 0.92 (t, J=7.5, 15 Hz, 3H).

c) The dipeptide 25c (170.1 mg, 0.297 mmol) was treated with 4N HCl/dioxane (2 mL) as described previously. The crude hydrochloride salt was coupled to Boc-Chg-OH (84.1 mg ,0.327 mmol) with NMM (130.7 µL, 1.19 mmol) and HATU (instead of TBTU, 135.5 mg; 0.356 mmol) in CH$_2$Cl$_2$ (2 mL) for 2.75 h at RT then worked up as described previously to provide the crude tripeptide 25d as an ivory foam (ca. 211.4 mg; 100%).

MS (FAB) 712.5 MH$^+$ compound 301:

d) The crude tripeptide 25d (ca.15.4 mg, 0.022 mmol) was dissolved in absolute ethanol (2 mL) and an estimated amount (tip of spatula) of both 10% Pd/C catalyst and ammonium acetate were added. The mixture was hydrogenated overnight under a hydrogen filled balloon at RT and atmospheric pressure. The reaction mixture was filtered through a 0.45 µm Millex® filter, evaporated to dryness then diluted with EtOAc and 10% aqueous citric add, and washed again with 10% aqueous citric acid (1x), water (2x) and brine (1x). The organic layer was dried (MgSO$_4$), filtered, evaporated to dryness and lyophilized to provide the tripeptide 301 as a white amorphous solid (11.0 mg; 82%).

MS (FAB) 622.5 MH+ 644.5 (M+Na)+

$^1$H NMR (DMSO), ca.1:4 mixture of rotamers, δ8.54 & 8.27 (s, 1H),8.06–7.99 (m, 1H), 7.96–7.91 (m, 1H), 7.87 (d, J=8 Hz, 1H), 7.57–7.42 (m, 4H), 6.81 (d, J=8 Hz, 1H), 4.99 (d, J=12 Hz, 1H), 4.88 (d, J=12 Hz, 1H), 4.46–4.19 (m, 2H), 4.17–4.02 (m, 2H), 3.88–3.67 (m, 1H), 2.28–2.19 (m, 1H), 2.05–1.93 (m, 1H), 1.73–1.43 (m, 8H), 1.32–1.07 (m, 6H), 1.28 (s, 9H), 1.03–0.85 (m, 2H), 0.91 (t, J=7.5, 15 Hz, 3H).

Example 26

Synthesis of compound 306

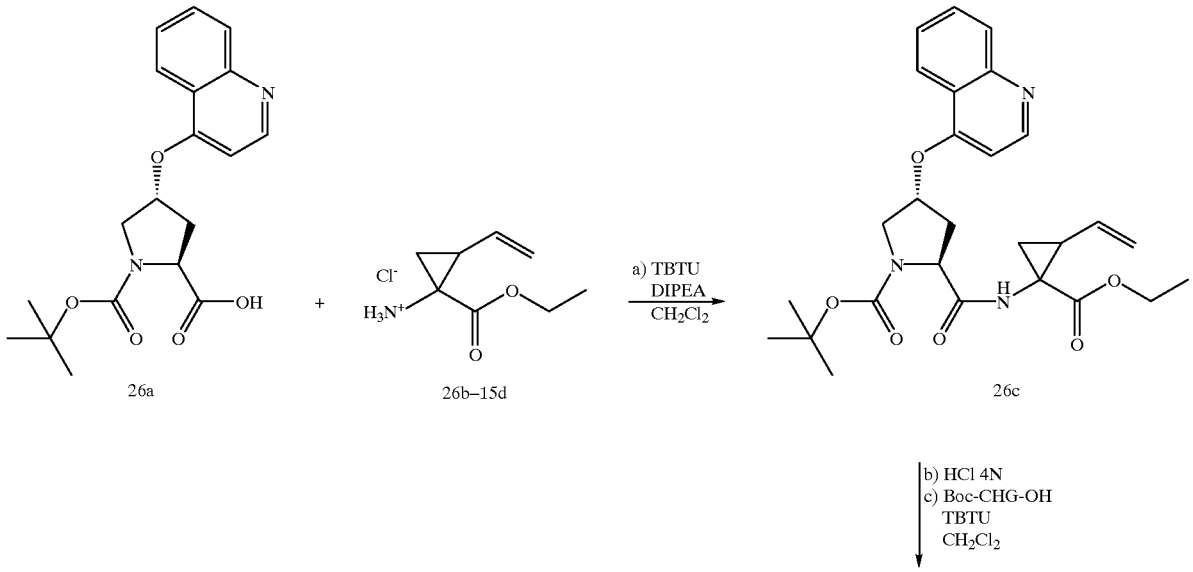

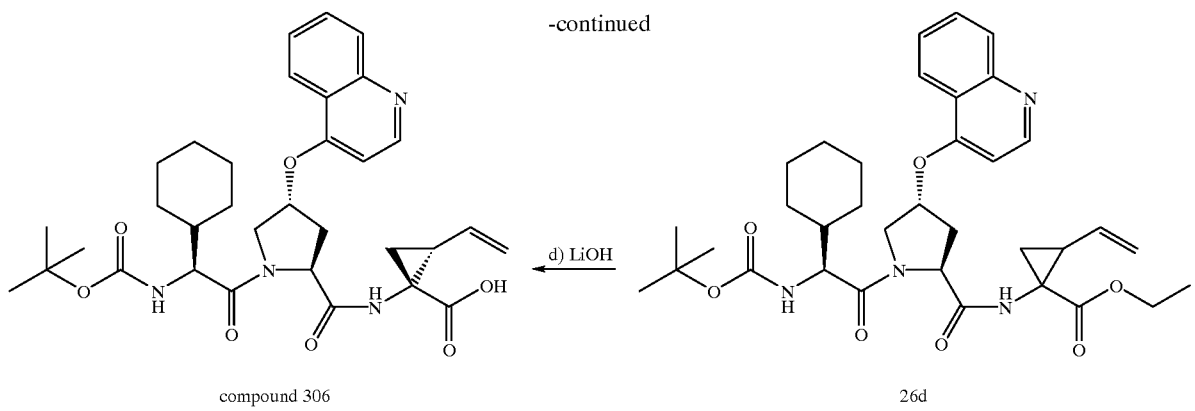

compound 306          26d a) The acid 26a (180 mg, 0.500 mmol) and the amine 15d (96 mg, 0.500 mmole) were coupled using TBTU (192 mg, 0.600 mmol) and DIPEA (226 mg, 1.75 mmol) in $CH_2Cl_2$ (10 mL) for 20 h. The reaction mixture was concentrated, taken up in ethyl acetate, washed twice with sat. $NaHCO_3$ and once with brine. The organic layer was dried on $MgSO_4$, filtered and concentrated to give 26c as a brown oil, used without purification in the next step.

b, c) The crude compound 26c (ca. 0.500 mmol) was stirred for 30 min in HCl 4N/dioxane (4 mL) and concentrated to dryness. The solid was taken up in $CH_2Cl_2$ (10 mL) and DIPEA (226 mg, 1.75 mmol) was added followed by Boc-Chg-OH monohydrate (138 mg, 0.500 mmol) and TBTU (192 mg, 0.600 mmol). The solution was stirred at RT for 5 h. The reaction mixture was concentrated, taken up in ethyl acetate, washed twice with sat. $NaHCO_3$ and once with brine. The organic layer was dried on $MgSO_4$, filtered and concentrated to give a brown oil, purified by flash chromatography to give 26d as a yellow oil, 204 mg, 64% over two couplings.

$^1$H NMR ($CDCl_3$) δ8.77–8.74 (m, 1 H), 8.14 (d, J=8 Hz, 1 H), 8.02 (d, J=9 Hz, 1H), 7.69 (dd, J=9, 7 Hz, 1 H), 7.52 (d, J=5 Hz, 1 H), 7.47 (dd, J=8, 7 Hz, 1 H), 6.78 (d, J=5 Hz, 1 H), 5.80–5.70 (m, 1 H), 5.35–5.27 (m, 2 H), 5.14–5.07 (m, 2 H), 4.89–4.83 (m, 1 H), 4.39–4.32 (m, 1 H), 4.30–4.24 (m, 1 H), 4.20–4.07 (m, 2 H), 4.00–3.92 (m, 1 H), 3.04–2.92 (m, 1 H), 2.39–2.29 (m, 1 H), 2.16–2.04 (m, 1 H), 1.91–1.83 (m, 1 H), 1.82–1.62 (m, 7 H), 1.45–1.35 (m, 9 H), 1.27–1.07 (m, 8 H).

d) 26d (136 mg, 0.214 mmole) was dissolved in THF (4 mL) and MeOH (2 mL). An aqueous solution (2 mL) of LiOH hydrate (72 mg, 1.72 mmol) was added and the reaction mixture was stirred at RT for 20 h. The solution was concentrated and purified by preparative HPLC to give compound 306 (the less polar isomer) as a white solid (25 mg).

compound 306: MS(FAB) 607.4 (MH+)

$^1$H NMR (DMSO-$_6$) δ9.16 (d, J=6 Hz, 1 H), 8.55 (s, 1 H), 8.35 (d, J=8 Hz, 1 H), 8.12 (d, J=9 Hz, 1 H), 8.05 (dd, J=8, 7 Hz, 1 H), 7.76 (dd, J=8, 7 Hz, 1 H), 7.59 (d, J=6 Hz, 1 H), 7.02 (d, J=8 Hz, 1 H), 5.75–5.66 (m, 2 H), 5.19 (d, J=18 Hz, 1 H), 5.07 (d, J=10 Hz, 1 H), 4.55 (d, J=12 Hz, 1 H), 4.43 (dd, J=10, 8 Hz, 1 H), 4.03 (d, J=10 Hz, 1 H), 3.87–3.83 (m, 1 H), 2.66–2.59 (m, 1 H), 2.36–2.30 (m, 1 H), 1.98 (dd, J=18, 9 Hz, 1 H), 1.75–1.56 (m, 8 H), 1.38–1.35 (m, 1 H), 1.25–1.22 (m, 1 H), 1.09 (s, 9 H), 1.12–0.95 (m, 3 H).

Example 27

Synthesis of compound 307

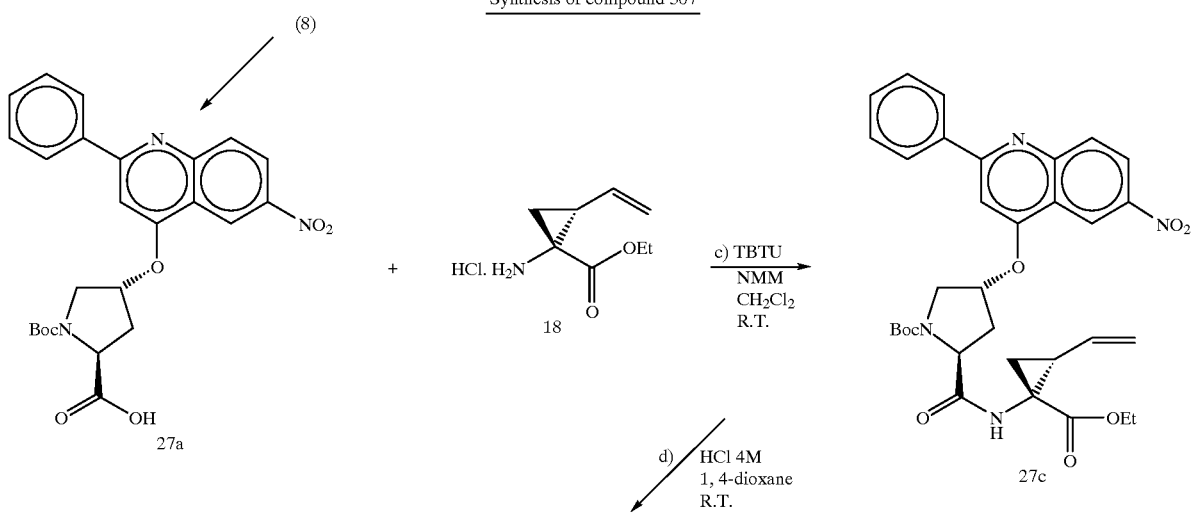

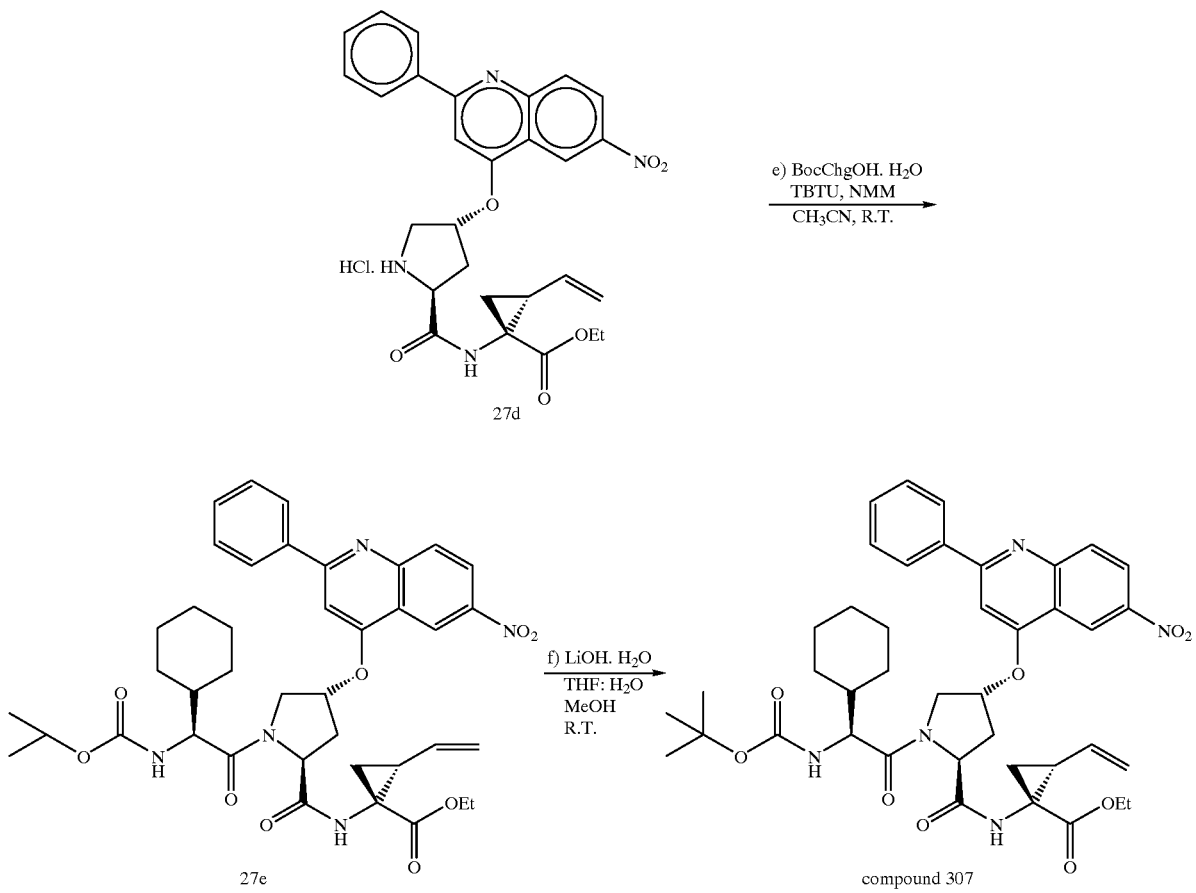

c) A solution of the acid (8) from Example 8 (505 mg, 1.05 mmol) in 5 mL of dichloromethane was treated with TBTU (378 mg, 1.17 mmol). The HCl salt of the (R,S) vinyl AccaOEt (18) (from Example 18) (279 mg, 1.46 mmol), in 7 mL of dichloromethane containing (0.60 mL, 5.46 mmol) of N-methyl morpholine, was added to the previous solution of the activated ester. The resulting solution was stirred at RT overnight. The solvent was evaporated in vacuo. The residue diluted with ethyl acetate, was washed twice with a saturated solution of sodium bicarbonate and once with brine. The organic layer was dried (MgSO$_4$) filtered and evaporated in vacuo. The residue was chromatographed over silica gel (60:40 v/v, hexanes-ethyl acetate) to afford 173 mg (27%) of the dipeptide 27c.

d, e) A solution of the dipeptide 27c (70 mg, 0.114 mmol) in 3 mL of hydrogen chloride 4.0 M solution in 1,4-dioxane was stirred at RT for 1 h (a precipitated came out from the reaction after 10 min). The solvent was removed in vacuo. The amine hydrochloride salt 27d (0.114 mmol), diluted in 1.5 mL of acetonitrile, was neutralized by addition of 65 µL (0.591 mmol) of N-methyl morpholine. A solution of the Boc ChgOH.H$_2$O (39 mg, 0.142 mmol) in 1.5 mL of acetonitrile was treated with TBTU (46 mg, 0.143 mmol) and then added to the previous solution of the amine. The resulting solution was stirred at RT (for 2 days). The solvent was removed in vacuo. The residue, diluted with ethyl acetate, was washed twice with a saturated solution of sodium bicarbonate and once with brine. The organic layer was dried (MgSO$_4$), filtered and evaporated in vacuo. 86 mg (100%) of tripeptide 27e was obtained. This crude compound was used in the next reaction without further purification.

f) To a solution of tripeptide 27e (86 mg, 0.114 mmol) in 5 mL of a mixture THF:H$_2$O (2.5:1) was added lithium hydroxide monohydrate (22 mg, 0.524 mmol). An additional 0.25 mL of MeOH was added in order to get an homogeneous solution. The resulting solution was stirred at RT overnight before the solvent was evaporated in vacuo. The residue was partitioned between water and EtOAc. The aqueous layer was acidified with 1M HCl and then extracted twice with ethyl acetate. The desired compound has been found in the ethyl acetate coming from the first basic extraction. This organic layer was dried (MgSO$_4$), filtered and evaporated in vacuo to afford 69 mg of the crude acid, which was purified by preparatory HPLC. The compound was dissolved in MeOH (4 mL) and injected onto an equilibrated Whatman Partisil 10-ODS-3 (2.2×50 cm) C18 reverse phase column. (λ=230 nm, solvent A=0.06% TFA/H$_2$O, solvent B=0.06% TFA/CH$_3$CN). Purification program: 20% to 70% of solvent B in 60 min. Fractions were analyzed by analytical HPLC. Appropriate fractions were collected and lyophilized to provide 50 mg (60%) of the desired tripeptide 307 as a white amorphous solid.

compound 307: $^1$H NMR (DMSO-d$_6$) rotamers~2:8δ8.86 (d, J=2.5 Hz, 1 H), 8.85 (s, 0.2H), 8.64 (s, 0.8H), 8.49 (dd, J=9.5, 3 Hz, 0.2H), 8.45 (dd, J=9.2 Hz, 0.8H), 8.39–8.33 (m, 2H), 8.20 (d, J=9.5 Hz, 0.2H), 8.18 (d, J=9.5 Hz, 0.8H), 7.81 (s, 0.2H), 7.78 (s, 0.8H), 7.64–7.56 (m, 3H), 6.87 (d, J=8 Hz, 0.8H), 6.36 (d, J=9 Hz, 0.2H), 5.82–5.67 (m, 2H), 5.27–5.17 (m, 1H), 5.09–5.03 (m, 1H), 4.73 (t, J=8 Hz, 0.2H), 4.55 (dd, J=10, 7.5 Hz, 0.8H), 4.49–4.40 (m, 1H), 4.00–3.95 (m, 1H), 3.83–3.76 (m, 1H), 2.87–2.80 (m, 0.2H), 2.69–2.62 (m, 0.8H), 2.39–2.26 (m, 1H), 2.08–2.00 (m, 1H), 1.75–1.41 (m, 7H), 1.37 (s, 1.8H), 1.32–1.27 (m, 1H), 1.17–0.82 (m, 5H), 0.94 (s, 7.2H).

Example 28
Synthesis of Compound 311 compound 310

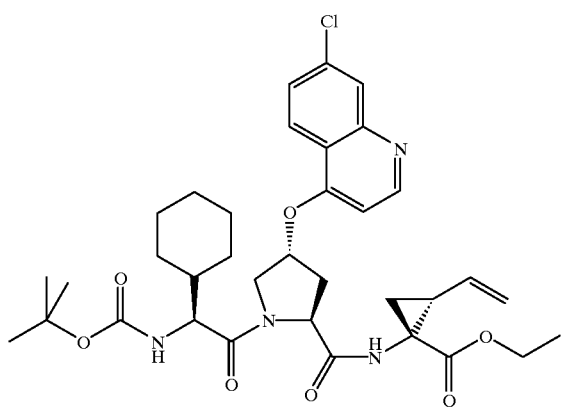

Compound 311 was prepared using the process described in Example 24 but using the appropriate building blocks.

Compound 310 $^1$H NMR (DMSO-d$_6$) δ8.98 (d, J=6 Hz, 1H), 8.52 (s, 1 H), 8.24 (d, J=9 Hz, 1 H), 8.08 (d, J=2 Hz, 1 H), 7.63 (d, J=9 Hz, 1 H), 7.37 (d, J=6 Hz, 1 H), 6.98 (d, J=8 Hz, 1 H), 5.75–5.66 (m, 1 H), 5.57 (br s, 1 H), 5.24–5.19 (m, 1 H), 5.08–5.01 (m, 1 H), 4.57–4.40 (m, 2 H), 4.00–3.96 (m, 1 H), 3.82 (dd, J=9, 8 Hz, 1 H), 2.59–2.54 (m, 1 H), 2.32–2.26 (m, 1 H), 1.99 (dd, J=17, 9 Hz, 1 H), 1.74–1.55 (m, 8 H), 1.37 (s, 1 H), 1.26–1.22(m, 1 H), 1.14–1.08 (m, 9 H), 1.02–0.91 (m, 3 H).

Example 29
Synthesis of Compound 302

302

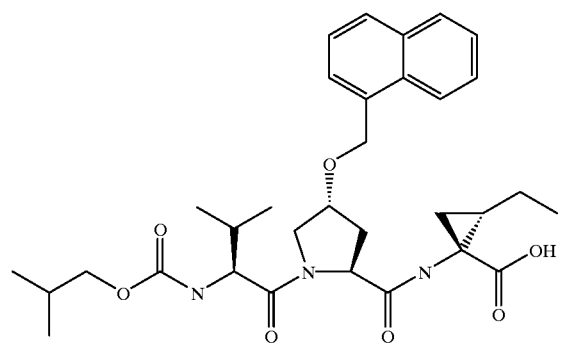

Compound 302 was prepared using the process described in Example 27 but using the appropriate building blocks.

$^1$H NMR (DMSO-d$_6$) δ8.34 (s, 1 H), 8.04–8.01 (m, 1 H), 7.94–7.92 (m, 1 H), 7.87 (d, J=8 Hz, 1 H), 7.54–7.50 (m, 3 H), 7.45 (dd, J=17,8 Hz, 1 H), 7.22 (d, J=8 Hz, 1 H), 4.94 (dd, J=55, 12 Hz, 2 H), 4.34 (s, 1 H), 4.27 (dd, J=8, 8 Hz, 1 H), 4.16 (d, J=11 Hz, 1 H), 4.07 (dd, J=8, 8 Hz, 1 H), 3.72–3.65 (m, 2 H), 3.59–3.54 (m, 1 H), 2.24–2.18 (m, 1 H), 2.02–1.95 (m, 2 H), 1.75–1.70 (m, 1 H), 1.53–1.44 (m, 2 H), 1.32–1.27 (m, 1 H), 1.21–1.17 (m, 1 H), 0.96–0.85 (m, 10 H), 0.80–0.77 (m, 5 H), 0.62–0.57 (m, 1 H).

Example 30
Synthesis of Compound 308

308

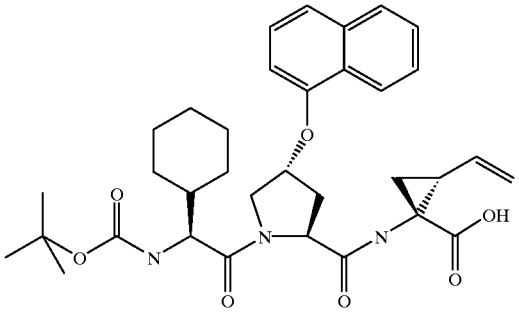

Compound 308 was prepared using the process described in Example 27 but using the appropriate building blocks.

$^1$H NMR (DMSO-d$_6$) rotamers=2:8δ8.77 (s, 0.2H), 8.45 (s, 0.8H), 8.13 (d, J=8.5 Hz, 0.8H), 8.03 (d, J=8.5 Hz, 0.2H), 7.89–7.83 (m, 1H), 7.55–7.37 (m, 4H), 7.05–6.59 (m, 1H), 6.95 (d, J=8 Hz, 0.8H), 6.26 (d, J=8.5 Hz, 0.2H), 5.81–5.64 (m, 1H), 5.33–5.28 (m, 1H), 5.26–5.15 (m, 1H), 5.08–5.02 (m, 1H), 4.60 (t, J=7.5 Hz, 0.2H), 4.38–4.27 (m, 1.8H), 4.09–3.91 (m, 1.8H), 3.74 (dd, J=12.5, 4 Hz, 0.2H), 2.69–2.60 (m, 0.2H), 2.50–2.40 (m, 1H), 2.36–2.28 (m, 0.2H), 2.23–2.14 (m, 0.8H), 2.05–1.97 (m, 0.8H), 1.76–1.44 (m, 7H), 1.37 (s, 1.8H), 1.29 (s, 7.2H), 1.28–1.20 (m, 116–0.88 (m, 5H).

Example 31
Synthesis of Compound 309

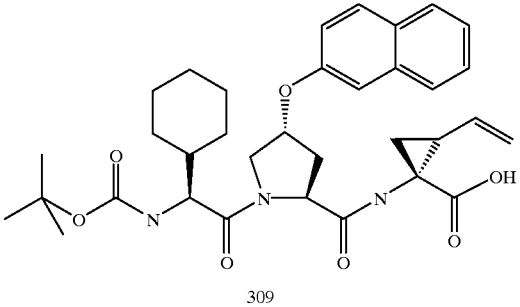

309

Compound 309 was prepared using the process described in Example 27 but using the appropriate building blocks.

$^1$H NMR (DMSO-d$_6$) rotamers=2:8δ8.75 (s, 0.2H), 8.50 (s, 0.8H), 7.89–7.78 (m, 3H), 7.50–7.44 (m, 1H), 7.17–7.09 (m, 0.8H) 7.08–7.03 (m, 0.2H), 6.79 (d, J=8.5 Hz, 0.8H), 6.33 (d, J=9 Hz, 0.2H), 5.81–5.65 (m, 1 H), 5.30–5.16 (m, 2H), 5.10–5.02 (m, 1H), 4.56 (t, J=7.5 Hz, 0.2H), 4.33 (t, J=8

Hz, 0.8H), 4.10–3.90 (m, 2.8H), 3.74–3.68 (m, 0.2H), 2.45–2.37 (m, 1H), 2.34–2.17 (m, 1H), 2.05–1.97 (m, 1H), 1.76–1.48 (m, 7H), 1.37 (s, 1.8H), 1.23 (s, 7.2H), 1.21–0.88 (m, 6H).

Example 32
Synthesis of Compound 305

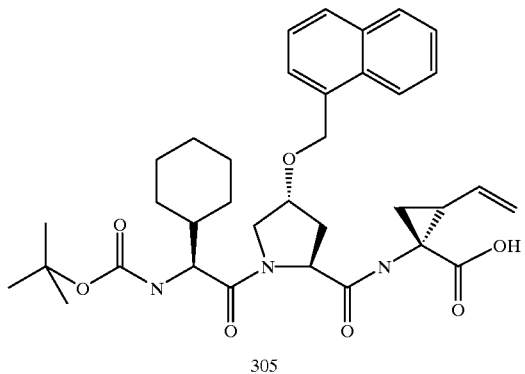

Compound 305 was prepared using the process described in Example 27 but using the appropriate building blocks.

$^1$H NMR (DMSO-$d_6$) rotamers (1:9) δ8.68 (s, 0.1H), 8.43 (s, 0.9H), 8.04–8:00 (m, 1H), 7.95–7.91 (m, 1H), 7.87 (d, J=8.5 Hz, 1H), 7.57–7.49 (m, 3H), 7.47–7.42 (m, 1H), 6.82 (d, J=8.05 Hz, 0.9H), 6.21 (d, J=8.5 Hz, 0.1H), 5.80–5.64 (m, 1H), 5.21 (dd, J–17, 2 Hz, 0.1H), 5.18 (dd, J=17, 2 Hz, 0.9H), 5.06 (dd, J=10.5, 2 Hz, 1H), 5.02–4.85 (m, 2H), 4.43 (t, J=7.5 Hz, 0.1H), 4.34 (br s, 1H), 4.23 (t, J=8.5 Hz, 0.9H), 4.16–4.05 (m, 1.8H), 3.89–3.82 (m, 0.2H), 3.74 (dd, J=11, 3.5 Hz, 0.9H), 3.53 (dd, J=12.5, 4 Hz, 0.1H), 2.30–2.21 (m, 1H), 2.02–1.94 (m, 2H), 1.74–1.38 (m, 7H), 1.36 (s, 0.9H), 1.28 (s, 8.1H), 1.25–0.87 (m, 6H).

Example 33

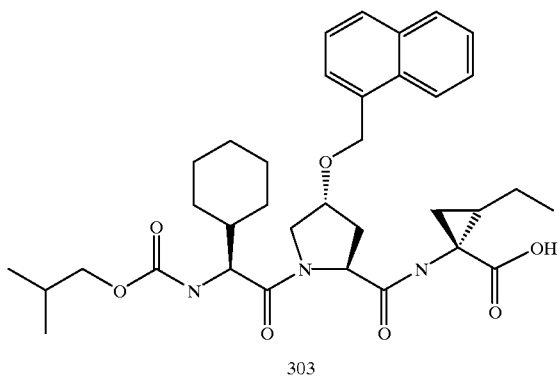

Compound 303 was prepared using the process described in Example 27 but using the appropriate building blocks.

$^1$H NMR (DMSO-$d_6$) δ8.29 (s, 1 H), 8.04–8.01 (m, 1 H), 7.94–7.92 (m, 1 H), 7.87 (d, J=8 Hz, 1 H), 7.56–7.52 (m, 3 H), 7.46 (dd, J=8,7 Hz, 1 H), 7.19 (d, J=9 Hz, 1 H), 5.01 (d, J=12 Hz, 1 H), 4.86 (d, J=12 Hz, 1 H), 4.34 (br. s, 1 H) 4.24 (t, J=8 Hz, 1 H), 4.18–4.09 (m, 2 H), 3.74–3.53 (m, 3 H), 2.24–2.18 (m, 1 H), 2.04–1.95 (m, 1 H), 1.74–1.45 (m, 10 H), 1.31–1.13 (m, 4 H), 0.96–0.86 (m, 7 H), 0.79–0.76 (m, 5 H).

Example 34

Synthesis of Compound 403

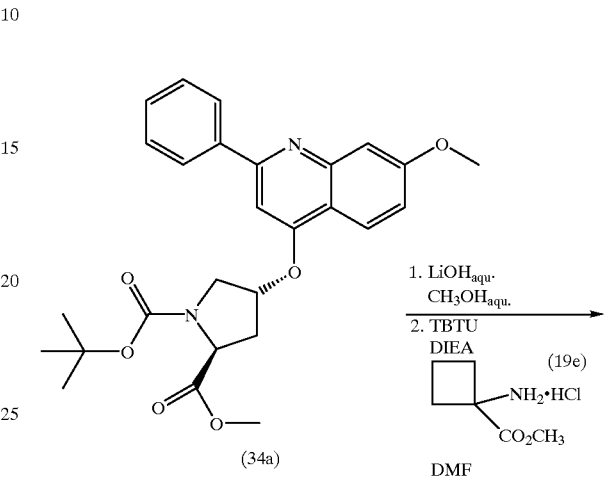

a) Coupling of P2 with P1

The methyl ester derivative of 7 (34a) (170 mg, 0.355 mmole) was stirred in 50% THF-methanol (4 ml) and aqueous LiOH (1M, 1 ml) at RT for 1 h. The solution was concentrated (Rotavap, 30° C.) and residue acidified to pH 6 and solution lyophilized. The resulting powder was stirred in dry DMF (3 ml) in the presence of DIEA (0.4 ml) followed by the successive addition of 1,1-aminocyclobutylcarboxylic acid methyl ester hydrochloride (34b) (140 mg, 0.845 mmole) and TBTU (134 mg, 0.417 mmole). After stirring for 18 h at RT, the mixture was purified by flash chromatography on silica gel (230–400 Mesh) using 1:2 ethyl acetate-hexane to afford an orange oil (98 mg, 90% purity by HPLC).

b) Coupling of P1-P2 with P3

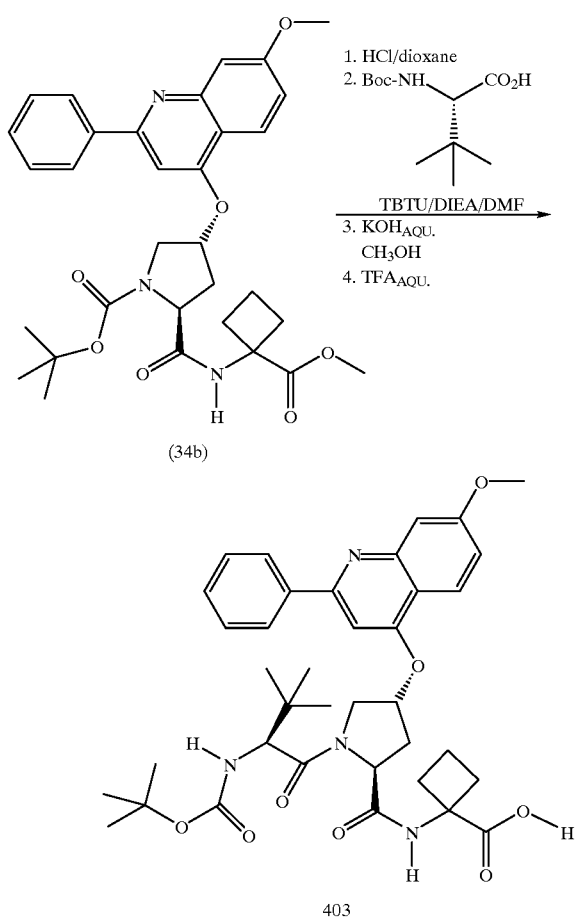

The dipeptide 34b (97 mg, 90%, 0.155 mmole) was stirred in 4N HCl-dioxane (5 ml) during 1 h at RT . The solution was then concentrated to dryness (Rotavap, high vacuum) to afford a beige solid. This material was stirred in dry DMF (2 ml) at RT in the presence of DIEA (0.4 ml) followed by addition of L-Boc-Tbg (80 mg, 0.35 mmole) and TBTU (112 mg, 0.35 mmole). After stirring 2 days at RT, the solution was poured in ethyl acetate to generate the free base using 5% aqueous potassium carbonate. The organic phase was worked up to give a yellow oily residue. The material was purified by flash chromatography on silica gel column (230–400 Mesh) using 1:2 & 3:1 v/v ethyl acetate:hexane to afford 40 mg of an oil, homogeneous by HPLC.

The methyl ester (40 mg) was finally saponified in 1N potassium hydroxide (2 ml) in methanol (4 ml) by stirring at RT during 3 h. The mixture was concentrated (Rotavap, 30° C.) and acidified to pH 4 with 2N hydrochloric acid. This mixture was purified by preparative HPLC on C18 column using a gradient of 0–50% aqueous acetonitrile (0.1% TFA) at 220 nm The fractions were pooled, concentrated to half volume and lyophilized to afford 403 as a white fluffy solid (10 mg).

$^1$H NMR (400 MHz, DMSO-$d_6$) δ Mixture of rotamers: NH+ (1H, s, 8.6 ppm), CH (3H, m, 8.2 ppm), Ph (5H, broad s, 7.66 & 7.53 ppm), CH (1H, broad, 7.22 ppm), NH (1H, d, J=7.6 Hz, 6.71 ppm), CHO (1H, broad s, 5.76 ppm), CH (2H, m, 4.58–4.49 ppm), CH (1H, m, 4.04 ppm), CH$_3$O (3H, s, 3.97 ppm), CH (1H, d, 3.86 ppm), CH (7H, very broad, 1.8–2.6 ppm), Boc group (9H, s, 1.25 ppm) and t-butyl group (9H, s, 0.97 ppm).

MS. showed M+H+at m/e 675 (100%).
HPLC peak 98% at 18.9 min.

Example 35

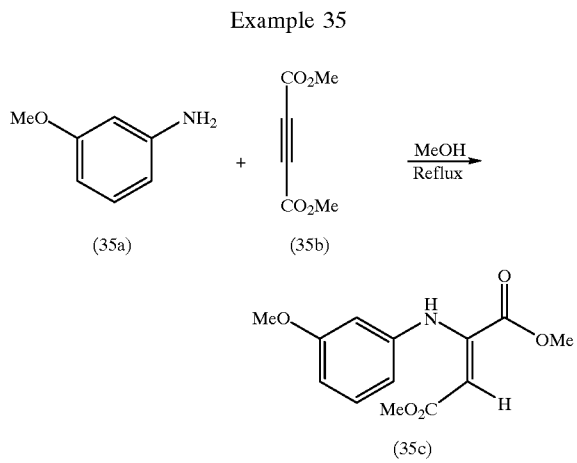

A solution of m-anisidine (35a) (9.15 mL, 81.4 mmoles) and dimethylacetylene-dicarboxylate (35b) (10.0 mL, 81.3 mmoles) in 160 mL of methanol is heated under reflux for 2 h. The solvent is removed in vacuo and the residue purified by a flash column chromatography. (90:10 hexanes-ethyl acetate). Compound 35c (17.0 g, 79% yield) is obtained as an orange oil.

$^1$H NMR (CDCl$_3$) δ9.62 (broad s, 1H), 7.17 (dd, J=7 and 8.5 Hz, 1H), 6.66–6.62 (m, 1H), 6.49–6.45 (m, 2H), 5.38 (s, 1H), 3.77 (s, 3H), 3.74 (s, 3H), 3.71 (s, 3H).

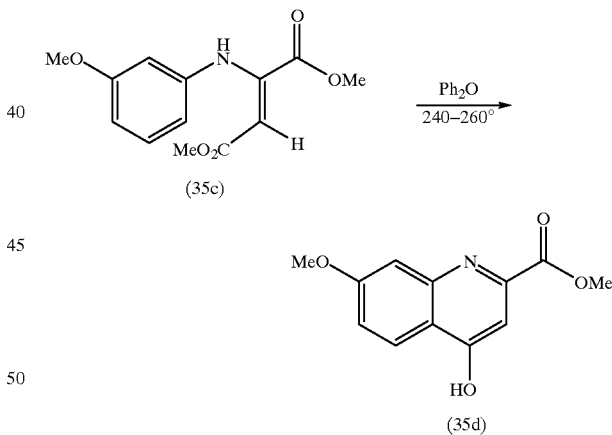

Diphenylether (50 mL) is heated in a sand bath up to an internal temperature of ≈250°. Diester adduct (35c) (7.5 g, 28.3 mmoles), dissolved in 5 mL of diphenyl ether, is added within 2 min to the boiling solvent. The heating is maintained for 5 min and the reaction mixture is then allowed to cool down to room temperature. Rapidly a beige solid precipitated out. The solid is filtered and then triturated with methanol. To yield 4.1 g (62% yield) of the desired compound 35d.

$^1$H NMR (DMSO-$d_6$) δ7.97 (d, J=9 Hz, 1H), 7.40 (d, J=2 Hz, 1H), 6.96 (dd, J=9 and 2 Hz, 1H), 6.55 (s, 1H), 3.95 (s, 3H), 3.84 (s, 3H).

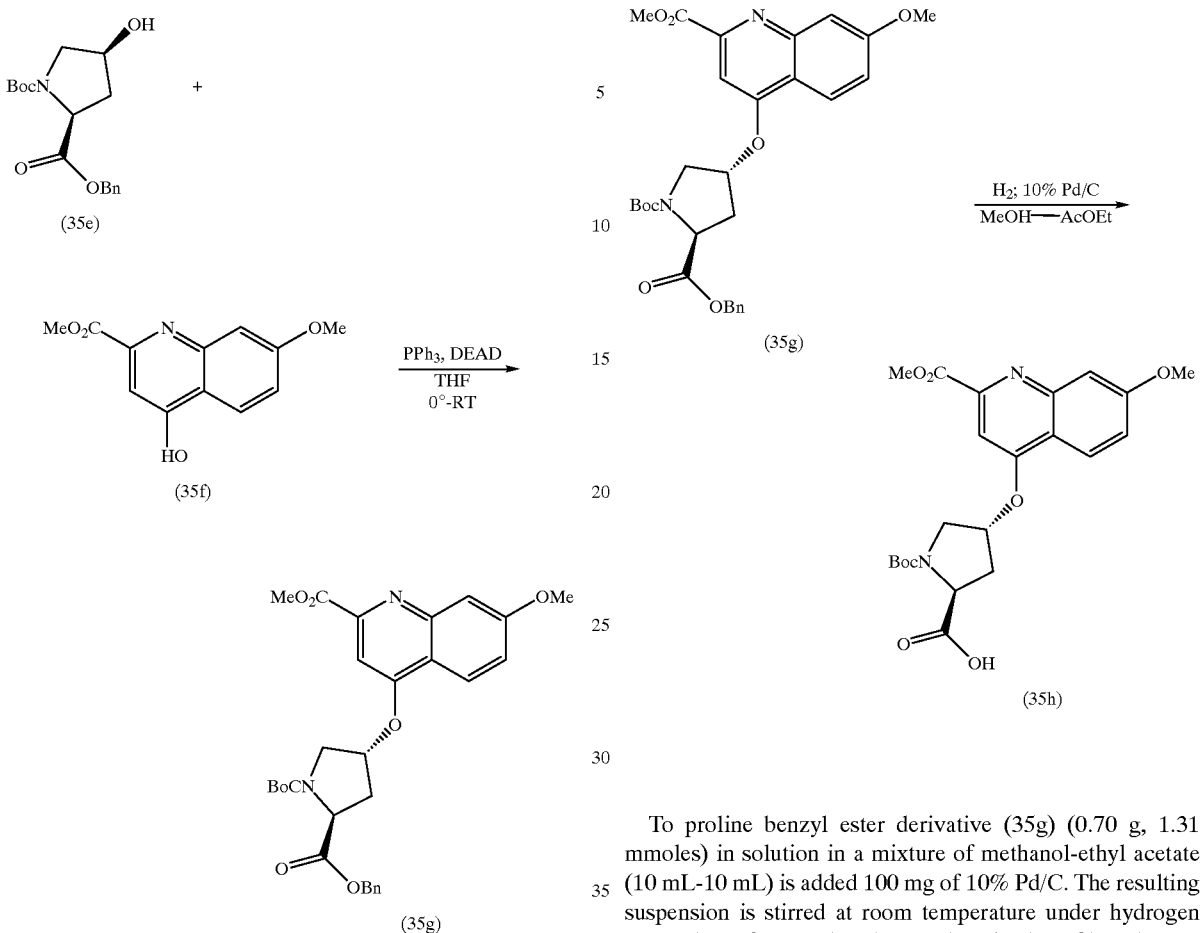

A solution of cis-4-hydroxy-L-proline derivative (35e) (1.71 g, 5.33 mmoles), 4-hydroxyquinoline derivative (35f) (1.25 g, 5.36 mmoles) and triphenylphosphine (2.80 g, 10.68 mmoles) in 75 mL of THF is cooled down to 0° for the addition drop to drop (≈1 h) of DEAD (1.70 mL, 10.80 mmoles). The reaction mixture was then allowed to warm up slowly to room temperature and the stirring was continued overnight. The solvent is removed in vacuo and the residue purified by a flash column chromatography (70:30 ehtylacetate-hexanes). Compound 35g (0.7 g of pure compound 35g, and 1.8 g of compound 35g contaminated with ≈50% of triphenylphosphate oxide) is obtained as a white solid.

$^1$H NMR (CDCl$_3$) rotamers (4:6) δ8.04 (d, J=9 Hz, 1H), 7.54 (d, J=2.5 Hz, 1H), 7.40–7.32 (m, 6H), 7.23 (dd, J=9 and 2.5 Hz, 1H), 5.33–5.13 (m, 3H), 4.66 (t, J=7.5 Hz, 0.4 H), 4.54 (t, J=8 Hz, 0.6 H), 4.07 (s, 3H), 3.94 (s, 3H), 4.04–3.80 (m, 2H), 2.78–2.65 (m, 1H), 2.47–2.34 (m, 1H), 1.45 (s, 3.6H), 1.37 (s, 5.4H).

To proline benzyl ester derivative (35g) (0.70 g, 1.31 mmoles) in solution in a mixture of methanol-ethyl acetate (10 mL-10 mL) is added 100 mg of 10% Pd/C. The resulting suspension is stirred at room temperature under hydrogen atmosphere for 1½ h. The catalyst is then filtered on a Millex-HV Millipore (0.45 μm filter unit) and the solvents are evaporated in vacuo. Quantitative yield of the desired acid 35h (0.59 g) is obtained.

$^1$H NMR: (CDCl$_3$) rotamers 70:30δ8.06 (d, J=9.5 Hz, 0.3 H), 8.01 (d, J=9 Hz, 0.7 H), 7.56 (d, J=2 Hz, 1H), 7.44 (broad s, 0.7 H), 7.41 (broad s, 0.3 H), 7.24 (dd, J=9 and 2.5 Hz, 1H), 5.31–5.25 (m, 1H), 4.67 (t, J=7.5 Hz, 0.7 H), 4.55 (t, J=7.5 Hz, 0.3 H), 4.08 (s, 3H), 3.95 (s, 3H), 4.04–3.80 (m, 2H), 2.83–2.72 (m, 1H), 2.71–2.47 (m, 1H), 1.46 (s, 9H).

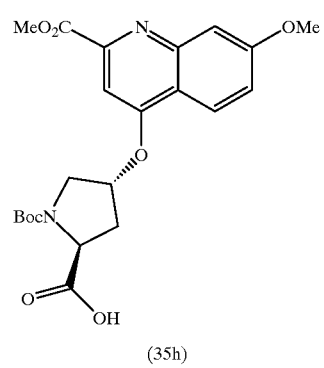

(35h)

2.20–2.08 (m, 1H), 1.97–1.84 (m, 1H), 1.58–1.52 (m, 1H), 1.44 (s, 9H).

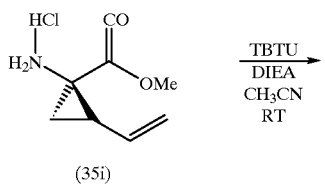

(35i)

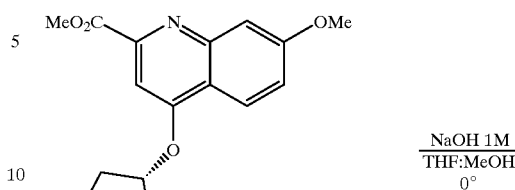

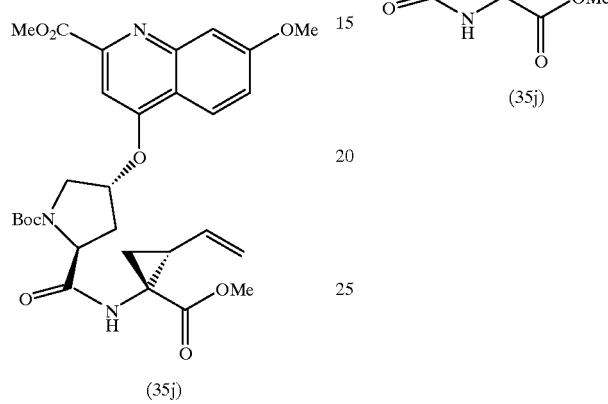

(35j)

The salt of the amine 35i (215 mg, 1.21 mmoles) in 7 mL of acetonitrile is treated with 0.95 mL of DIEA (5.45 mmoles). This solution is then added to a solution of acid 35h (590 mg, 1.32 mmoles) and TBTU (389 mg, 1.21 mmoles) in 5 mL of CH₃CN the resulting solution is stirred at room temperature overnight. The solvent is removed in vacuo and the residue is diluted with ethylacetate and washed twice with a saturated solution of sodium bicarbonate once with brine and dried over MgSO₄. The solvent is removed in vacuo and the residue is purified by flash column chromatography (75:25 AcOEt-hexanes) to afford 527 mg (70% yield) of the desired dipeptide (35j).

¹H NMR: (CDCl₃) δ8.01 (d, J=9 Hz, 1H), 7.55 (d, J=2.5 Hz, 1H), 7.45 (s, 1H), 7.22 (dd, J=9 and 2.5 Hz, 1H), 5.81–5.71 (m, 1H), 5.36–5.28 (m, 2H), 5.18–5.12 (m, 1H), 4.61–4.45 (m, 1H), 4.07 (s, 3H), 3.94 (s, 3H), 3.91–3.74 (m, 2H), 3.72 (s, 3H), 2.99–2.84 (m, 1H), 2.49–2.34 (m, 1H),

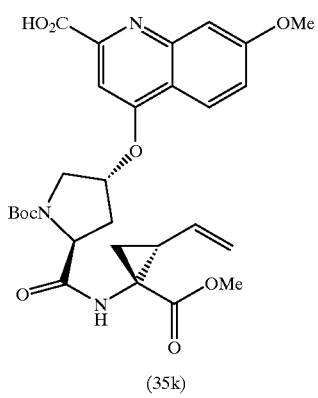

(35k)

The diester 35j (716 mg, 1.25 mmoles) in solution in a mixture of THF:MeOH (1.5 mL-1.5 mL) is cooled to 0° before being treated with an aqueous solution of NaOH 1M (1.25 mL, 1.25 mmoles). After 1 h of stirring at 0°, 3 drops of glacial acetic acid are added to neutralize the NaOH. The solvents are removed in vacuo and the compound is dried on the pump for a few hours.

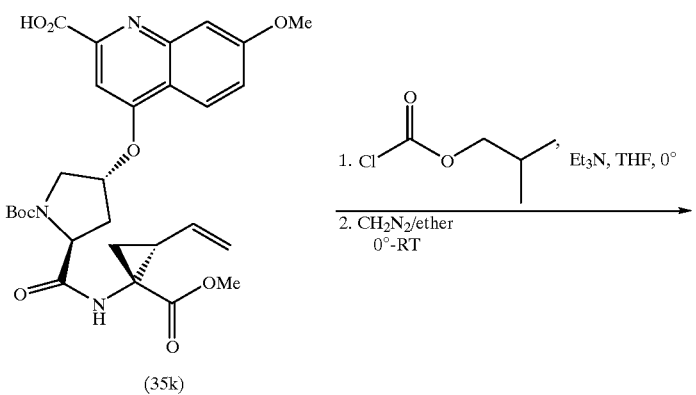

(35k)

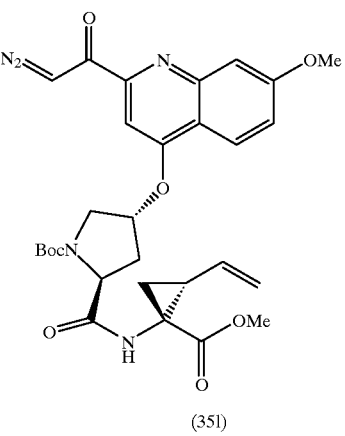

(35l)

A solution of the acid 35k sodium salt (1.25 mmoles) and Et₃N (0.19 mL, 1.36 mmoles) in 8 mL of THF is cooled to 0° and isobutyl chloroformate (0.18 mL, 1.39 mmoles) is added. After 40 min diazomethane (9 mL, 6.30 mmoles) is added and the resulting solution is stirred at 0° for 30 min and at room temperature for 2 h. The solvents are removed in vacuo. The residue, diluted with ethyl acetate, is washed twice with a saturated solution of NaHCO₃ once with brine and dried over MgSO₄, the solvent is evaporated under vacuo and the residue is purified by flash column chromatography (50:50 Hexanes/AcOEt) to afford 378 mg (52% yield) of the expected diazoketone 35l.

¹H NMR: (CDCl₃) δ8.00 (d, J=9 Hz, 1H), 7.42 (s, 1H), 7.35 (d, J=2.5 Hz, 1H), 7.20 (dd, J=9 and 2.5 Hz, 1H), 6.92 (s, 1H), 5.81–5.71 (m, 1H), 5.35–5.28 (m, 3H), 5.17–5.13 (m, 1H), 4.61–4.40 (m, 1H), 3.97 (s, 3H), 3.96–3.74 (m, 2H), 3.72 (s, 3H), 2.94–2.38 (m, 2H), 2.18–2.06 (m, 1H), 1.98–1.84 (m, 1H), 1.57–1.52 (m, 1H), 1.42 (s, 9H).

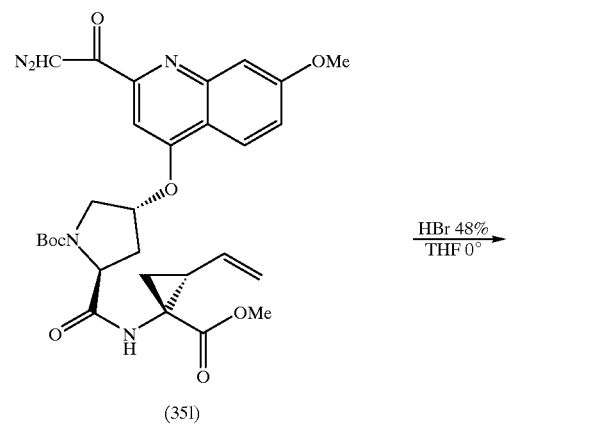

To a cooled (0°) solution of the diazoketone 35l (0.37 g, 0.642 mmoles) in 15 mL of THF is added 0.25 mL of HBr 48%. The resulting yellow solution is stirred at 0° for 1 h. The reaction mixture is partitioned between ethyl acetate and a saturated solution of NaHCO₃. The organic phase is washed one more time with NaHCO₃ and dried with NaSO₄. After evaporation of the solvents in vacuo, 0.36 g (90% yield) of the α-bromoketone 35m is isolated.

The α-bromoketone 35m (170 mg, 0.271 mmoles) in 10 mL of isopropanol is treated with 1-acetyl-2-thiourea (64 mg, 0.542 mmoles). The resulting solution is heated at 75° for 1 h. The solvent is removed in vacuo. The residue is diluted with ethyl acetate and washed twice with a saturated solution of NaHCO₃, once with brine and dried with MgSO₄. Evaporation of the solvent in vacuo afforded 182 mg (>100%) of crude material 35n.

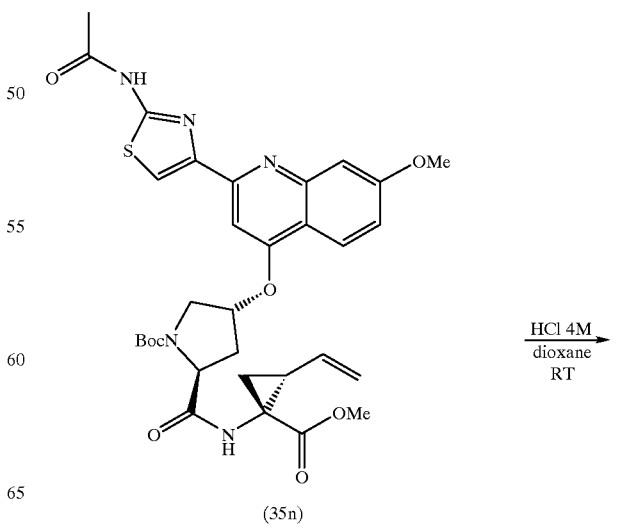

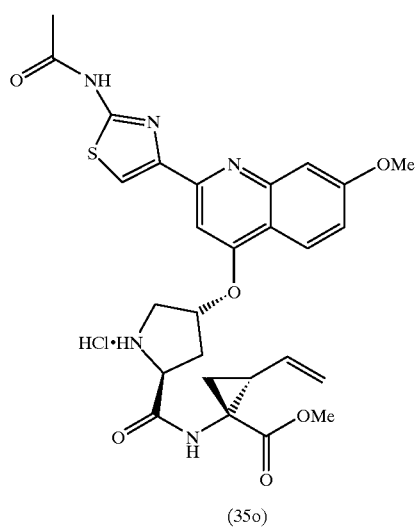

(35o)

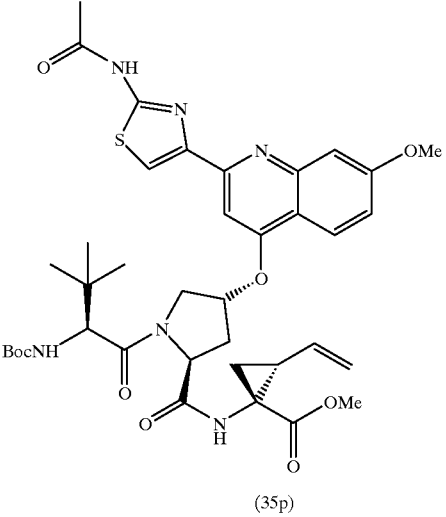

(35p)

The dipeptide 35n (145 mg, 0.223 mmoles) is treated with 3 mL of a 4M solution of HCl in dioxane. The resulting solution is stirred at room temperature for 1 h. The solvents are removed in vacuo and the residue is dried over the pump. The salt of the amine 35o in 5 mL of CH$_3$CN is treated with 195 µL (1,12 mmoles) of DIEA. This solution is then added to the solution of the Boc-tert-butylglycine (103 mg, 0.446 mmoles) and HATU (186 mg, 0.489 mmoles) in 3 mL of CH$_3$CN. The reaction mixture is stirred at room temperature overnight. The CH$_3$CN is evaporated in vacuo. The residue diluted with ethyl acetate is washed twice with a saturated solution of NaHCO$_3$, once with brine and dried with MgSO$_4$. After removal of the solvent, 274 mg of the crude tripeptide 35p is obtained (>100%).

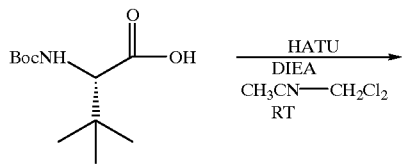

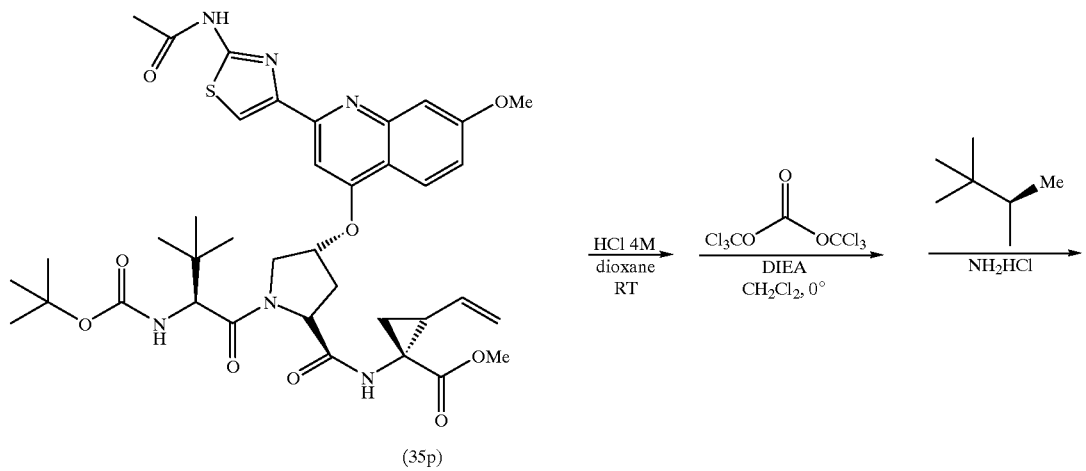

(35p)

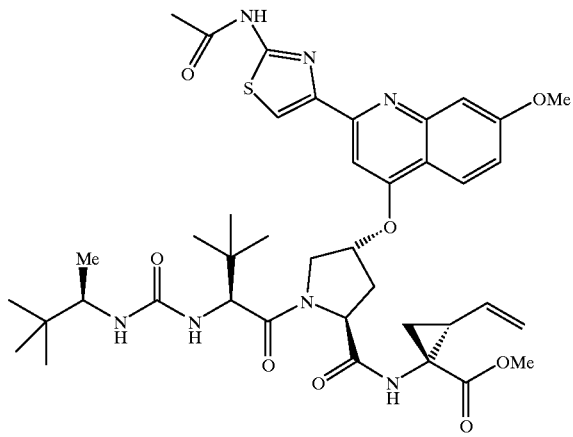

(35q)

The tripeptide 35p (56 mg, 0.0733 mmoles), in 4 mL of a 4M solution of HCl in dioxane, is stirred at room temperature for 2 h. The solvent is removed in vacuo and the residue dried over the pump.

The salt of the amine obtained is dissolved in 4 mL of $CH_2Cl_2$ and treated with 0.13 mL of DIEA (0.746 mmoles) followed by 26 mg of triphosgene (0.0876 mmoles). After 3 h incubation, 1,2,2-trimethylpropylamine (20 mg, 0.146 mmoles) is added (synthesized as described in Moss N., Gauthier J., Ferland J. M., February 1995, SynLett. (2), 142–144). The ice bath is removed and the reaction mixture is stirred at room temperature overnight. The $CH_2Cl_2$ is evaporated in vacuo. The residue, diluted with ethyl acetate is washed twice with a saturated solution of $NaHCO_3$, once with brine and dried with $MgSO_4$ to afford 60 mg (≈100%) of the desired urea 35q.

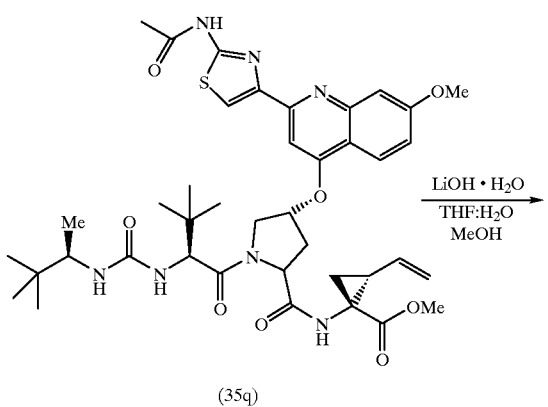

(35q)

-continued

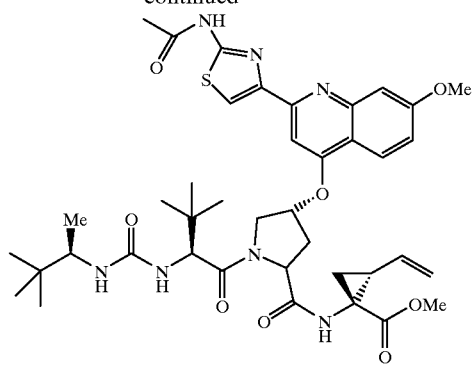

compound 333

A solution of methyl ester 35q (57 mg, 0.0721 mmoles) in a mixture of $THF:H_2O$ (2.5 mL:1mL) is treated with solid $LiOH \cdot H_2O$ (25 mg, 0.595 mmoles) and 1 mL of MeOH is added in order to clarify the solution. After stirring for 4 h at room temperature, the reaction is neutralized by addition of a 1M solution of HCl. The solvents are removed in vacuo and the residue is purified by a preparative chromatography. The compound dissolved in 2.5 mL of MeOH, is injected into an equilibrated Whatman Partisil 10-ODS-3 (2.2×50 cm) $C_{18}$ is reverse phase column. Purification program: Linear Gradient at 20 mL/nm, λ220 nm, inject at 10% A up to 60% A in 60 min. A:0.06% $TFA/CH_3CN$; B:0.06%; $TFA/H_2O$. Fractions were analyzed by analytical HPLC. The product collected was lyophilized to provide 15 mg of compound 333 as an off white solid (27% yield).

$^1$H NMR: (DMSO-$d_6$) δ8.88 (s, 0.2H), 8.84 (d, J=4.5 Hz, 0.2H), 8.68 (d, J=8.5 Hz, 0. H), 8.56 (s, 0.8H), 8.40–8.13 (m, 1,5H), 7.96 (d, J=9.0 Hz, 0.2H), 7.72–7.44 (m, 2.4H), 7.35–7.09 (m, 1.2H), 6.98 (d, J=9 Hz, 0.2H), 6.15 (d, J=9 Hz, 0.2H), 6.06 (d, J=9 Hz, 0.8H), 5.93 (d, J=9.5 Hz, 0.24H), 5.86 (d, J=9 Hz, 0.8H), 5.79–5.67 (m, 1H), 5.69–5.44 (m, 1H), 5.24–5.14 (m, 1H), 5.09–5.01 (m, 1H), 4.50–4.35 (m, 2H), 4.24 (d, J=9.0 Hz, 0.2H), 4.20 (d, J=9.0 Hz, 0.8H), 4.06–3.98 (m, 2H), 3.95 (s, 3H), 3.77–3.60 (m, 2H), 2.58–2.50 (m, 1H), 2.33–2.28 (m, 1H), 2.22 (s, 2.4H), 2.21 (s, 0.6H), 2.02 (q, J–9 Hz, 1H), 1.56–1.38 (m, 1H), 1.28–1.22 (m, 1H), 0.97 (s, 9H), 0.83 (d, J=6 Hz, 3H), 0.72 (s, 9H).

MS(FAB) 778.3 (m+H)$^+$, 776.3 (M−H)$^-$.

Example 36

Cloning, Expression and Purification of the Recombinant HCV NS3 Protease Type 1b Serum from an HCV-infected patient was obtained through an external collaboration (Bernard Willems MD, Hôpital St-Luc, Montréal, Canada and Dr. Donald Murphy, Laboratoire de Santé Publique du Québec, Ste-Anne de Bellevue, Canada). An engineered full-length cDNA template of the HCV genome was constructed from DNA fragments obtained by reverse transcription-PCR (RT-PCR) of serum RNA and using specific primers selected on the basis of homology between other genotype 1b strains. From the determination of the entire genomic sequence, a genotype 1b was assigned to the HCV isolate according to the classification of Simmonds et al. (J. Clin. Microbiol., (1993), 31, p.1493–1503). The amino acid sequence of the non-structural region, NS2-NS4B, was shown to be greater than 93% identical to HCV genotype 1b (BK, JK and 483 isolates) and 88% identical to HCV genotype 1a (HCV-1 isolate). A DNA fragment encoding the polyprotein precursor (NS3/NS4A/NS4B/NS5A/NS5B) was generated by PCR and introduced into eukaryotic expression vectors. After transient transfection, the polyprotein processing mediated by the HCV NS3 protease was demonstrated by the presence of the mature NS3 protein using Western blot analysis. The mature NS3 protein was not observed with expression of a polyprotein precursor containing the mutation S1165A, which inactivates the NS3 protease, confirming the functionality of the HCV NS3 protease.

The DNA fragment encoding the recombinant HCV NS3 protease (amino acid 1027 to 1206) was cloned in the pET11d bacterial expression vector. The NS3 protease expression in E. coli BL21(DE3)pLysS was induced by incubation with 1 mM IPTG for 3 h at 22° C. A typical fermentation (18 L) yielded approximately 100 g of wet cell paste. The cells were resuspended in lysis buffer (3.0 mL/g) consisting of 25 mM sodium phosphate, pH 7.5, 10% glycerol (v/v), 1 mM EDTA, 0.01% NP-40 and stored at −80° C. Cells were thawed and homogenized following the addition of 5 mM DTT. Magnesium chloride and DNase were then added to the homogenate at final concentrations of 20 mM and 20 μg/mL respectively. After a 25 min incubation at 4° C., the homogenate was sonicated and centrifuged at 15000×g for 30 min at 4° C. The pH of the supernatant was then adjusted to 6.5 using a 1M sodium phosphate solution.

An additional gel filtration chromatography step was added to the 2 step purification procedure described in WO 95/22985 (incorporated herein by reference). Briefly, the supernatant from the bacterial extract was loaded on a SP HiTrap column (Pharmacia) previously equilibrated at a flow rate of 2 mL/min in buffer A (50 mM sodium phosphate, pH 6.5, 10% glycerol, 1 mM EDTA, 5 mM DTT, 0.01% NP-40). The column was then washed with buffer A containing 0.15 M NaCl and the protease eluted by applying 10 column volumes of a linear 0.15 to 0.3 M NaCl gradient. NS3 protease-containing fractions were pooled and diluted to a final NaCl concentration of 0.1 M. The enzyme was further purified on a HiTrap Heparin column (Pharmacia) equilibrated in buffer B (25 mM sodium phosphate, pH 7.5, 10% glycerol, 5 mM DTT, 0.01% NP-40). The sample was loaded at a flow rate of 3 mL/min. The column was then washed with buffer B containing 0.15 M NaCl at a flow rate of 1.5 mL/min. Two step washes were performed in the presence of buffer B containing 0.3 or 1M NaCl. The protease was recovered in the 0.3M NaCl wash, diluted 3-fold with buffer B, reapplied on the HiTrap Heparin column and eluted with buffer B containing 0.4 M NaCl. Finally, the NS3 protease-containing fractions were applied on a Superdex 75 HiLoad 16/60 column (Pharmacia) equilibrated in buffer B containing 0.3 M NaCl. The purity of the HCV NS3 protease obtained from the pooled fractions was judged to be greater than 95% by SDS-PAGE followed by densitometry analysis.

The enzyme was stored at −80° C. and was thawed on ice and diluted just prior to use.

Example 37

Recombinant HCV NS3 Protease/NS4A Cofactor Peptide Radiometric Assay

The enzyme was cloned, expressed and prepared according to the protocol described in Example 36. The enzyme was stored at −80° C., thawed on ice and diluted just prior to use in the assay buffer containing the NS4A cofactor peptide. The substrate used for the NS3 protease/NS4A cofactor peptide radiometric assay, DDIVPC-SMSYTW, is cleaved between the cysteine and the serine residues by the enzyme. The sequence DDIVPC-SMSYTW corresponds to the NS5A/NS5B natural cleavage site in which the cysteine residue in P2 has been substituted for a proline. The peptide substrate DDIVPC-SMSYTW and the tracer biotin-DDIVPC-SMS[$^{125}$I-Y]TW are incubated with the recombinant NS3 protease and the NS4A peptide cofactor KKGS-VVIVGRIILSGRK (molar ratio enzyme: cofactor 1:100) in the absence or presence of inhibitors. The separation of substrate from products is performed by adding avidin-coated agarose beads to the assay mixture followed by filtration. The amount of SMS[$^{125}$I-Y]TW product found in the filtrate allows for the calculation of the percentage of substrate conversion and of the percentage of inhibition.

A. Reagents

Tris and Tris-HCl (UltraPure) were obtained from Gibco-BRL. Glycerol (UltraPure), MES and BSA were purchased from Sigma. TCEP was obtained from Pierce, DMSO from Aldrich and NaOH from Anachemia.

Assay buffer: 50 mM Tris HCl, pH 7.5, 30% (w/v) glycerol, 1 mg/mL BSA, 1 mM TCEP (TCEP added just prior to use from a 1 M stock solution in water).

Substrate: DDIVPCSMSYTW, 25 μM final concentration (from a 2 mM stock solution in DMSO stored at −20° C. to avoid oxidation).

Tracer: reduced mono iodinated substrate biotin DDIVPC SMS[$^{125}$I Y]TW (~1 nM final concentration).

HCV NS3 protease type 1b, 25 nM final concentration (from a stock solution in 50 mM sodium phosphate, pH 7.5, 10% glycerol, 300 mM NaCl, 5 mM DTT, 0.01% NP-40).

NS4A Cofactor peptide: KKGSVVIVGRIILSGRK, 2.5 μM final concentration (from a 2 mM stock solution in DMSO stored at −20° C.).

B. Protocol

The assay was performed in a 96-well polystyrene plate from Costar. Each well contained:

20 μL substrate/tracer in assay buffer;

10 μL±inhibitor in 20% DMSO/assay buffer;

10 μL NS3 protease 1b/NS4 cofactor peptide (molar ratio 1:100).

Blank (no inhibitor and no enzyme) and control (no inhibitor) were also prepared on the same assay plate.

The enzymatic reaction was initiated by the addition of the enzyme/NS4A peptide solution and the assay mixture was incubated for 40 min at 23° C. under gentle agitation. Ten (10) μL of 0.5N NaOH were added and 10 μL 1 M MES, pH 5.8 were added to quench the enzymatic reaction.

Twenty (20) μL of avidin-coated agarose beads (purchased from Pierce) were added in a Millipore MADP N65 filtration plate. The quenched assay mixture was transferred to the filtration plate, and incubated for 60 min at 23° C. under gentle agitation.

The plates were filtered using a Millipore MultiScreen Vacuum Manifold Filtration apparatus, and 40 μL of the filtrate was transferred in an opaque 96-well plate containing 60 μL of scintillation fluid per well.

The filtrates were counted on a Packard TopCount instrument using a $^{125}$I-liquid protocol for 1 minute.

The % inhibition was calculated with the following equation:

$$100-[(\text{count}_{inh}-\text{counts}_{blank})/(\text{counts}_{ctr}-\text{counts}_{blank})\times 100]$$

A non-linear curve fit with the Hill model was applied to the inhibition-concentration data, and the 50% effective concentration ($IC_{50}$) was calculated by the use of SAS software (Statistical Software System; SAS Institute, Inc. Cary, N.C.).

Example 38
Full-length NS3-NS4A Heterodimer Protein Assay

The NS2-NS5B-3' non coding region was cloned by RT-PCR into the pCR®3 vector (Invitrogen) using RNA extracted from the serum of an HCV genotype 1b infected individual (provided by Dr. Bernard Willems, Hôpital St-Luc, Montréal, Québec, Canada). The NS3-NS4A DNA region was then subcloned by PCR into the pFastBac™ HTa baculovirus expression vector (Gibco/BRL). The vector sequence includes a region encoding a 28-residue N-terminal sequence which contains a hexahistidine tag. The Bac-to-Bac™ baculovirus expression system (Gibco/BRL) was used to produce the recombinant baculovirus. The full length mature NS3 and NS4A heterodimer protein (His-NS3-NS4AFL) was expressed by infecting $10^6$ Sf21 cells/mL with the recombinant baculovirus at a multiplicity of infection of 0.1–0.2 at 27° C. The infected culture was harvested 48 to 64 h later by centrifugation at 4° C. The cell pellet was homogenized in 50 mM $NaPO_4$, pH 7.5, 40% glycerol (w/v), 2 mM β-mercaptoethanol, in presence of a cocktail of protease inhibitors. His-NS3-NS4AFL was then extracted from the cell lysate with 1.5% NP-40, 0.5% Triton X-100, 0.5M NaCl, and a DNase treatment. After ultracentrifugation, the soluble extract was diluted 4-fold and bound on a Pharmacia Hi-Trap Ni-chelating column. The His-NS3-NS4AFL was eluted in a >90% pure form (as judged by SDS-PAGE), using a 50 to 400 mM imidazole gradient. The His-NS3-NS4AFL was stored at −80° C. in 50 mM sodium phosphate, pH 7.5, 10% (w/v) glycerol, 0.5 M NaCl, 0.25 M imidazole, 0.1% NP-40. It was thawed on ice and diluted just prior to use. The protease activity of His-NS3-NS4AFL was assayed in 50 mM Tris-HCl, pH 8.0, 0.25 M sodium citrate, 0.01% (w/v) n-dodecyl-β-D-maltoside, 1 mM TCEP. Five (5) μM of the internally quenched substrate anthranilyl-DDIVPAbu[C(O)-O]-AMY(3-$NO_2$)TW-OH in presence of various concentrations of inhibitor were incubated with 1.5 nM of His-NS3-NS4AFL for 45 min at 23° C. The final DMSO concentration did not exceed 5.25%. The reaction was terminated with the addition of 1M MES, pH 5.8. Fluorescence of the N-terminal product was monitored on a Perkin-Elmer LS-50B fluorometer equipped with a 96-well plate reader (excitation wavelength: 325 nm; emission wavelength: 423 nm).

The % inhibition was calculated with the following equation:

$$100-[(\text{counts}_{inh}-\text{counts}_{blank})/(\text{counts}_{ctr}-\text{counts}_{blank})\times 100]$$

A non-linear curve fit with the Hill model was applied to the inhibition-concentration data, and the 50% effective concentration ($IC_{50}$) was calculated by the use of SAS software (Statistical Software System; SAS Institute, Inc. Cary, N.C.).

Example 39
NS3 Protease Cell-based Assay

This assay was done with Huh-7 cells, a human cell line derived from a hepatoma, co-transfected with 2 DNA constructs:

one expressing a polyprotein comprising the HCV nonstructural proteins fused to tTA in the following order: NS3-NS4A-NS4B-NS5A-tTA (called NS3);

the other expressing the reporter protein, secreted alkaline phosphatase, under the control of tTA (called SEAP).

The polyprotein must be cleaved by the NS3 protease for the mature proteins to be released. Upon release of the mature proteins, it is believed that the viral proteins will form a complex at the membrane of the endoplasmic reticulum while tTA will migrate to the nucleus and transactivate the SEAP gene. Therefore, reduction of NS3 proteolytic activity should lead to reduction of mature tTA levels and concomitant decrease in SEAP activity.

To control for other effects of the compounds, a parallel transfection was done where a construct expressing tTA alone (called tTA) was co-transfected with the SEAP construct such that SEAP activity is independent of NS3 proteolytic activity. Protocol of the assay: Huh-7 cells, grown in CHO-SFMII+10% FCS (fetal calf serum), were co-transfected with either NS3 and SEAP or tTA and SEAP, using the FuGene protocol (Boehringer Mannheim). After 5 h at 37°, the cells were washed, trypsinized and plated (at 80 000 cells/well) in 96-well plates containing a range of concentrations of the compounds to be tested. After a 24-h incubation period, an aliquot of the medium was drawn and the SEAP activity in this aliquot was measured with the Phospha-Light kit (Tropix).

Analysis of the percent inhibition of SEAP activity with respect to compound concentration was performed with the SAS software to obtain the $EC_{50}$.

The toxicity of the compound ($TC_{50}$) was then assessed using the MTT assay as follows:

20 μL of a MTT solution (5 mg/ml medium) was added per well and incubated at 37° for 4 hrs;

the medium was removed and 50 μl of 0.01N HCl+10% Triton X-100 was added;

after shaking at RT for at least 1 hr, the OD of each well was read at 595 nm wavelength.

The $TC_{50}$ was calculated in the same way as the $EC_{50}$.

Example 40
Specificity Assays

The specificity of the compounds was determined against a variety of serine proteases: human leukocyte elastase, porcine pancreatic elastase and bovine pancreatic α-chymotrypsin and one cysteine protease: human liver cathepsin B. In all cases a 96-well plate format protocol using a calorimetric p-nitroaniline (pNA) substrate specific for each enzyme was used. Each assay included a 1 h enzyme-inhibitor pre-incubation at 30° C. followed by addition of substrate and hydrolysis to ≈30% conversion as measured on a UV Thermomax® microplate reader. Substrate concentrations were kept as low as possible compared to $K_M$ to reduce substrate competition. Compound concentrations varied from 300 to 0.06 μM depending on their potency.

The final conditions for each assay were as follows:

50 mM Tris-HCl pH 8, 0.5 M $Na_2SO_4$, 50 mM NaCl, 0.1 mM EDTA, 3% DMSO, 0.01% Tween-20 with;

[100 μM Succ-AAPF-pNA and 250 pM α-chymotrypsin],
[133 μM Succ-AAA-pNA and 8 nM porcine elastase],
[133 μM Succ-AAV-pNA and 8 nM leukocyte elastase];
or

[100 mM $NaHPO_4$ pH 6, 0.1 mM EDTA, 3% DMSO, 1 mM TCEP, 0.01% Tween-20, 30 μM Z-FR-pNA and 5 nM cathepsin B (the stock enzyme was activated in buffer containing 20 mM TCEP before use)].

A representative example is summarized below for porcine pancreatic elastase: In a polystyrene flat-bottom 96-well plate were added using a Biomek liquid handler (Beckman):

40 μL of assay buffer (50 mM Tris-HCl pH 8, 50 mM NaCl, 0.1 mM EDTA);

20 μL of enzyme solution (50 mM Tris-HCl pH 8, 50 mM NaCl, 0.1 mM EDTA, 0.02% Tween-20, 40 nM porcine pancreatic elastase); and 20 μL of inhibitor solution (50 mM Tris-HCl, pH 8, 50 mM NaCl, 0.1 mM EDTA, 0.02% Tween-20, 1.5 mM-0.3 μM inhibitor, 15% v/v DMSO).

After 60 min pre-incubation at 30° C., 20 μL of substrate solution (50 mM Tris-HCl, pH 8, 0.5 M $Na_2SO_4$, 50 mM NaCl, 0.1 mM EDTA, 665 μM Succ-AAA-pNA) were added to each well and the reaction was further incubated at 30° C. for 60 min after which time the absorbance was read on the UV Thermomax® plate reader. Rows of wells were allocated for controls (no inhibitor) and for blanks (no inhibitor and no enzyme).

The sequential 2-fold dilutions of the inhibitor solution were performed on a separate plate by the liquid handler using 50 mM Tris-HCl pH 8, 50 mM NaCl, 0.1 mM EDTA, 0.02% Tween-20, 15% DMSO. All other specificity assays were performed in a similar fashion.

The percentage of inhibition was calculated using the formula:

$$[1((UVinh-UVblank)/(UVctl-UVblank))]\times 100$$

A non-linear curve fit with the Hill model was applied to the inhibition-concentration data, and the 50% effective concentration ($IC_{50}$) was calculated by the use of SAS software (Statistical Software System; SAS Institute, Inc., Cary, N.C.).

Table of Compounds

The following tables list compounds representative of the invention. Compounds of the invention were assayed either in one or both of the assays of Examples 37 and 38 and were found to be active with $IC_{50}$ below 50 μM.

Activity in Cells and Specificity

Representative compounds of the invention were also tested in the surrogate cell-based assay of Example 39, and in one or several assays of Example 40. For example, compound 601 from Table 6 was found to have an $IC_{50}$ of 50 nM in the assay of Example 37 and 30 nM in the assay of Example 38. The $EC_{50}$ as determined by the assay of Example 39 is 8.2 μM. In the specificity assays of Example 40, the same compound was found to have the following activity: HLE>75 μM; PPE>75 μM; α-Chym.>75 μM; Cat. B>75 μM. These results indicate that this family of compounds is highly specific for the NS3 protease and at least certain members of this family are active in a surrogate cell-based assay.

The following abbreviations are used within the present tables:

MS: Mass spectrometric data; Ac: acetyl; Bn: benzyl; Boc: tert-butyloxycarbonyl; cHex: cyclohexyl; Chg: cyclohexylglycine (2-amino-2-cyclohexyl-acetic acid); iPr: isopropyl; O-Bn: benzyloxy; Ph: phenyl: t-Bu: tert-butyl; Tbg: tert-butylglycine; 1- or 2-Np: 1- or 2-naphthyl; 1- or 2-$NpCH_2O$: 1, or 2-naphthylmethoxy.

TABLE 1

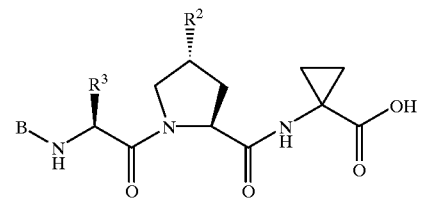

| Tab 1 Cpd # | B | $R_3$ | $R_2$ | MS | $IC_{50}$ (μM) |
|---|---|---|---|---|---|
| 101 | Boc | cHex | —O—$CH_2$-1-naphthyl | 594 | 43 |
| 102 | 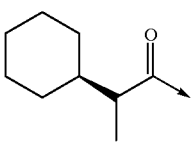 | cHex | —O—$CH_2$-1-naphthyl | 632 | 45 |

TABLE 1-continued
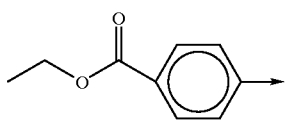
| Tab 1 Cpd # | B | R₃ | R₂ | MS | IC$_{50}$ ($\mu$M) |
|---|---|---|---|---|---|
| 103 | 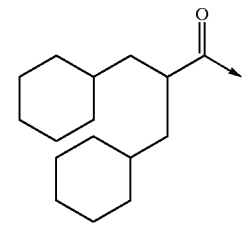 | cHex | —O—CH$_2$-1-naphthyl | 642 | 42 |
| 104 | 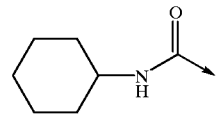 | cHex | —O—CH$_2$-1-naphthyl | 728 | 29.5 |
| 105 | 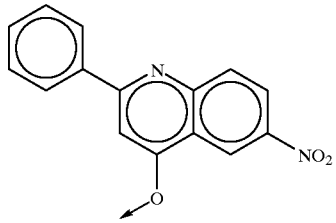 | cHex | —O—CH$_2$-1-naphthyl | 619 | 47 |
| 106 | Boc | cHex | 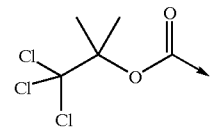 | 702 | 2.8 |
| 107 | 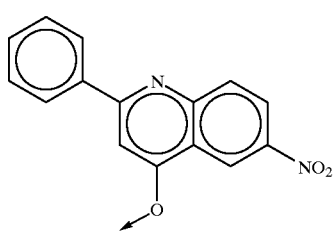 | cHex | —O—CH$_2$-1-naphthyl | 720 M + Na⁺ | 34 |
| 108 | Boc | iPr | 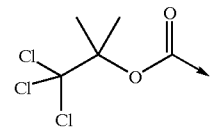 | 662 | 8.9 |

TABLE 1-continued
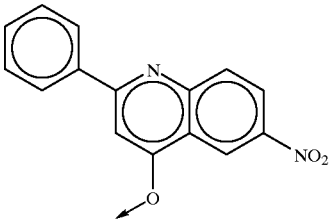
| Tab 1 Cpd # | B | R₃ | R₂ | MS | IC₅₀ ($\mu$M) |
|---|---|---|---|---|---|
| 109 | acetyl | cHex | 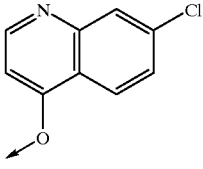 | 644 | 6.3 |
| 110 | Boc | i-Pr | | 575.1 | 9.7 |
| 111 | Boc | t-Bu | | 661.3 | 0.475 |
TABLE 2
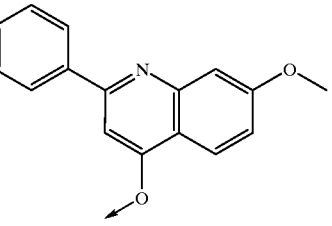
| Table 2 Cpd # | B | R₃ | R₂ | R₁ anti to carboxy | MS | IC₅₀ ($\mu$M) |
|---|---|---|---|---|---|---|
| 201 | Boc | cyclohexyl | —O—CH₂-1-naphthyl | ethyl (one isomer) | 622 | 15 |
| 202 | Boc | cyclohexyl | —O—CH₂-1-naphthyl | ethyl (other isomer) | 622 | 40 |

TABLE 2-continued
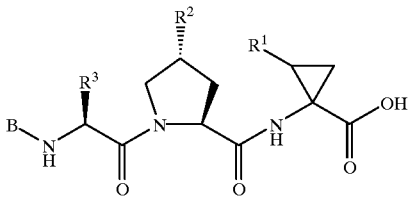
| Table 2 Cpd # | B | $R_3$ | $R_2$ | $R_1$ anti to carboxy | MS | $IC_{50}$ ($\mu M$) |
|---|---|---|---|---|---|---|
| 203 | Boc | t-Bu | 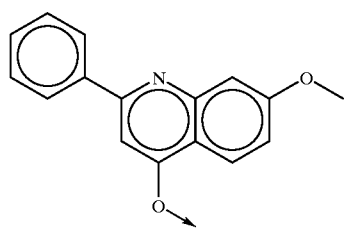 | vinyl 1R, 2R | 687.5 | 0.082 |
TABLE 3
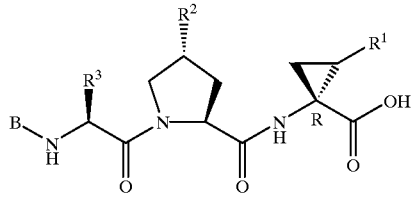
| Table 3 Cpd # | B | $R_3$ | $R_2$ | $R_1$ syn to carboxyl | MS | $IC_{50}$ ($\mu M$) |
|---|---|---|---|---|---|---|
| 301 | Boc | cHex | —O—CH$_2$-1-naphthyl | ethyl | 622 | 7.7 |
| 302 | 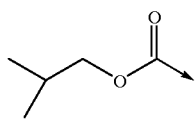 | iPr | -O-CH$_2$-1-naphthyl | ethyl | 582 | 12.5 |
| 303 | 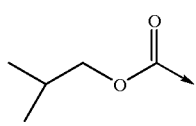 | cHex | —O—CH$_2$-1-naphthyl | ethyl | 622 | 11 |
| 304 | Boc | cHex | 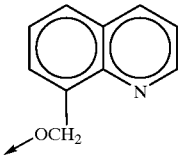 | ethyl | 623 | 32 |
| 305 | Boc | cHex | —O—CH$_2$-1-naphthyl | vinyl | 620 | 3.2 |

TABLE 3-continued
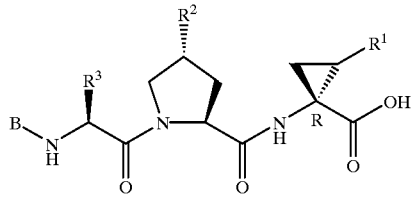
| Table 3 Cpd # | B | R₃ | R₂ | R₁ syn to carboxyl | MS | IC₅₀ ($\mu$M) |
|---|---|---|---|---|---|---|
| 306 | Boc | cHex | 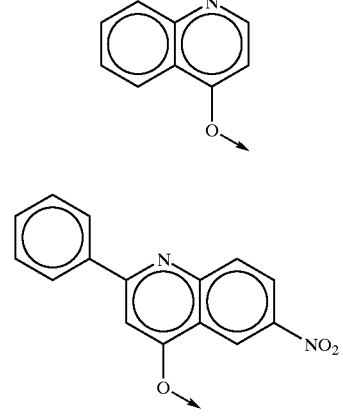 | vinyl | 607 | 0.8 |
| 307 | Boc | cHex | 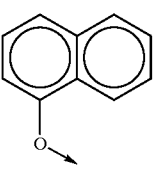 | vinyl | 728 | 0.27 |
| 308 | Boc | cHex | 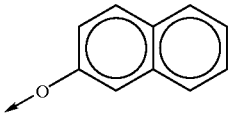 | vinyl | 606 | 1.6 |
| 309 | Boc | cHex | 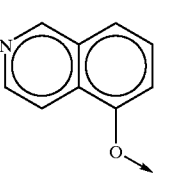 | vinyl | 606 | 5 |
| 310 | Boc | cHex | 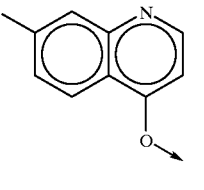 | vinyl | 607 | 2.5 |
| 311 | Boc | cHex | 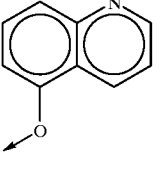 | vinyl | 641 | 0.56 |
| 312 | Boc | cHex |  | vinyl | 607 | 8.5 |

TABLE 3-continued
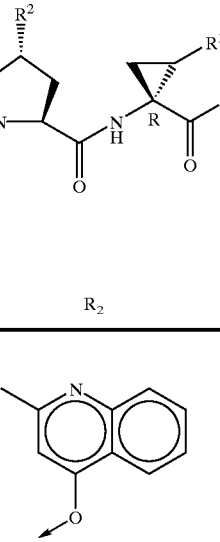
| Table 3 Cpd # | B | $R_3$ | $R_2$ | $R_1$ syn to carboxyl | MS | $IC_{50}$ ($\mu M$) |
|---|---|---|---|---|---|---|
| 313 | Boc | cHex | 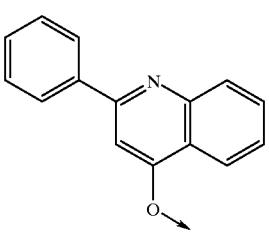 | vinyl | 621 | 2.5 |
| 314 | Boc | cHex | 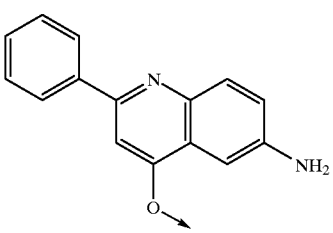 | vinyl | 683 | 0.14 |
| 315 | Boc | cHex | 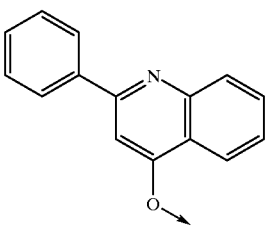 | vinyl | 698 | 0.66 |
| 316 | Acetyl | cHex | 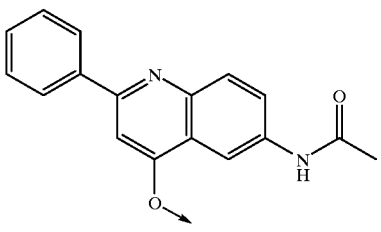 | vinyl | 625 | 1.9 |
| 317 | Boc | cHex |  | vinyl | 740 | 0.32 |

TABLE 3-continued
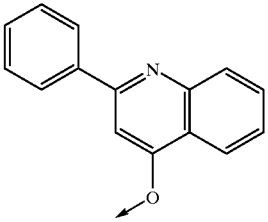
| Table 3 Cpd # | B | R₃ | R₂ | R₁ syn to carboxyl | MS | IC₅₀ ($\mu$M) |
|---|---|---|---|---|---|---|
| 318 | CF₃—C(O)— | i-Pr | 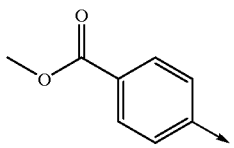 | vinyl | 639.3 | 0.88 |
| 319 | 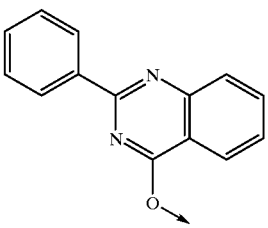 | cHex | 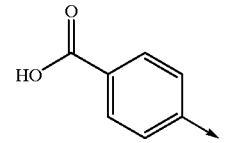 | vinyl | 732.3 | 1.2 |
| 320 | 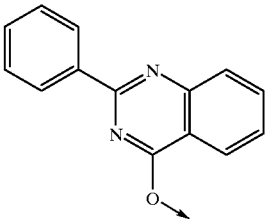 | cHex | 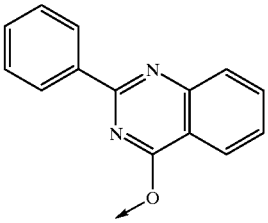 | vinyl | 704.3 | 0.65 |
| 321 | Boc | t-Bu | 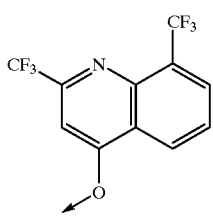 | vinyl | 658.7 | 0.19 |
| 322 | Boc | t-Bu |  | vinyl | 717.6 | 1.95 |

TABLE 3-continued
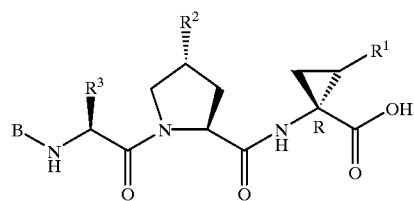
| Table 3 Cpd # | B | R₃ | R₂ | R₁ syn to carboxyl | MS | IC₅₀ (μM) |
|---|---|---|---|---|---|---|
| 323 | Boc | t-Bu | 2-phenylquinazolin-4-yloxy | cyclopropyl | 672.4 | 0.64 |
| 324 | Boc | t-Bu | 2-morpholino-6,7-dimethoxyquinazolin-4-yloxy | vinyl | 727.5 | 0.05 |
| 325 | Boc | t-Bu | 2-phenyl-7-methoxyquinolin-4-yloxy | cyclopropyl | 701.4 | 0.153 |
| 326 | Boc | t-Bu | 2-(imidazol-1-yl)-6,7-dimethoxyquinazolin-4-yloxy | vinyl | 708.3 | 0.32 |
| 327 | t-Bu-NH-C(O)- | t-Bu | 7-methoxyquinolin-4-yloxy | vinyl | 610.3 | 0.045 |
| 328 | Boc | t-Bu | 4-chloroquinolin-2-yloxy | vinyl | 615.3 | 3.2 |

TABLE 3-continued

| Table 3 Cpd # | B | R₃ | R₂ | R₁ syn to carboxyl | MS | IC₅₀ (μM) |
|---|---|---|---|---|---|---|
| 329 | Boc | t-Bu | 2,2':6',2''-terpyridin-4'-yloxy | vinyl | 685.3 | 0.36 |
| 330 | Boc | t-Bu | 2-acetyl-1,2,3,4-tetrahydroisoquinolin-5-yloxy | vinyl | 627.5 | 6 |
| 331 | t-BuNHC(O)CH₂- | t-Bu | 2-phenylquinolin-4-yloxy | vinyl | 656.5 | 0.071 |
| 332 | Boc | t-Bu | 7-methoxy-2-phenylquinolin-4-yloxy | ethyl | 689.3 | 0.13 |
| 333 | (S)-t-Bu-CH(Me)NHC(O)CH₂- | t-Bu | 2-(2-acetamidothiazol-4-yl)-7-methoxyquinolin-4-yloxy | vinyl | 778.3 | 0.003 |

TABLE 3-continued

| Table 3 Cpd # | B | R₃ | R₂ | R₁ syn to carboxyl | MS | IC₅₀ (μM) |
|---|---|---|---|---|---|---|
| 334 | | t-Bu | | vinyl | 764.4 | 0.007 |

TABLE 4

| Table 4 Cpd # | B | R₃ | R₂ | R₁ | MS | IC₅₀ (μM) |
|---|---|---|---|---|---|---|
| 401 | Boc | i-Pr | | H | 589.1 | 5.8 |
| 402 | Boc | t-Bu | | H | 603.6 | 7.9 |

TABLE 4-continued
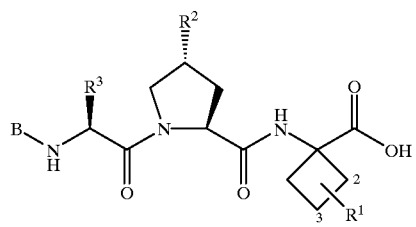
| Table 4 Cpd # | B | $R_3$ | $R_2$ | $R_1$ | MS | IC$_{50}$ ($\mu$M) |
|---|---|---|---|---|---|---|
| 403 | Boc | t-Bu | 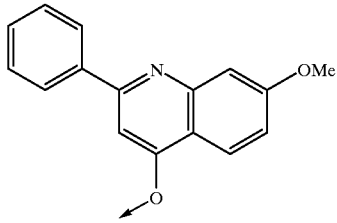 | H | 675.4 | 0.132 |
| 404 | Boc | t-Bu | 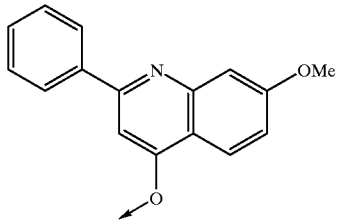 | 3-(=CH$_2$) | 687.1 | 0.6 |
| 405 | Boc | t-Bu | 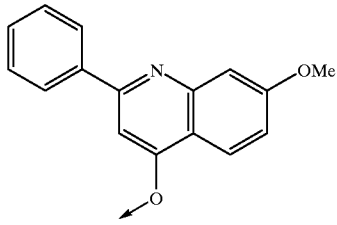 | 2-vinyl | 702.3 | 0.220 |
| 406 | Boc | t-Bu | 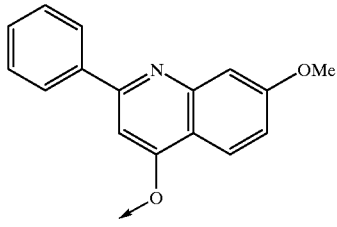 | 2-Et | 703.3 | 0.4 |

TABLE 5

| Table 5 Cpd # | R3 | MS | IC50 (μM) |
|---|---|---|---|
| 501 | t-Bu | 581.3 | 0.4 |
| 502 | H | 539.2 | 6.2 |
| 503 | (tert-butoxy-methyl) | 625.3 | 0.79 |
| 504 | (methoxy-methyl, S) | 582.6 | 2.6 |
| 505 | (methoxy-methyl, R) | 583.2 | 0.79 |
| 506 | (benzyloxy-methyl) | 659.2 | 1.3 |
| 507 | (acetamido-methylthio-tBu) | 670.2 | 0.98 |

TABLE 5-continued

| Table 5 Cpd # | R3 | MS | IC50 (μM) |
|---|---|---|---|
| 508 | (4-methylbenzyl-thio-tBu) | 703.3 | 3.1 |
| 509 | (sec-butyl, S) | 581.3 | 0.377 |
| 510 | (sec-butyl, R) | 581.2 | 0.255 |
| 511 | (cyclohexyl-hydroxymethyl) | 637.2 | 2.1 |

TABLE 6
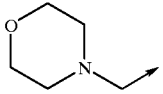
| Table 6 Cpd # | R₃ | R₂₁ₐ | R₂₁ᵦ | MS | IC₅₀ (μM) |
|---|---|---|---|---|---|
| 601 | i-Pr | Ph | 7-OMe | 673.3 | 0.05 |
| 602 | t-Bu | Ph | 8-OMe, 7-OMe | 717.2 | 0.041 |
| 603 | i-Pr | Ph | 7-ethyl | 671.2 | 0.195 |
| 604 | t-Bu | — | 7-OMe | 611.2 | 0.073 |
| 605 | t-Bu | Ph | 7-O—iPr | 715.3 | 0.195 |
| 606 | t-Bu | — | 7-Cl | 615.2 | 0.48 |
| 607 | iPr | — | 7-Cl | 601.2 | 0.45 |
| 608 | CH₂—iPr | — | 7-Cl | 615.3 | 1.45 |
| 609 | t-Bu | 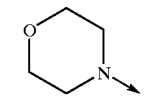 | — | 680.2 | 1.7 |
| 610 | t-Bu | Cl | — | 613.3 | 0.25 |
| 611 | t-Bu | Ph | 7-N(Me)₂ | 700.5 | 0.035 |
| 612 | t-Bu | 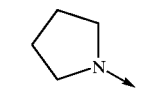 | — | 666.4 | 0.278 |
| 613 | t-Bu | 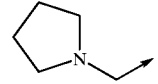 | — | 650.4 | 1.0 |
| 614 | t-Bu | 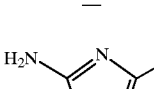 | — | 664.5 | 2.2 |
| 615 | t-Bu | — | 7-N(Me)₂ | 624.5 | 0.16 |
| 616 | t-Bu | 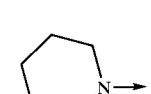 | — | 678.4 (M − H)⁺ | 0.087 |
| 617 | t-Bu | 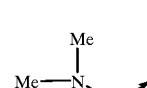 | — | 664.5 | 0.345 |
| 618 | t-Bu | 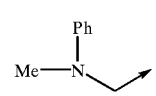 | — | 638.5 | 2.3 |
| 619 | t-Bu |  | — | 700.5 | 3.0 |

TABLE 6-continued
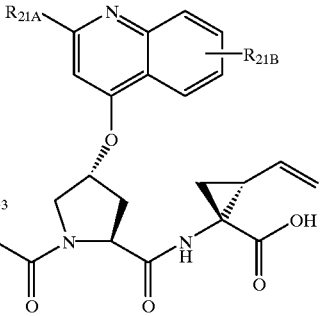
| Table 6 Cpd # | R$_3$ | R$_{21A}$ | R$_{21B}$ | MS | IC$_{50}$ ($\mu$M) |
|---|---|---|---|---|---|
| 620 | t-Bu | 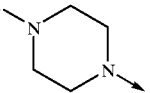 | — | 679.5 | 0.72 |
| 621 | t-Bu | 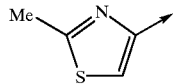 | — | 678.3 | 0.058 |
| 622 | t-Bu | 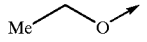 | — | 625.4 | 0.16 |
| 623 | t-Bu | MeO— | — | 611.3 | 0.20 |
| 624 | t-Bu | (Me)$_2$N— | — | 624.4 | 1.30 |
| 625 | t-Bu | Ph | 7-S(Me) | 703.4 | 0.16 |
| 626 | t-Bu | Ph | 7-Br | 737.3 | 0.24 |
| 627 | t-Bu | Ph | 7-F | 675.3 | 0.33 |
| 628 | t-Bu | 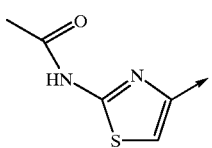 | 7-N(Me)$_2$ | 764.2 | 0.011 |
| 629 | t-Bu | 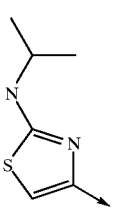 | 7-N(Me)$_2$ | 764.3 | 0.02 |
| 630 | t-Bu | 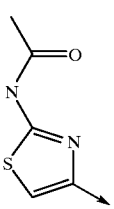 | 7-N(Et)$_2$ | 792.3 | 0.043 |

TABLE 7
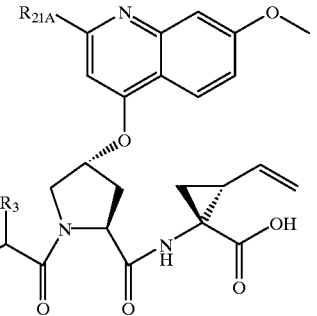
| Table 7 Cpd # | R₃ | R₂₁ₐ | MS | IC₅₀ (μM) |
|---|---|---|---|---|
| 701 | t-Bu | 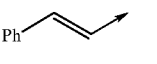 | 691.3 | 0.028 |
| 702 | t-Bu | 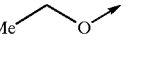 | 713.4 | 0.10 |
| 703 | t-Bu | 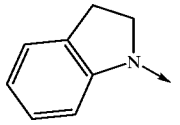 | 655.3 | 0.047 |
| 704 | t-Bu | 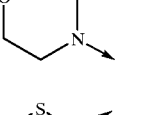 | 728.4 | 0.24 |
| 705 | t-Bu | 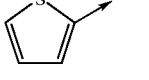 | 696.4 | 0.13 |
| 706 | t-Bu | 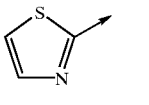 | 693.3 | 0.032 |
| 707 | t-Bu | 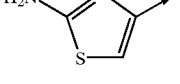 | 694.3 | 0.023 |
| 708 | t-Bu | Ph—N(Me)— | 716.4 | 0.15 |
| 709 | t-Bu | 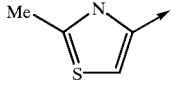 | 709.2 | 0.021 |
| 710 | t-Bu | HOOC— | 655.3 | 0.685 |
| 711 | t-Bu | 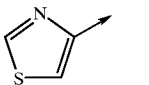 | 708.2 | 0.016 |
| 712 | t-Bu | (Me)₂N— | 654.3 | 0.10 |
| 713 | t-Bu | 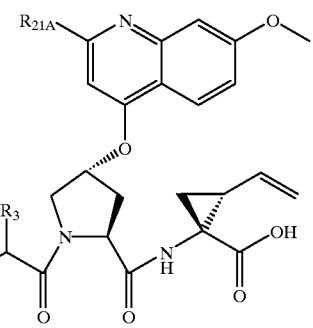 | 692.3 (M-H) | 0.026 |
TABLE 7-continued
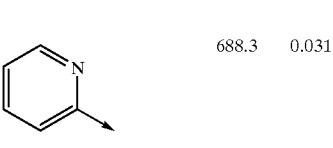
| Table 7 Cpd # | R₃ | R₂₁ₐ | MS | IC₅₀ (μM) |
|---|---|---|---|---|
| 714 | t-Bu | 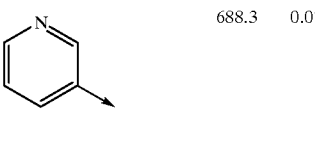 | 722.3 | 0.012 |
| 715 | t-Bu | 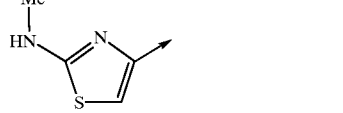 | 688.3 | 0.031 |
| 716 | t-Bu | 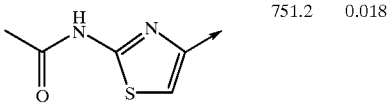 | 688.3 | 0.079 |
| 717 | t-Bu | 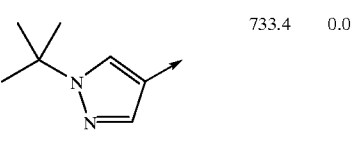 | 723.3 | 0.028 |
| 718 | t-Bu | NH₂ | 626.3 | 0.16 |
| 719 | t-Bu | 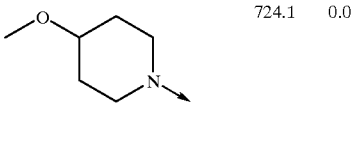 | 751.2 | 0.018 |
| 720 | t-Bu | 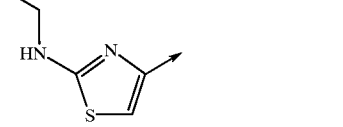 | 733.4 | 0.03 |
| 721 | t-Bu |  | 724.1 | 0.045 |
| 722 | t-Bu |  | 737.3 | 0.048 |

TABLE 7-continued

| Table 7 Cpd # | R₃ | R₂₁ₐ | MS | IC₅₀ (μM) |
|---|---|---|---|---|
| 723 | t-Bu | HN-isopropyl-thiazol-4-yl | 751.4 | 0.047 |
| 724 | t-Bu | 4-methylpiperidin-1-yl | 708.4 | 0.075 |
| 725 | t-Bu | pyrimidin-4-yl | 689.4 | 0.046 |
| 726 | t-Bu | i-Pr | 653.3 | 0.25 |
| 727 | t-Bu | pyridin-3-yl | 688.3 | 0.07 |
| 728 | t-Bu | methylsulfonylmethyl-thiazol-4-yl | 786.1 | 0.022 |
| 729 | t-Bu | pyrazin-2-yl | 689.3 | 0.2 |
| 730 | t-Bu | isopropoxy | 669.2 | 0.042 |
| 731 | t-Bu | n-propoxy | 669.2 | 0.031 |
| 732 | t-Bu | 2-methylthiazol-4-yl-thiazol-4-yl | 791.0 | 0.02 |
| 733 | t-Bu | t-butylamino-thiazol-4-yl | 765.3 | 0.028 |
| 734 | t-Bu | ethylthio | 671.3 | 0.044 |
| 735 | t-Bu | isobutoxy | 683.3 | 0.058 |
| 736 | t-Bu | t-Bu | 667.4 | 0.25 |
| 737 | t-Bu | CHex | 693.4 | 0.11 |

TABLE 8

| Table 8 Cpd # | B | R₃ | R₂₂ | MS | IC₅₀ ($\mu$M) |
|---|---|---|---|---|---|
| 801 | (t-butyl carbamoyl) | t-Bu | — | 686.7 | 0.006 |
| 802 | (hydroxy cyclohexyl acetyl) | t-Bu | — | 727.7 | 0.024 |
| 803 | (neohexanoyl) | t-Bu | — | 685.7 | 0.12 |
| 804 | (cyclohexylacetyl) | t-Bu | — | 711.7 | 0.032 |
| 805 | Ac | t-Bu | — | 629.6 | 0.083 |
| 806 | (2-cyclohexylpropanoyl) | t-Bu | — | 725.7 | 0.036 |
| 807 | (isopropyl carbamoyl) | t-Bu | — | 672.4 | 0.01 |
| 808 | (cyclohexyl carbamoyl) | t-Bu | — | 712.4 | 0.008 |

TABLE 8-continued
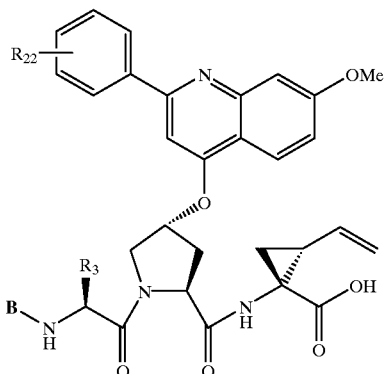
| Table 8 Cpd # | B | $R_3$ | $R_{22}$ | MS | $IC_{50}$ ($\mu M$) |
|---|---|---|---|---|---|
| 809 | (phenyl) | i-Pr | — | 649.3 | 0.071 |
| 810 | (2,6-dimethylphenoxyacetyl) | t-Bu | — | 749.3 | 0.45 |
| 811 | Boc | t-Bu | 4-Cl | 721.3 | 0.04 |
| 812 | (phenyl-NH-C(O)-) | t-Bu | — | 706.2 | 0.013 |
| 813 | (t-Bu-NH-C(S)-) | t-Bu | — | 702.2 | 0.02 |
| 814 | Boc | t-Bu | 2-Cl | 721.3 | 0.13 |
| 815 | Boc | t-Bu | 3-Cl | 721.3 | 0.16 |
| 816 | (Et-NH-C(O)-) | t-Bu | — | 658.3 | 0.032 |
| 817 | (Bn-NH-C(O)-) | t-Bu | — | 720.2 | 0.017 |
| 818 | (cyclohexyl-NH-C(S)-) | t-Bu | — | 728.3 | 0.019 |
| 819 | (C$_2$N, CF$_3$-phenyl) | i-Pr | — | 762.3 | 0.32 |

TABLE 8-continued
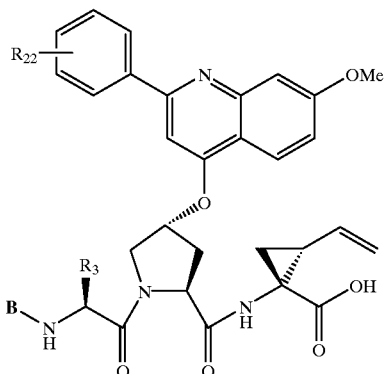
| Table 8 Cpd # | B | R$_3$ | R$_{22}$ | MS | IC$_{50}$ ($\mu$M) |
|---|---|---|---|---|---|
| 820 | H$_2$N—⟨CF$_3$⟩— | i-Pr | — | 732.2 | 0.063 |
| 821 | MeO—⟨ ⟩— | i-Pr | — | 679.1 | 0.12 |
| 822 | Me—⟨ ⟩— | i-Pr | — | 663.3 | 0.05 |
| 823 | Boc | t-Bu | 2-OMe | 717.2 | 0.107 |
| 824 | Boc | t-Bu | 3-OMe | 719.2 | 0.07 |
| 825 | Boc | t-Bu | 4-OMe | 719.2 | 0.024 |
| 826 | ⟨ ⟩—CH$_2$— | 1-Pr | — | 663.3 | 0.78 |
| 827 | Me$_2$N—N(Me)—C(O)— | t-Bu | — | 673.2 | 0.27 |
| 828 | Me-C(O)—⟨ ⟩— | i-Pr | — | 691.3 | 0.10 |
| 829 | 2,6-Me$_2$-C$_6$H$_3$-NH-C(O)— | t-Bu | — | 734.3 | 0.057 |
| 830 | MeO-C(O)— | t-Bu | — | 645.3 | 0.111 |

TABLE 8-continued
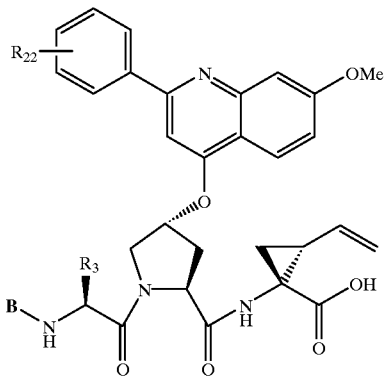
| Table 8 Cpd # | B | $R_3$ | $R_{22}$ | MS | $IC_{50}$ ($\mu M$) |
|---|---|---|---|---|---|
| 831 | H₂N–C(=O)–CH(Me)–NH–C(=O)– | t-Bu | — | 701.3 | 0.015 |
| 832 | H₂N–C(=O)–CH(Me)–NH–C(=O)– | t-Bu | — | 801.3 | 0.11 |
| 833 | H₂N–C(=O)–C(Me)(Me)–NH–C(=O)– | t-Bu | — | 715.2 | 0.015 |
| 834 | 3-Me-C₆H₄– | i-Pr | — | 663.3 | 0.074 |
| 835 | HO–C(=O)–C(Me)(Me)–NH–C(=O)– | t-Bu | — | 702.5 | 0.007 |
| 836 | 4-O₂N-C₆H₄– | i-Pr | — | 694.4 | 0.13 |
| 837 | 4-Cl-C₆H₄– | i-Pr | — | 883.3 | 0.098 |
| 838 | 3-HOCH₂-C₆H₄– | i-Pr | — | 679.1 | 0.094 |

TABLE 8-continued

| Table 8 Cpd # | B | R₃ | R₂₂ | MS | IC₅₀ ($\mu$M) |
|---|---|---|---|---|---|
| 839 | NC-C₆H₄- | i-Pr | — | 674.5 | 0.10 |
| 840 | F-C₆H₄- | i-Pr | — | 667.4 | 0.085 |
| 841 | Boc | t-Bu | 2-Me | 701.5 | 0.24 |
| 842 | Boc | t-Bu | 3-Me | 701.5 | 0.073 |
| 843 | Boc | t-Bu | 4-Me | 701.5 | 0.053 |
| 844 | t-Bu-CH₂-C(O)- | t-Bu | 4-OMe | 716.6 | 0.006 |
| 845 | 4-AcNH-C₆H₄- | i-Pr | — | 706.9 | 0.18 |
| 846 | 3,4-methylenedioxyphenyl | i-Pr | — | 693.4 | 0.104 |
| 847 | Boc | cHex | — | 713.4 | 0.037 |
| 848 | Boc | i-Bu | — | 687.5 | 0.093 |
| 849 | Boc | neopentyl | — | 701.5 | 0.110 |
| 850 | Boc | CH(CH₃)O-tBu | — | 731.5 | 0.063 |

TABLE 8-continued

| Table 8 Cpd # | B | R₃ | R₂₂ | MS | IC₅₀ (μM) |
|---|---|---|---|---|---|
| 851 | Boc | -O-Me (α) | — | 689.5 | 0.12 |
| 852 | Boc | -O-Me (β) | — | 689.5 | 0.17 |
| 853 | Boc | -OBn | — | 765.5 | 0.17 |
| 854 | biphenyl | i-Pr | — | 723.4 (M-H)⁺ | 0.37 |
| 855 | HO-CH₂CH₂-phenyl | i-Pr | — | 6933 | 0.675 |
| 856 | NC-CH₂-phenyl | i-Pr | — | 688.3 | 0.11 |
| 857 | MeO-C(Me)₂-CH₂-NH-C(O)- | t-Bu | — | 716.4 | 0.011 |
| 858 | t-Bu-N(Me)-C(O)- | t-Bu | — | 700.4 | 0.205 |

TABLE 8-continued
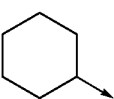
| Table 8 Cpd # | B | R₃ | R₂₂ | MS | IC₅₀ ($\mu$M) |
|---|---|---|---|---|---|
| 859 | 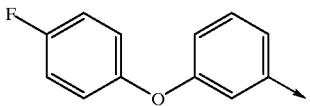 | i-Pr | — | 655.4 | 0.83 |
| 860 | 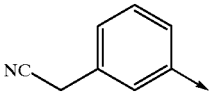 | i-Pr | — | 759.3 | 0.24 |
| 861 | 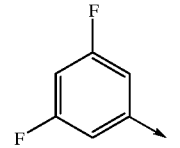 | i-Pr | — | 688.3 | 0.17 |
| 862 | 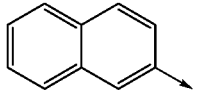 | i-Pr | — | 685.3 | 0.23 |
| 863 | 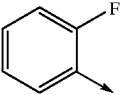 | i-Pr | — | 699.4 | 0.30 |
| 864 | 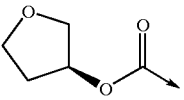 | i-Pr | — | 667.3 | 0.45 |
| 865 | 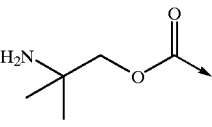 | t-Bu | — | 701.4 | 0.02 |
| 866 |  | t-Bu | — | 702.4 | 0.20 |

TABLE 8-continued
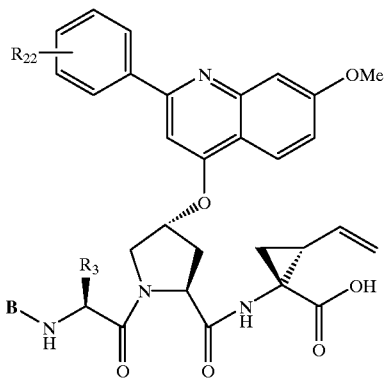
| Table 8 Cpd # | B | R₃ | R₂₂ | MS | IC₅₀ (μM) |
|---|---|---|---|---|---|
| 867 | 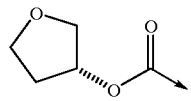 | t-Bu | — | 701.3 | 0.051 |
| 868 | 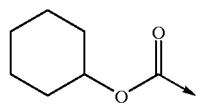 | t-Bu | — | 713.3 | 0.03 |
| 869 | 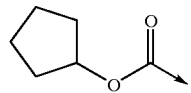 | t-Bu | — | 699.4 | 0.014 |
| 870 | 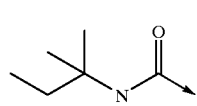 | t-Bu | — | 700.4 | 0.009 |
| 871 | 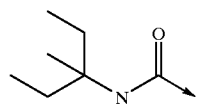 | t-Bu | — | 714.3 | 0.011 |
| 872 | 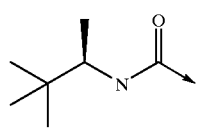 | t-Bu | — | 714.4 | 0.005 |

TABLE 8-continued

| Table 8 Cpd # | B | R$_3$ | R$_{22}$ | MS | IC$_{50}$ ($\mu$M) |
|---|---|---|---|---|---|
| 873 | (structure) | t-Bu | — | 714.3 | 0.019 |

TABLE 9

| Table 9 Cpd # | B | MS | IC$_{50}$ ($\mu$M) |
|---|---|---|---|
| 901 | Boc | 685.3 | 0.025 |
| 902 | (structure) | 825.4 | 0.042 |
| 903 | (structure) | 769.3 | 0.005 |
| 904 | (structure) | 707.3 | 0.095 |
| 905 | (structure) | 685.2 | 0.029 |
| 906 | (structure) | 728.2 | 0.014 |

TABLE 9-continued

| Table 9 Cpd # | B | MS | IC$_{50}$ ($\mu$M) |
|---|---|---|---|
| 907 | tetrahydrothiophen-3-yl carbamate | 717.2 | 0.025 |
| 908 | benzoyl | 691.2 | 0.072 |
| 909 | phenylsulfonyl | 727.2 | 0.036 |
| 910 | 3,3-dimethylbutan-2-yl carbamate | 715.3 | 0.056 |
| 911 | 3-hydroxy-2-methylbenzoyl | 721.3 | 0.039 |
| 912 | thiophen-2-ylsulfonyl | 733.2 | 0.034 |
| 913 | thiazol-2-yl carbamoyl | 713.3 | 0.030 |

TABLE 9-continued

| Table 9 Cpd # | B | MS | IC$_{50}$ ($\mu$M) |
|---|---|---|---|
| 914 | 2-acetamido-4-methylthiazol-5-ylsulfonyl | 805.3 | 0.031 |
| 915 | 4-ethylthiazol-2-yl | 692.2 | 0.026 |
| 916 | 1H-pyrrol-2-ylcarbonyl | 680.3 | 0.3 |

TABLE 10

| Table 10 Cpd # | B-X- | R$_3$ | Z | R$_{21B}$ | MS | IC$_{50}$ ($\mu$M) |
|---|---|---|---|---|---|---|
| 1001 | Ph—N(Me)— | i-Pr | O | H | 663.3 | 0.31 |
| 1002 | Boc-NH— | t-Bu | S | OMe | 703.4 | 0.32 |

TABLE 10-continued

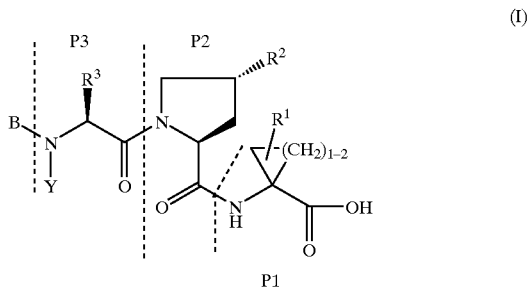

| Table 10 Cpd # | B-X- | R$_3$ | Z | R$_{21B}$ | MS | IC$_{50}$ ($\mu$M) |
|---|---|---|---|---|---|---|
| 1003 | (phenyl-N(Me)-CH-) | i-Pr | O | — | 663.3 | 0.31 |

What is claimed is:

1. A racemate, diastereoisomer or optical isomer of a compound of formula (I):

$$(I)$$

wherein
B is H, a $C_6$ or $C_{10}$ aryl, $C_{7-16}$ aralkyl; Het or (lower alkyl)-Het, all of which optionally substituted with $C_{1-6}$ alkyl; $C_{1-6}$ alkoxy; $C_{1-6}$ alkanoyl; hydroxy; hydroxyalkyl; halo; haloalkyl; nitro; cyano; cyanoalkyl; amino optionally substituted with $C_{1-6}$ alkyl; amido; or (lower alkyl)amide;

or B is an acyl derivative of formula $R_4$—C(O)—; a carboxyl derivative of formula $R_4$—O—C(O)—; an amide derivative of formula $R_4$—N($R_5$)—C(O)—; a thioamide derivative of formula $R_4$—N($R_5$)—C(S)—; or a sulfonyl derivative of formula $R_4$—SO$_2$ wherein $R_4$ is (i) $C_{1-10}$ alkyl optionally substituted with carboxyl, $C_{1-6}$ alkanoyl, hydroxy, $C_{1-6}$ alkoxy, amino optionally mono- or di-substituted with $C_{1-6}$ alkyl, amido, or (lower alkyl) amide;

(ii) $C_{3-7}$ cycloalkyl, $C_{3-7}$ cycloalkoxy, or $C_{4-10}$ alkylcycloalkyl, all optionally substituted with hydroxy, carboxyl, ($C_{1-6}$ alkoxy)carbonyl, amino optionally mono- or di-substituted with $C_{1-6}$ alkyl, amido, or (lower alkyl) amide;

(iii) amino optionally mono- or di-substituted with $C_{1-6}$ alkyl; amido; or (lower alkyl)amide;

(iv) $C_6$ or $C_{10}$ aryl or $C_{7-16}$ aralkyl, all optionally substituted with $C_{1-6}$ alkyl, hydroxy, amido, (lower alkyl)amide, or amino optionally mono- or di-substituted with $C_{1-6}$ alkyl; or (v) Het or (lower alkyl)-Het, both optionally substituted with $C_{1-6}$ alkyl, hydroxy, amido, (lower alkyl) amide, or amino optionally mono- or di-substituted with $C_{1-6}$ alkyl;

$R_5$ is H or $C_{1-6}$ alkyl; with the proviso that when B is a carboxyl derivative, an amide derivative or a thioamide derivative, $R_4$ is not a cycloalkoxy;

Y is H or $C_{1-6}$ alkyl;

$R^3$ is $C_{1-8}$ alkyl, $C_{3-7}$ cycloalkyl, or $C_{4-10}$ alkylcycloalkyl, all optionally substituted with hydroxy, $C_{1-6}$ alkoxy, $C_{1-6}$ thioalkyl, amido, (lower alkyl)amido, $C_6$ or $C_{10}$ aryl, or $C_{7-16}$ aralkyl;

$R^2$ is CH$_2$—$R_{20}$, NH—$R_{20}$, O—$R_{20}$ or S—$R_{20}$, wherein $R_{20}$ is pyrimidinyl, quinazolinyl, (lower alkyl)-pyrimidinyl or (lower alkyl)-quinazolinyl, each optionally mono-, di- or tri-substituted with $R_{21}$, wherein each $R_{21}$ is independently $C_{1-6}$ alkyl; $C_{1-6}$ alkoxy; lower thioalkyl; sulfonyl; NO$_2$; OH; SH; halo; haloalkyl; amino optionally mono- or di-substituted with $C_{1-6}$ alkyl, $C_6$ or $C_{10}$ aryl, $C_{7-14}$ aralkyl, Het or (lower alkyl)-Het; amido optionally mono-substituted with $C_{1-6}$ alkyl, $C_6$ or $C_{10}$ aryl, $C_{7-14}$ aralkyl, Het or (lower alkyl)-Het; carboxyl; carboxy(lower alkyl); $C_6$ or $C_{10}$ aryl, $C_{7-14}$ aralkyl or Het, said aryl, aralkyl or Het being optionally substituted with $R_{22}$;

wherein $R_{22}$ is $C_{1-6}$ alkyl; $C_{3-7}$ cycloalkyl; $C_{1-6}$ alkoxy; amino optionally mono- or di-substituted with $C_{1-6}$ alkyl; sulfonyl; (lower alkyl)sulfonyl; NO$_2$; OH; SH; halo; haloalky; carboxyl; amide; (lower alkyl)amide; or Het optionally substituted with $C_{1-6}$ alkyl;

$R^1$ is H; $C_{1-6}$ alkyl, $C_{3-7}$ cycloalkly, or $C_{2-6}$ alkynyl, all optionally substituted with halogen;

or a pharmaceutically acceptable salt or ester thereof;

wherein "Het" is defined as a five-membered saturatd or unsaturated, aromatic or non-aromatic, heterocycle containing from one to four heteroatoms selected from nitrogen, oxygen and sulfur, wherein said heterocycle is optionally fused to a benzene ring.

2. A compound of formula I according to claim 1, wherein

B is a $C_6$ or $C_{10}$ aryl or $C_{7-16}$ aralkyl, all optionally substituted with $C_{1-6}$ alkyl, $C_{1-6}$ alkoxy, $C_{1-6}$ alkanoyl, hydroxy, hydroxyalkyl, halo, haloalkyl, nitro, cyano, cyanoalkyl, amido, (lower alkyl)amido, or amino optionally substituted with $C_{1-6}$ alkyl; or B is Het or (lower alkyl)-Het, all optionally substituted with $C_{1-6}$ alkyl, $C_{1-6}$ alkoxy, $C_{1-6}$ alkanoyl, hydroxy, hydroxyalkyl, halo, haloalkyl, nitro, cyano, cyanoalkyl, amido, (lower alkyl)amido, or amino optionally substituted with $C_{1-6}$ alkyl.

3. A compound of formula I according to claim 1, wherein B is $R_4$—SO$_2$ wherein $R_4$ is $C_{1-6}$ alkyl; amido; (lower alkyl)amide; $C_6$ or $C_{10}$ aryl, $C_{7-14}$ aralkyl or Het, all optionally substituted with $C_{1-6}$ alkyl.

4. A compound of formula I according to claim 1, wherein B is an acyl derivative of formula $R_4$—C(O)— wherein $R_4$ is (i) $C_{1-10}$ alkyl optionally substituted with carboxyl, hydroxy or $C_{1-6}$ alkoxy, amido, (lower alkyl)amide, or amino optionally mono- or di-substituted with $C_{1-6}$ alkyl;

(ii) $C_{3-7}$ cycloalkyl or $C_{4-10}$ alkylcycloalkyl, both optionally substituted with hydroxy, carboxyl, ($C_{1-6}$ alkoxy) carbonyl, amido, (lower alkyl)amide, or amino optionally mono- or di-substituted with $C_{1-6}$ alkyl;

(iv) $C_6$ or $C_{10}$ aryl or $C_{7-16}$ aralkyl, all optionally substituted with $C_{1-6}$ alkyl, hydroxy, amido, (lower alkyl) amide, or amino optionally substituted with $C_{1-6}$ alkyl;

(v) Het or (lower alkyl)-Het, both optionally substituted with $C_{1-6}$ alkyl, hydroxy, amino optionally substituted with $C_{1-6}$ alkyl, amido, (lower alkyl)amide, or amino optionally substituted with $C_{1-6}$ alkyl.

5. A compound of formula I according to claim 1, wherein B is a carboxyl derivative of formula $R_4$—O—C(O)—, wherein $R_4$ is (i) $C_{1-10}$ alkyl optionally substituted with carboxyl, $C_{1-6}$ alkanoyl, hydroxy, $C_{1-6}$ alkoxy, amino optionally mono- or di-substituted with $C_{1-6}$ alkyl, amido or (lower alkyl)amide;

(ii) $C_{3-7}$ cycloalkyl, $C_{4-10}$ alkylcycloalkyl, all optionally substituted with carboxyl, ($C_{1-6}$ alkoxy)carbonyl, amino optionally mono- or di-substituted with $C_{1-6}$ alkyl, amido or (lower alkyl)amide;

(iv) $C_6$ or $C_{10}$ aryl or $C_{7-16}$ aralkyl optionally substituted with $C_{1-6}$ alkyl, hydroxy, amido, (lower alkyl)amido, or amino optionally mono- or di-substituted with $C_{1-6}$ alkyl; or (v) Het or (lower alkyl)-Het, both optionally substituted with $C_{1-6}$ alkyl, hydroxy, amino optionally mono- or di-substituted with $C_{1-6}$ alkyl, amido or (lower alkyl) amido.

6. A compound of formula I according to claim 1, wherein B is an amide derivative of formula $R_4$—N($R_5$)—C(O)— wherein $R_4$ is (i) $C_{1-10}$ alkyl optionally substituted with carboxyl, $C_{1-6}$ alkanoyl, hydroxy, $C_{1-6}$ alkoxy, amido, (lower alkyl) amido, or amino optionally mono- or di-substituted with $C_{1-6}$ alkyl;

(ii) $C_{3-7}$ cycloalkyl or $C_{4-10}$ alkylcycloalkyl, all optionally substituted with carboxyl, ($C_{1-6}$ alkoxy)carbonyl, amido, (lower alkyl)amido, or amino optionally mono- or di-substituted with $C_{1-6}$ alkyl;

(iii) amino optionally mono- or di-substituted with $C_{1-3}$ alkyl;

(iv) $C_6$ or $C_{10}$ aryl or $C_{7-16}$ aralkyl, all optionally substituted with $C_{1-6}$ alkyl, hydroxy, amido, (lower alkyl) amide, or amino optionally substituted with $C_{1-6}$ alkyl; or (v) Het or (lower alkyl)-Het, both optionally substituted with $C_{1-6}$ alkyl, hydroxy, amino optionally substituted with $C_{1-6}$ alkyl, amido or (lower alkyl)amide; and $R_5$ is H or methyl.

7. A compound of formula I according to claim 1, wherein B is a thioamide derivative of formula $R_4$—NH—C(S)—; wherein $R_4$ is (i) $C_{1-10}$ alkyl optionally substituted with carboxyl, $C_{1-6}$ alkanoyl or $C_{1-6}$ alkoxy;

(ii) $C_{3-7}$ cycloalkyl or $C_{4-10}$ alkylcycloalkyl, all optionally substituted with carboxyl, ($C_{1-6}$ alkoxy)carbonyl, amino or amido.

8. A compound of formula I according to claim 2, wherein B is a $C_6$ or $C_{10}$ aryl optionally substituted with $C_{1-6}$ alkyl, $C_{1-6}$ alkoxy, $C_{1-6}$ alkanoyl, hydroxy, hydroxyalkyl, halo, haloalkyl, nitro, cyano, cyanoalkyl, amido, (lower alkyl) amide, or amino optionally mono- or di-substituted with $C_{1-6}$ alkyl.

9. A compound of formula I according to claim 2, wherein r B is Het optionally substituted with $C_{1-6}$ alkyl, $C_{1-6}$ alkoxy, $C_{1-6}$ alkanoyl, hydroxy, halo, amido, (lower alkyl)amide, or amino optionally mono- or di-substituted with $C_{1-6}$ alkyl.

10. A compound of formula I according to claim 4, wherein B is an acyl derivative of formula $R_4$—C(O)— wherein $R_4$ is (i) $C_{1-10}$ alkyl optionally substituted with carboxyl, hydroxy or $C_{1-6}$ alkoxy, or (ii) $C_{3-7}$ cycloalkyl or $C_{4-10}$ alkylcycloalkyl, both optionally substituted with hydroxy, carboxyl, ($C_{1-6}$ alkoxy) carbonyl, or (iv) $C_6$ or $C_{10}$ aryl or $C_{7-16}$ aralkyl, all optionally substituted with $C_{1-6}$ alkyl, hydroxy, or (v) Het optionally substituted with $C_{1-6}$ alkyl, hydroxy, amido or amino.

11. A compound of formula I according to claim 5, wherein B is a carboxyl derivative of formula $R_4$—O—C(O)—, wherein $R_4$ is (i) $C_{1-10}$ alkyl optionally substituted with carboxyl, $C_{1-6}$ alkanoyl, hydroxy, $C_{1-6}$ alkoxy or amido, (lower alkyl) amide, amino optionally mono- or di-substituted with $C_{1-6}$ alkyl;

(ii) $C_{3-7}$ cycloalkyl, $C_{4-10}$ alkylcycloalkyl, all optionally substituted with carboxyl, ($C_{1-6}$ alkoxy)carbonyl, amido, (lower alkyl)amide, amino optionally mono- or di-substituted with $C_{1-6}$ alkyl, or (iv) $C_6$ or $C_{10}$ aryl or $C_{7-16}$ aralkyl, all optionally substituted with $C_{1-6}$ alkyl, hydroxy, amino optionally substituted with $C_{1-6}$ alkyl; or (v) Het or (lower alkyl)-Het, both optionally substituted with $C_{1-6}$ alkyl, hydroxy, amido, or amino optionally mono-substituted with $C_{1-6}$ alkyl.

12. A compound of formula I according to claim 6, wherein B is an amide derivative of formula $R_4$—N($R_5$)— C(O)— wherein $R_4$ is (i) $C_{1-10}$ alkyl optionally substituted with carboxyl, $C_{1-6}$ alkanoyl, hydroxy, $C_{1-6}$ alkoxy, amido, (lower alkyl) amide, amino optionally mono- or di-substituted with $C_{1-6}$ alkyl;

(ii) $C_{3-7}$ cycloalkyl or $C_{4-10}$ alkylcycloalkyl, all optionally substituted with carboxyl, ($C_{1-6}$ alkoxy)carbonyl, amido, (lower alkyl)amide, amino optionally mono- or di-substituted with $C_{1-6}$ alkyl;

(iii) amino optionally mono- or di-substituted with $C_{1-3}$ alkyl, or (iv) $C_6$ or $C_{10}$ aryl or $C_{7-16}$ aralkyl, all optionally substituted with $C_{1-6}$ alkyl, hydroxy, amino or amido optionally substituted with $C_{1-6}$ alkyl; or (v) Het optionally substituted with $C_{1-6}$ alkyl, hydroxy, amino or amido, and $R_5$ is H.

13. A compound of formula I according to claim 7, wherein B is a thioamide derivative of formula $R_4$—NH— C(S)—; wherein $R_4$ is (i) $C_{1-10}$ alkyl; or (ii) $C_{3-7}$ cycloalkyl.

14. A compound of formula I according to claim 12, wherein B is an amide derivative of formula $R_4$—NH—C (O)— wherein $R_4$ is (i) $C_{1-10}$ alkyl optionally substituted with carboxyl, $C_{1-6}$ alkanoyl, hydroxy, $C_{1-6}$ alkoxy amido, (lower alkyl) amide, amino optionally mono- or di-substituted with $C_{1-6}$ alkyl;

(ii) $C_{3-7}$ cycloalkyl or $C_{4-10}$ alkylcycloalkyl, all optionally substituted with carboxyl, ($C_{1-6}$ alkoxy)carbonyl, amido, (lower alkyl)amide, amino optionally mono- or di-substituted with $C_{1-6}$ alkyl;

151

(iv) $C_6$ or $C_{10}$ aryl or $C_{7-16}$ aralkyl optionally substituted with $C_{1-6}$ alkyl, hydroxy, amino or amido.

15. A compound of formula I according to claim 1, wherein B is

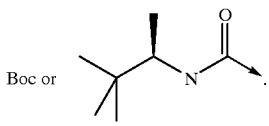

16. A compound of formula I according to claim 1, wherein Y is H or methyl.

17. A compound of formula I according to claim 16, wherein Y is H.

18. A compound of formula I according to claim 1, wherein $R^3$ is $C_{1-8}$ alkyl, $C_{3-7}$ cycloalkyl, or $C_{4-10}$ alkylcycloalkyl, all optionally substituted with hydroxy, $C_{1-6}$ alkoxy, $C_{1-6}$ thioalkyl, acetamido, $C_6$ or $C_{10}$ aryl, or $C_{7-16}$ aralkyl.

19. A compound of formula I according to claim 18, wherein $R^3$ is the side chain of Tbg, Ile, Val, Chg or:

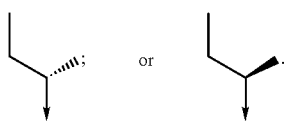

20. A compound of formula I according to claim 19, wherein $R^3$ is the side chain of Tbg, Chg or Val.

21. A compound of formula I according to claim 1, wherein $R^2$ is S—$R_{20}$ or O—$R_{20}$ wherein $R_{20}$ is a pyrimidinyl, quinazolinyl, —$CH_2$-pyrimidinyl or —$CH_2$-quinazolinyl, all optionally mono, di- or tri-substituted with $R_{21}$, wherein $R_{21}$ is $C_{1-6}$ alkyl; $C_{1-6}$ alkoxy; lower thioalkyl; amino or amido optionally mono-or di-substituted with $C_{1-6}$ alkyl, $C_6$ or $C_{10}$ aryl, $C_{7-16}$ aralkyl, Het or (lower alkyl)-Het; $NO_2$; OH; halo; trifluoromethyl; carboxyl; $C_6$ or $C_{10}$ aryl, $C_{7-16}$ aralkyl, or Het, said aryl, aralkyl or Het being optionally substituted with $R_{22}$, wherein $R_{22}$ is $C_{1-6}$ alkyl; $C_{3-7}$ cycloalkyl; $C_{1-6}$ alkoxy; amino; mono- or di-(lower alkyl)amino; (lower alkyl)amide; sulfonylalkyl; $NO_2$; OH; halo; trifluoromethyl; carboxyl or Het.

22. A compound of formula I according to claim 21, wherein $R_{21}$ is $C_{1-6}$ alkyl; $C_{1-6}$ alkoxy; amino; di(lower alkyl)amino; (lower alkyl)amide; $C_6$ or $C_{10}$ aryl, or Het, said aryl or Het being optionally substituted with $R_{22}$, wherein $R_{22}$ is $C_{1-6}$ alkyl; $C_{3-7}$ cycloalkyl; $C_{1-6}$ alkoxy, amino; mono- or di (lower alkyl)amino; amido; (lower alkyl)amide; halo; trifluoromethyl or Het.

23. A compound of formula I according to claim 22, wherein $R_{22}$ is $C_{1-6}$ alkyl; $C_{1-6}$ alkoxy; halo; amino optionally mono- or di-substituted with lower alkyl; amido; (lower alkyl)amide; or Het.

24. A compound of formula I according to claim 23, wherein $R_{22}$ is methyl; ethyl; isopropyl; tert-butyl; methoxy; chloro; amino optionally mono- or di-substituted with lower alkyl; amido, (lower alkyl)amide; or (lower alkyl) 2-thiazole.

25. A compound of formula I according to claim 21, wherein $R^2$ selected from the group consisting of:

152

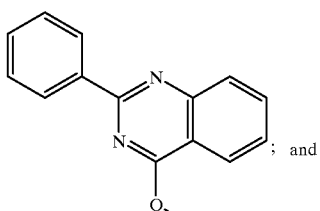

; and

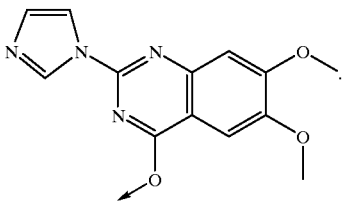

.

26. A compound of formula I according to claim 1, wherein $R^1$ is H, $C_{1-3}$ alkyl, $C_{3-5}$ cycloalkyl, or $C_{2-4}$ alkenyl, all optionally substituted with halo.

27. A compound of formula I according to claim 26, wherein P1 is:

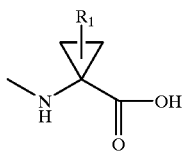

and $R^1$ is ethyl, vinyl, cyclopropyl, 1 or 2-bromoethyl or 1 or 2-bromovinyl.

28. A compound of formula I according to claim 27, wherein $R^1$ is vinyl.

29. A compound of formula I according to claim 27, wherein $R^1$ at carbon 2 is orientated syn to the carbonyl at position 1, represented by the radical:

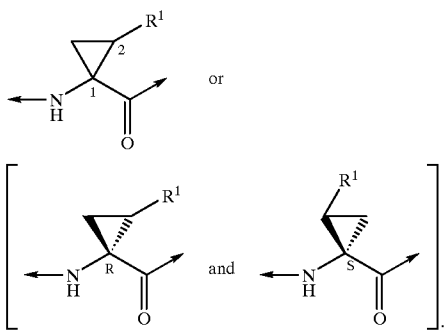

30. A compound of formula I according to claim 27, wherein $R^1$ at position 2 is orientated anti to the carbonyl at position 1, represented by the radical:

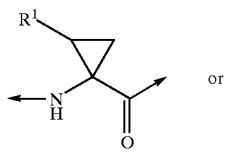

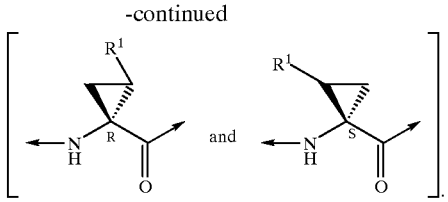

31. A compound of formula I according to claim 27, wherein carbon 1 has the R configuration:

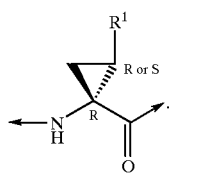

32. An optical isomer of a compound of formula I according to claim 31, wherein said $R^1$ substituent and the carbonyl in a syn orientation in the following absolute configuration:

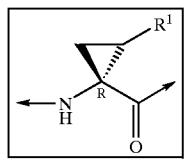

33. A compound of formula I according to claim 32, wherein $R^1$ is ethyl, hence the asymmetric carbon atoms at positions 1 and 2 have the R,R configuration.

34. A compound of formula I according to claim 32, wherein $R^1$ is vinyl, hence the asymmetric carbon atoms at positions 1 and 2 have the R,S configuration.

35. A compound of formula I according to claim 1, wherein

B is a $C_6$ or $C_{10}$ aryl or $C_{7-16}$ aralkyl, all optionally substituted with $C_{1-6}$ alkyl, $C_{1-6}$ alkoxy, $C_{1-6}$ alkanoyl, hydroxy, hydroxyalkyl, halo, haloalkyl, nitro, cyano, cyanoalkyl, amido, (lower alkyl)amido, or amino optionally substituted with $C_{1-6}$ alkyl; or Het or (lower alkyl)-Het, all optionally substituted with $C_{1-6}$ alkyl, $C_{1-6}$ alkoxy, $C_{1-6}$ alkanoyl, hydroxy, hydroxyalkyl, halo, haloalkyl, nitro, cyano, cyanoalkyl, amido, (lower alkyl)amido, or amino optionally substituted with $C_{1-6}$ alkyl, or B is $R_4$—$SO_2$ wherein $R_4$ is amido; (lower alkyl)amide; $C_6$ or $C_{10}$ aryl, $C_{7-14}$ aralkyl or Het, all optionally substituted with $C_{1-6}$ alkyl, or B is an acyl derivative of formula $R_4$—C(O)— wherein $R_4$ is
(i) $C_{1-10}$ alkyl optionally substituted with carboxyl, hydroxy or $C_{1-6}$ alkoxy, amido, (lower alkyl)amide, or amino optionally mono- or di-substituted with $C_{1-6}$ alkyl;
(ii) $C_{3-7}$ cycloalkyl or $C_{4-10}$ alkylcycloalkyl, both optionally substituted with hydroxy, carboxyl, ($C_{1-6}$ alkoxy)carbonyl, amido, (lower alkyl)amide, or amino optionally mono- or di-substituted with $C_{1-6}$ alkyl;
(iv) $C_6$ or $C_{10}$ aryl or $C_{7-16}$ aralkyl, all optionally substituted with $C_{1-6}$ alkyl, hydroxy, amido, (lower alkyl)amide, or amino optionally substituted with $C_{1-6}$ alkyl;
(v) Het or (lower alkyl)-Het, both optionally substituted with $C_{1-6}$ alkyl, hydroxy, amino optionally substituted with $C_{1-6}$ alkyl, amido, (lower alkyl)amide, or amino optionally substituted with $C_{1-6}$ alkyl, or B is a carboxyl derivative of formula $R_4$—O—C(O)—, wherein $R_4$ is
(i) $C_{1-10}$ alkyl optionally substituted with carboxyl, $C_{1-6}$ alkanoyl, hydroxy, $C_{1-6}$ alkoxy, amino optionally mono- or di-substituted with $C_{1-6}$ alkyl, amido or (lower alkyl)amide;
(ii) $C_{3-7}$ cycloalkyl, $C_{4-10}$ alkylcycloalkyl, all optionally substituted with carboxyl, ($C_{1-6}$ alkoxy)carbonyl, amino optionally mono- or di-substituted with $C_{1-6}$ alkyl, amido or (lower alkyl)amide;
(iv) $C_6$ or $C_{10}$ aryl or $C_{7-16}$ aralkyl optionally substituted with $C_{1-6}$ alkyl, hydroxy, amido, (lower alkyl) amido, or amino optionally mono- or di-substituted with $C_{1-6}$ alkyl; or
(v) Het or (lower alkyl)-Het, both optionally substituted with $C_{1-6}$ alkyl, hydroxy, amino optionally mono- or di-substituted with $C_{1-6}$ alkyl, amido or (lower alkyl) amido, or B is an amide derivative of formula $R_4$—N($R_5$)—C(O)— wherein $R_4$ is
(i) $C_{1-10}$ alkyl optionally substituted with carboxyl, $C_{1-6}$ alkanoyl, hydroxy, $C_{1-6}$ alkoxy, amido, (lower alkyl)amido, or amino optionally mono- or di-substituted with $C_{1-6}$ alkyl;
(ii) $C_{3-7}$ cycloalkyl or $C_{4-10}$ alkylcycloalkyl, all optionally substituted with carboxyl, ($C_{1-6}$ alkoxy)carbonyl, amido, (lower alkyl)amido, or amino optionally mono- or di-substituted with $C_{1-6}$ alkyl;
iii) amino optionally mono- or di-substituted with $C_{1-3}$ alkyl;
(iv) $C_6$ or $C_{10}$ aryl or $C_{7-16}$ aralkyl, all optionally substituted with $C_{1-6}$ alkyl, hydroxy, amido, (lower alkyl)amide, or amino optionally substituted with $C_{1-6}$ alkyl; or
(v) Het or (lower alkyl)-Het, both optionally substituted with $C_{1-6}$ alkyl, hydroxy, amino optionally substituted with $C_{1-6}$ alkyl, amido or (lower alkyl)amide; and $R_5$ is H or methyl, or B is thioamide derivative of formula $R_4$—NH—C(S)—; wherein $R_4$ is
(i) $C_{1-10}$ alkyl optionally substituted with carboxyl, $C_{1-6}$ alkanoyl or $C_{1-6}$ alkoxy;
(ii) $C_{3-7}$ cycloalkyl or $C_{4-10}$ alkylcycloalkyl, all optionally substituted with carboxyl, ($C_{1-6}$ alkoxy) carbonyl, amino or amido;

Y is H or methyl; $R^3$ is $C_{1-8}$ alkyl, $C_{3-7}$ cycloalkyl, or $C_{4-10}$ alkylcycloalkyl, all optionally substituted with hydroxy, $C_{1-6}$ alkoxy, $C_{1-6}$ thioalkyl, acetamido, $C_6$ or $C_{10}$ aryl, or $C_{7-16}$ aralkyl;

$R^2$ is S—$R_{20}$ or O—$R_{20}$ wherein $R_{20}$ is pyrimidinyl, quinazolinyl, —$CH_2$-pyrimidinyl or —$CH_2$-pyrimidinyl or —$CH_2$—quinazolinyl, all optionally mono-, di- or tri-substituted with $R_{21}$, wherein $R_{21}$ is $C_{1-6}$ alkyl; $C_{1-6}$ alkoxy; lower thioalkyl; amino or amido optionally mono-or di-substituted with $C_{1-6}$ alkyl, $C_6$ or $C_{10}$ aryl, $C_{7-16}$ aralkyl, Het or (lower alkyl)-Het; $NO_2$; OH; halo; trifluoromethyl; carboxyl; $C_6$ or $C_{10}$ aryl, $C_{7-16}$ aralkyl, or Het, said aryl, aralkyl or Het being optionally substituted with $R_{22}$, wherein $R_{22}$ is $C_{1-6}$ alkyl; $C_{3-7}$ cycloalkyl; $C_{1-6}$ alkoxy; amino; mono- or di-(lower alkyl)amino; (lower alkyl)amide; sulfonylalkyl; NO₂; OH; halo; trifluoromethyl; carboxyl or Het; or R² is selected from the group consisting of:

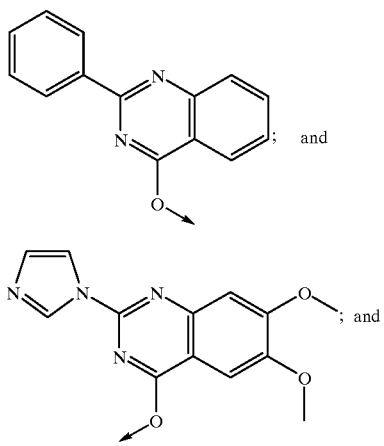; and

P1 is:

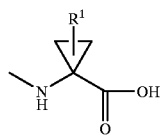

wherein R¹ is H, $C_{1-3}$ alkyl, $C_{3-5}$ cycloalkyl, or $C_{2-4}$ alkenyl optionally substituted with halo, and said R¹ at carbon 2 is orientated syn to the carbonyl at position 1, represented by the radical:

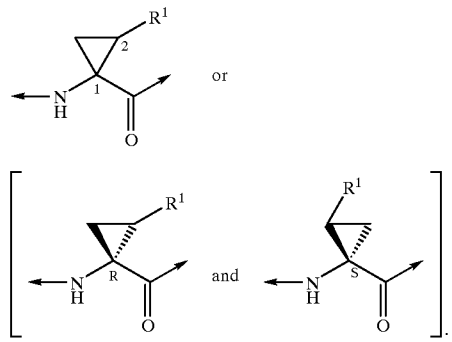

or a pharmaceutically acceptable salt or ester thereof.

36. A compound according to claim 35 represented by the formula:

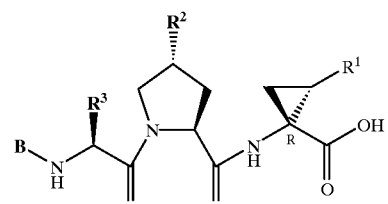

wherein B, [R₃, R₂, R₁] R³, R², R¹ are as defined below:

| Table 3 Cpd # | B | [R₃]R³ | [R₂]R² | [R₁] R¹ syn to carboxyl |
|---|---|---|---|---|
| [301 | Boc | cHex | —O—CH₂-1-naphthyl | ethyl ; |
| 302 | iBu-O-C(O)- | iPr | —O—CH₂-1-naphthyl | ethyl ; |
| 303 | iBu-O-C(O)- | cHex | —O—CH₂-1-naphthyl | ethyl ; |
| 304 | Boc | cHex | 8-quinolinyl-OCH₂- | ethyl ; |
| 305 | Boc | cHex | —O—CH₂-1-naphthyl | vinyl ; |

-continued
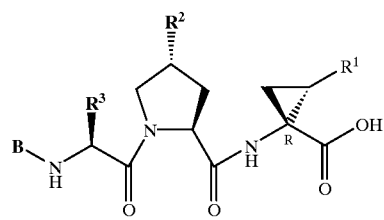
wherein B, [R₃, R₂, R₁] R³, R², R¹ are as defined below:
| Table 3 Cpd # | B | [R₃]R³ | [R₂]R² | [R₁] R¹ syn to carboxyl |
|---|---|---|---|---|
| 306 | Boc | cHex | 4-quinolinyloxy | vinyl ; |
| 307 | Boc | cHex | 2-phenyl-6-nitro-4-quinolinyloxy | vinyl ; |
| 308 | Boc | cHex | 1-naphthyloxy | vinyl ; |
| 309 | Boc | cHex | 2-naphthyloxy | vinyl ; |
| 310 | Boc | cHex | 5-isoquinolinyloxy | vinyl ; |
| 311 | Boc | cHex | 7-chloro-4-quinolinyloxy | vinyl ; |

-continued
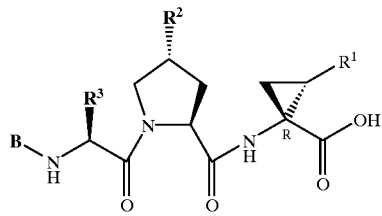
wherein B, [R₃, R₂, R₁] R³, R², R¹ are as defined below:
| Table 3 Cpd # | B | [R₃]R³ | [R₂]R² | [R₁] R¹ syn to carboxyl |
|---|---|---|---|---|
| 312 | Boc | cHex | 5-quinolinyloxy | vinyl ; |
| 313 | Boc | cHex | 2-methyl-4-quinolinyloxy | vinyl ; |
| 314 | Boc | cHex | 2-phenyl-4-quinolinyloxy | vinyl ; |
| 315 | Boc | cHex | 2-phenyl-6-amino-4-quinolinyloxy | vinyl ; |
| 316 | Acetyl | cHex | 2-phenyl-4-quinolinyloxy | vinyl ; |

-continued
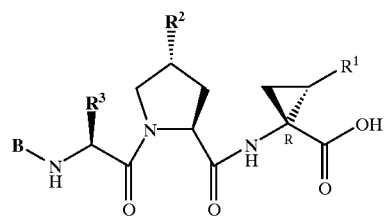
wherein B, [R₃, R₂, R₁] R³, R², R¹ are as defined below:
| Table 3 Cpd # | B | [R₃]R³ | [R₂]R² | [R₁] R¹ syn to carboxyl |
|---|---|---|---|---|
| 317 | Boc | cHex | 2-phenyl-6-acetamido-quinolin-4-yloxy | vinyl ; |
| 318 | CF₃—C(O)— | i-Pr | 2-phenyl-quinolin-4-yloxy | vinyl ;] |
| 319 | methyl 4-benzoate | cHex | 2-phenyl-quinazolin-4-yloxy | vinyl ; |
| 320 | 4-benzoic acid | cHex | 2-(4-trifluoromethylphenyl)-8-trifluoromethyl-quinolin-4-yloxy | vinyl ; |
| 321 | Boc | t-Bu | 2-phenyl-quinazolin-4-yloxy | vinyl ; |

-continued

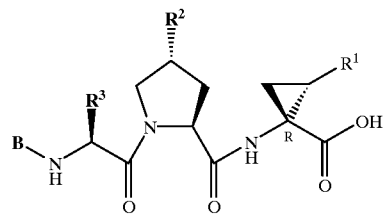

wherein B, [R₃, R₂, R₁] R³, R², R¹ are as defined below:

| Table 3 Cpd # | B | [R₃]R³ | [R₂]R² | [R₁] R¹ syn to carboxyl |
|---|---|---|---|---|
| [322 | Boc | t-Bu | 2-(4-trifluoromethylphenyl)-8-trifluoromethyl-quinolin-4-yloxy | vinyl ;] |
| 323 | Boc | t-Bu | 2-phenylquinazolin-4-yloxy | cyclopropyl ; |
| [324 | Boc | t-Bu | 2-morpholino-6,7-dimethoxyquinazolin-4-yloxy | vinyl ; |
| 325 | Boc | t-Bu | 2-phenyl-7-methoxyquinolin-4-yloxy | cyclopropyl ;] |
| 326 | Boc | t-Bu | 2-(imidazol-1-yl)-7-methoxyquinazolin-4-yloxy | vinyl ; |

-continued
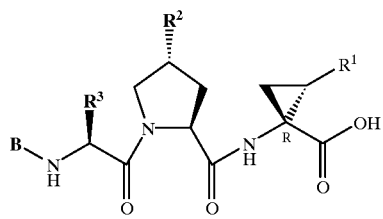
wherein B, [R₃, R₂, R₁] R³, R², R¹ are as defined below:
| Table 3 Cpd # | B | [R₃]R³ | [R₂]R² | [R₁] R¹ syn to carboxyl |
|---|---|---|---|---|
| [327 | *t*-BuNHC(O)CH₂– | t-Bu | 7-methoxy-4-quinolinyloxy | vinyl ; |
| 328 | Boc | t-Bu | 4-chloro-2-quinolinyloxy | vinyl ; |
| 329 | Boc | t-Bu | 2,2':6',2''-terpyridin-4'-yloxy | vinyl ; |
| 330 | Boc | t-Bu | 2-acetyl-1,2,3,4-tetrahydroisoquinolin-5-yloxy | vinyl ; |
| 331 | *t*-BuNHC(O)CH₂– | t-Bu | 2-phenyl-4-quinolinyloxy | vinyl ; |

-continued

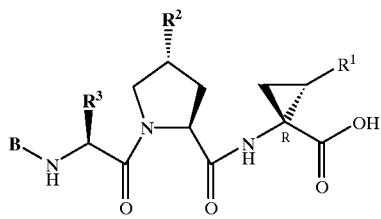

wherein B, [R₃, R₂, R₁] R³, R², R¹ are as defined below:

Table 3

| Cpd # | B | [R₃]R³ | [R₂]R² | [R₁] R¹ syn to carboxyl |
|---|---|---|---|---|
| 332 | Boc | t-Bu | (2-phenyl-7-methoxyquinolin-4-yloxy) | ethyl ; |
| 333 | (S)-N-acetyl-tert-butylmethyl | t-Bu | (2-(2-acetamidothiazol-4-yl)-7-methoxyquinolin-4-yloxy) | vinyl ; |
| and 334 | (S)-N-acetyl-tert-butylmethyl | t-Bu | (2-(2-ethylaminothiazol-4-yl)-7-methoxyquinolin-4-yloxy) | vinyl ]. |

37. A compound according to claim 36, selected from the group consisting of compound #: 319, 321, and 326.

38. A pharmaceutical composition comprising an anti-hepatitis C virally effective amount of a compound of a compound of formula I according to claim 1, or a therapeutically acceptable salt or ester thereof, in admixture with a pharmaceutically acceptable carrier medium or auxilliary agent.

39. A method of treating a hepatitis C viral infection in a mammal comprising administering to the mammal an anti-hepatitis C virally effective amount of the compound of formula I according to claim 1, or a therapeutically acceptable salt or ester thereof.

40. A method of treating a hepatitis C viral infection in a mammal comprising administering to the mammal an anti-hepatitis C virally effective amount of the composition according to claim 39.

41. A method of inhibiting the replication of hepatitis C virus comprising exposing the virus to a hepatitis C viral NS3 protease inhibiting amount of the compound of formula I according to claim 1, or a therapeutically acceptable salt or ester thereof.

42. A method of treating a hepatitis C viral infection in a mammal comprising administering thereto an anti-hepatitis C virally effective amount of a combination of the compound of formula I according to claim 1, or a therapeutically acceptable salt or ester thereof with another anti-HCV agent.

43. A method according to claim 42, wherein said other anti-HCV agent is selected from the group consisting of: α- or β-interferon, ribavirin and amantadine.

44. A method according to claim 42, wherein said other anti-HCV agent comprises an inhibitor of other targets in the HCV life cycle, selected from: helicase, polymerase, metalloprotease or IRES.

45. A process for the preparation of a peptide analog of formula (I) according to claim 1 wherein P1 is a substituted aminocyclopropyl carboxylic acid residue, comprising the step of:
coupling a peptide selected from the group consisting of: APG-P3-P2; or APG-P2; with a P1 intermediate of formula:

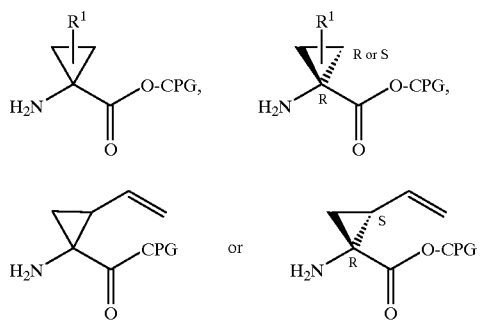

wherein $R^1$ is $C_{1-6}$ alkyl, cycloalkyl or $C_{2-6}$ alkenyl, all optionally substituted with halogen, CPG is a carboxyl protecting group an APG is an amino protecting group an P3 an P2 are as defined above.

46. A process for the preparation of: a peptide analog of formula (I) according to claim 1, this process comprising the step of:
coupling a suitably protected amino acid, peptide or peptide fragment with a P1 intermediate of formula:

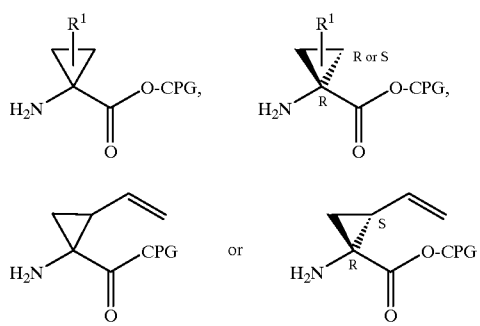

wherein $R^1$ is $C_{1-6}$ alkyl, cycloalkyl or $C_{2-6}$ alkenyl, all optionally substituted with halogen, and CPG is a carboxyl protecting group.

47. A process for the preparation of: a peptide analog of formula (I) according to claim 1, this process comprising the step of:
coupling a suitably protected amino acid, peptide or peptide fragment with a P1 intermediate of formula:

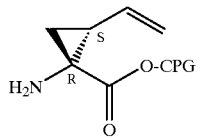

wherein CPG is a carboxyl protecting group.

48. The process according to claim 45, 46 or 47 wherein said carboxyl protecting group (CPG) is selected from the group consisting of:
alkyl esters, aralkyl esters, and esters being cleavable by mild base treatment or mild reductive means.

49. Method of preparing a composition for treating a hepatitis C viral infection in a mammal comprising combining an anti-hepatitis C virally effective amount of the compound of formula I according to claim 1, or a therapeutically acceptable salt or ester thereof, with a pharmaceutically acceptable carrier medium or auxiliary agent.

50. Method of preparing a composition for inhibiting the replication of hepatitis C virus comprising combining a hepatitis C viral NS3 protease inhibiting amount of the compound of formula I according to claim 1, or a therapeutically acceptable salt or ester thereof, with a pharmaceutically acceptable carrier medium or auxiliary agent.

51. Method of preparing a composition for treating a hepatitis C viral infection in a mammal comprising combining an anti-hepatitis C virally effective amount of a combination of the compound of formula I according to claim 1, or a therapeutically acceptable salt or ester thereof, and an interferon with a pharmaceutically acceptable carrier medium or auxiliary agent.

52. A compound of formula (I) according to claim 1, wherein each Het group is independently selected from the group consisting of pyrrolidine, tetrahydrofuran, thiazolidine, pyrrole, 1,4-dioxane, indole, or any of the following heterocycles:

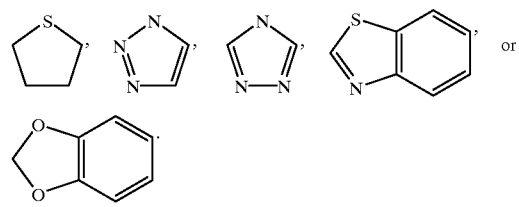

* * * * *